(12) United States Patent
Deng et al.

(10) Patent No.: US 11,028,369 B2
(45) Date of Patent: Jun. 8, 2021

(54) INDUCED EXTENDED PLURIPOTENT STEM CELLS, METHOD OF MAKING AND USING

(71) Applicants: Beihao Stem Cell and Regenerative Medicine Research Institute Co., Ltd., Guangdong (CN); Peking University, Beijing (CN); Hong Guan Ltd., Bejing (CN)

(72) Inventors: Hongkui Deng, Beijing (CN); Yang Yang, Beijing (CN); Bei Liu, Beijing (CN); Jun Xu, Beijing (CN)

(73) Assignees: Beihao Stem Cell and Regenerative Medicine Research Institute Co., Ltd., Guangdong (CN); Peking University, Beijing (CN); Hong Guan Ltd., Beijing (CN)

( * ) Notice: Subject to any disclaimer, the term of this patent is extended or adjusted under 35 U.S.C. 154(b) by 0 days.

(21) Appl. No.: 15/746,398

(22) PCT Filed: Aug. 12, 2016

(86) PCT No.: PCT/CN2016/094828
§ 371 (c)(1),
(2) Date: Jan. 19, 2018

(87) PCT Pub. No.: WO2017/025061
PCT Pub. Date: Feb. 16, 2017

(65) Prior Publication Data
US 2018/0195046 A1     Jul. 12, 2018

(30) Foreign Application Priority Data
Aug. 13, 2015   (WO) ................ PCT/CN2015/086854

(51) Int. Cl.
| | | |
|---|---|---|
| *C12N 5/0735* | (2010.01) | |
| *C12N 15/873* | (2010.01) | |
| *C12N 5/073* | (2010.01) | |
| *A61K 35/545* | (2015.01) | |
| *C12N 5/074* | (2010.01) | |
| *C07K 16/38* | (2006.01) | |
| *C07K 16/40* | (2006.01) | |
| *A01K 67/027* | (2006.01) | |

(52) U.S. Cl.
CPC ........ *C12N 5/0696* (2013.01); *A01K 67/0271* (2013.01); *A61K 35/545* (2013.01); *C07K 16/38* (2013.01); *C07K 16/40* (2013.01); *C12N 5/0605* (2013.01); *C12N 5/0606* (2013.01); *C12N 15/873* (2013.01); *A01K 2207/12* (2013.01); *A01K 2217/00* (2013.01); *A01K 2227/105* (2013.01); *C12N 2501/15* (2013.01); *C12N 2501/20* (2013.01); *C12N 2501/235* (2013.01); *C12N 2501/2306* (2013.01); *C12N 2501/237* (2013.01); *C12N 2501/2311* (2013.01); *C12N 2501/2327* (2013.01); *C12N 2501/2331* (2013.01); *C12N 2501/603* (2013.01); *C12N 2501/999* (2013.01); *C12N 2503/02* (2013.01); *C12N 2510/00* (2013.01)

(58) Field of Classification Search
CPC .... C12N 5/0696; C12N 5/606; C12N 5/0605; C12N 2501/235; C12N 2501/999
See application file for complete search history.

(56) References Cited

U.S. PATENT DOCUMENTS

| | | | |
|---|---|---|---|
| 2013/0011921 A1* | 1/2013 | Hishida | C12N 5/0696 435/354 |
| 2013/0119121 A1* | 5/2013 | Cenzano | B65D 27/14 229/79 |
| 2014/0315305 A1 | 10/2014 | Shimmura | |

FOREIGN PATENT DOCUMENTS

| | | | | |
|---|---|---|---|---|
| WO | 2004018655 | | 3/2004 | |
| WO | WO-2004018655 A2 * | | 3/2004 | ........... C12N 5/0623 |
| WO | 2010033138 | | 3/2010 | |
| WO | 2011056971 | | 5/2011 | |
| WO | WO-2011056971 A2 * | | 5/2011 | ........... A61K 35/545 |
| WO | 2011102333 | | 8/2011 | |
| WO | 2010/021390 | | 1/2012 | |
| WO | 2012078153 | | 6/2012 | |
| WO | 2013094771 | | 6/2013 | |
| WO | 2014/174470 | | 10/2014 | |

OTHER PUBLICATIONS

Kim et al Nat Commun. 4: 2403 (Year: 2013).*
Alano et al PNAS, 103, 9685-9690 (Year: 2006).*
(Continued)

*Primary Examiner* — Anoop K Singh
(74) *Attorney, Agent, or Firm* — Pabst Patent Group LLP

(57) ABSTRACT

Factors for extending the ability of isolated pluripotent stem cells to generate extraembryonic lineages in vivo, following in vitro culture, herein, chemical extenders of pluripotency (CEP). Methods of extending the ability of a pluripotent cell to generate embryonic and extraembryonic lineages. The cell to be reprogrammed is contacted with effective amounts of the CEPs for a sufficient period of time to reprogram the cell into a chemically induced extended pluripotent cell (ciEPSC). ciEPSC are identified as an extended pluripotent cell based on properties including: (i) morphologically and (ii) functionally for example, based on their ability contribute to both TE and ICM, in vivo. The ciEPSCs can be cultured or induced to differentiate into cells of a desired type, and used in a number of applications, including but not limited to cell therapy and tissue engineering.

5 Claims, 18 Drawing Sheets
Specification includes a Sequence Listing.

(56) References Cited

OTHER PUBLICATIONS

Pfaff et al European Journal of Pharamcology, 286, 229-240 (Year: 1995).*
Abad, et al., "Reprogramming in vivo produces teratomas and iPS cells with totipotency features", Nature, 502:340-344 (2013).
Bueker, et al., "Reorganization of enhancer patterns in transition from naïve to primed pluripotency", Cell Stem Cell, 14(6):838-853 (2014).
Chatzidaki, et al., "Pharmalogical characterisation of nicotinic acethylcholine receptors expressed in human iPSC-derived neurons", PLOS one, 10(4):e0125116 (2015).
Choi, et al., "G protein-coupled receptors in stem cell maintenance and somatic reprogramming to pluripotent or cancer stem cells", BMB Reports, 48(2):68-80 (2015).
Hamanaka, et al., "Generation of germline-competent rat induced pluripotent stem cells", PLOSone, 6:e22008 (2011).
Huang, et al., "Molecular basis of embryonic stem cell self-renewal: from signaling pathways to pluripotency network", CMLS Cellular and Molecular Life Sciences, 72(9):1741-1757 (2015).
Jiang, et al., "Poly(ADP-Ribose) Polymerase 1: Cellular Pluripotency, Reprogramming, and Tumorgenesis", International Journal of Molecular Sciences, 16(12):15531-15545 (2015).
Nichols, et al., "Pluripotency in the embryo and in culture", Cold Spring Harbor Perspectives in Biology, 4(8):a008128 (2012).
Xie, et al., "Enhancing pluripotency and lineage specification", Science, 341(6143):245-247 (2013).
Yang, et al., "Derivation of pluripotent stem cells with in vivo embryonic and extraembryonic potency", Cell, 169(2):243 (2017).
Brundula, et al., "Targeting leukocyte MMPs and transmigration Minocycline as a potential therapy for multiple sclerosis", *Brain*, 125:1297-1308 (2002).
Office Action from counterpart Australian Patent Office for Australian Application No. 2016305705 dated Feb. 15, 2019.
Office Action from counterpart Canadian Patent Office for Canadian Application No. 2,994,192 dated Jan. 15, 2019.
Extended European Search Report for European Application No. 168346856 dated Dec. 3, 2018.
Office Action from counterpart Korean Patent Office for Korean Application No. 10-2018-7005213 dated Jan. 28, 2019.
English Translation of Korean Office Action for Korean Application No. 10-2018-7005213 dated Jan. 28, 2019.
Office Action from counterpart Japanese Patent Office for Japanese Application No. 2018-526987 dated Apr. 9, 2019.
English Translation of Japanese Office Action for Japanese Application No. 2018-526987 dated Apr. 9, 2019.
Buehr, et al., Capture of authentic embryonic stem cells from rat blastocysts, Cell 135:1287-98 (2008).
Chan, et al., "Induction of a human pluripotent state with distinct regulatory circuitry that resembles preimplantation epiblast". Cell Stem Cell. 13:663-75 (2013).
Evans and Kaufman, "Establishment in culture of pluripotential cells from mouse embryos", Nature, 292:154-56 (1981).
Gafni, et al., "Derivation of novel human ground state naïve pluripotent stem cells", Nature, 504(7479):282-6 (2013).
Han, et al., "Epiblast stem cell subpopulations represent mouse embryos of distinct pregastrulation stages", Cell, 143:617-27 (2010).
Li, et al., "Germline competent embryonic stem cells derived from rat blastocysts", Cell, 135(7):1299-310 (2008).
Marikawa and Alarcon, "Establishment of trophectoderm and inner cell mass lineages in the mouse embryo", Mol Reprod Dev., 76(11):1019-32 (2009).
Tachibana, et al., "Generation of chimeric rhesus monkeys", Cell, 148(1-2):285-95 (2012).
Takashima, et al., "Resetting transcription factor control circuitry toward ground-state pluripotency in human", Cell, 158:1254-69 (2014).
Theunissen, et al., "Systematic identification of culture conditions for induction and maintenance of naïve human pluripotency", Cell Stem Cell, 15:471-87 (2014).
Thomson. Et al., "Embryonic stem cells lines derived from human blastocysts", Science, 282:1145-7 (1998).
English Translation of Korean Office Action for Korean Application No. 10-2018-7005213 dated Feb. 27, 2020.

* cited by examiner

INDUCED EXTENDED PLURIPOTENT STEM CELLS, METHOD OF MAKING AND USING

CROSS-REFERENCE TO RELATED APPLICATIONS

This application is a 371 application of PCT/CN2016/094828, filed Aug. 12, 2016, which claims the priority to and benefit of PCT/CN2015/086854, filed Aug. 13, 2015, the disclosures of which are hereby incorporated herein by reference in their entirety.

FIELD OF THE INVENTION

The invention is generally directed to compositions and methods for extending in vivo pluripotency of in vitro cultured pluripotent stem cells.

BACKGROUND OF THE INVENTION

Totipotent cells in early embryos are progenitors of all stem cells and are capable of developing into a whole organism, including extraembryonic tissues such as placenta. Pluripotent cells in the inner cell mass (ICM) are the descendants of totipotent cells and can differentiate into any cell type of a body except extraembryonic tissues.

Animal development is initiated by fertilization of the egg with sperm, which is immediately followed by mitotic cell divisions, or cleavages, to generate blastomeres. In most animals, the first step of cell type diversification is the creation of the primary germ layers, namely endoderm, mesoderm and ectoderm. In general, endoderm is the precursor of the gastrointestinal tract, which is essential for nutrient absorption; mesoderm gives rise to muscle and blood cells, which are involved in locomotion and cardiovascular circulation, respectively; and ectoderm develops into epidermis and neurons, which are critical for protection from and sensing of the environment, respectively. Thus, the formation of the three germ layers lays the groundwork for generating various tissues that are essential for animal life, and is an evolutionarily conserved event that takes place at the beginning of animal development.

The situation, however, is slightly different for the development of mammals, specifically eutherians, such as the mouse and human. The first cell differentiation event in mammalian development is not the formation of the three germ layers, but is the establishment of two distinct cell lineages: the trophectoderm (TE) and the inner cell mass (ICM). TE engages in implantation by directly interacting with the mother's uterus, and gives rise to tissues in the placenta. It is only after implantation that the three germ layers form from the ICM, which ultimately generates all the tissues in the animal body. Reviewed in Marikawa, et al., *Mol. Reprod. Dev.*, 76(11):1019-1032 (2009).

ESCs (embryonic stem cells) are the in vitro counterparts of pluripotent cells residing in the ICM of blastocysts. While natural pluripotent cells in the developing embryo exist transiently, ESCs can be maintained in vitro, providing an unlimited source of undifferentiated cells. Tachiban, et al., *Cell*, 148(1-2):285-295 (2012). The downstream application of isolated in vitro cultured pluripotent stem cells depend on their potency i.e., their ability to differentiate into other cell types and the ease with which/the ability to rapidly expand the cells in vitro. The in vivo differentiation of cells to form both teratomas and chimeras is a basic, yet reliable tool for assessing a cell's developmental potential. Several studies have demonstrated the ability of cultured pluripotent stem cells to generate all three embryonic germ layers (Takashima, et al., *Cell*, 158:1254-1269 (2014); Chan, et al., *Cell Stem Cell*, 13:663-675 (2013); Theunissen, et al., *Cell Stem Cell* 15:471-487 (2014); Evans, et al., *Nature*, 292: 154-156 (1981), Li, et al., *Cell*, 135:1299-1310 (2008); Buehr, et al., *Cell*, 135:1287-1298 (2008); and Thomson, et al., *Science*, 282:1145-1147 (1998). However, in vitro cultured pluripotent stem cells show limited/restricted cell potency as determined for example, by an inability to form chimeras, and/or generate extraembryonic lineages in vivo, limited developing potential as determined by their inability/inefficiency in forming chimeras and/or present with limitations with respect to the ability to rapidly expand the cells in vitro, stably maintaining the cells in culture, limiting the downstream application of these cells. For example, studies show that pluripotent cells such as naïve NHSM (naïve human stem cell medium)-hES (human embryonic stem) cells cannot contribute to both TE (trophectoderm) and ICM (inner cell mass) in chimeric mouse embryos (Gafni, et al., *Nature*, 504(7479):282-6 (2013)). Epiblast stem cells (EpiSCs) readily form teratomas, however, they rarely form chimeras. Han, et al., (*Cell*, 143:617-627 (2010)) describe a subpopulation of EpiSCs which make up about 99% (EpiSCs) in culture and show no chimera contribution. As a further example, poor survival of human embryonic stem cells after cell dissociation hinders further manipulation and development.

Thus, there is a need for methods to extend the cell potency of pluripotent stem cells in vivo, and methods to rapidly expand and stably maintained the cells in vitro.

It is therefore an object of the present invention to provide pluripotent stem cells with an extended cell potency in vivo.

It is also an object of the present invention to provide compositions for extending the cell potency of isolated pluripotent stem cells in vivo.

It is still an object of the present invention to provide methods of extending the cell potency of isolated pluripotent stem cells in vivo.

It is a further object of the present invention to provide methods of using pluripotent stem cells with extended cell potency.

SUMMARY OF THE INVENTION

Cocktails of factors have been identified which can be used to extend the cell potency of isolated pluripotent cells (isPSC) in vivo, following in vitro culture with the identified cocktail of factors, herein, chemical extenders of pluripotency (CEP). CEP extend the cell potency of isPSC for example, by conferring to the isPSC the ability to generate extraembryonic lineages in vivo, when compared to an untreated corresponding cell obtained from the same organism.

CEPS include: (1) a cytokine; (2) a glycogen synthase kinase (GSK) inhibitor; (3) a G protein coupled receptor inhibitor an acetylcholine receptor antagonist; and (4) a Poly(ADP-ribose) polymerase-1 (PARP1) inhibitor. In a preferred embodiment, the cytokine is Leukemia inhibitory factor (LIF) ("L"); the GSK inhibitor is the aminopyrimidine, CHIR99021 ("C") which has the chemical name [6-[[2-[[4-(2,4-Dichlorophenyl)-5-(5-methyl-1H-imidazol-2-yl)-2-pyrimidinyl]amino]ethyl]amino]-3-pyridinecarbonitrile]; the G protein coupled receptor inhibitor is an acetylcholine receptor antagonist, more preferably, mAChR (muscarinic acetylcholine receptor), for example, M2, DiM ((S)-(+)-Dimethindene maleate) ("D"); and the PARP1 inhibitor is MiH (Minocycline hydrochloride) ("M"). This preferred cocktail of CEP, herein LCDM, in effective amounts can be used to condition pluripotent cell in vitro, so as to extend their ability to generate embryonic and extraembryonic lineages.

Also provided is a method of extending the in vivo cell potency of an isolated pluripotent stem cell by reprogramming a donor cell using the CEP disclosed herein. The cell to be reprogrammed (i.e., the donor cell) is contacted with the CEPs for a sufficient period of time to reprogram the cell into a chemically induced/reprogrammed extended pluripotent stem cell (CiEPSC). In a preferred embodiment, cells are cultured initially in a reprogramming medium containing the CEPs for a period between 14-30 days. In some embodiments, the cells are cultured in medium containing a selective inhibitor of Rho-associated, coiled-coil containing protein kinase (ROCK), for example, Y27632 [(+)-(R)-trans-4-(1-aminoethyl)-N-(4-pyridyl)cyclohexanecarboxamide+++ dihydrochloride)], for a period of time ranging from 12 to 48 hrs, preferably from 24 to 48 hrs, most preferably, for 24 hours, prior to contacting the cells with CEPS. The ciEPSCs are isolated and can be further cultured. In this embodiment, the ROCK kinase inhibitor can be added to the cell culture medium during the first 12 hrs before and 12 hours after passaging. In other embodiments still, the ROCK inhibitor can be present in the cell culture medium during the first few passages, for example, 2-6, preferably, the first 3-5 passages.

Also disclosed are ciEPSC. A reprogrammed cell contacted with CEP as disclosed herein is identified as an extended pluripotent stem cell based on properties including: (i) morphologically, (ii) functionally: (a) the ability of the cell to differentiate into tissues of the three embryonic germ layers; (b) upregulated expression of one or more extraembryonic markers such as CDX2, GATA6, HAND1 and EOMES, (c) down regulation of one or markers for pluripotency such as OCT4, NANOG, KL2, SOX2, and UTF1(undifferentiated embryonic cell transcription factor); (d) upregulation of one or markers for pluripotency such as TBX3 and GBX2; and (e) the ability to form both embryonic and extraembryonic chimerism in vivo. The ciEPSC is different from a cell which has not been exposed to the CEPS disclosed herein in that it possesses at least one, preferably two, three, four or all of these properties, when compared to the non-CEPS treated cell. Upregulation or downregulation is determined by comparing the levels of the measured factor in the corresponding pluripotent stem cell from which the ciEPSC was obtained.

The ciEPSCs disclosed herein can be distinguished from human or mouse ESC or iPSC at least by the methods that are used to generate them i.e., by their origin. Where ESC are naturally occurring cells, ciEPSCs on the other hand are not naturally occurring (as evidenced by possession of characteristics which are not found in the corresponding naturally occurring ESC from which they are obtain), when ciEPSC are obtained by treating pluripotent cells with a combination of small molecules, as described herein.

The CEPSCs can be cultured or induced to differentiate into cells of a desired type. The CEPSCs and their progeny can be used in a number of applications, including but not limited to cell therapy and tissue engineering.

DETAILED DESCRIPTION OF THE INVENTION

Figure 1A:
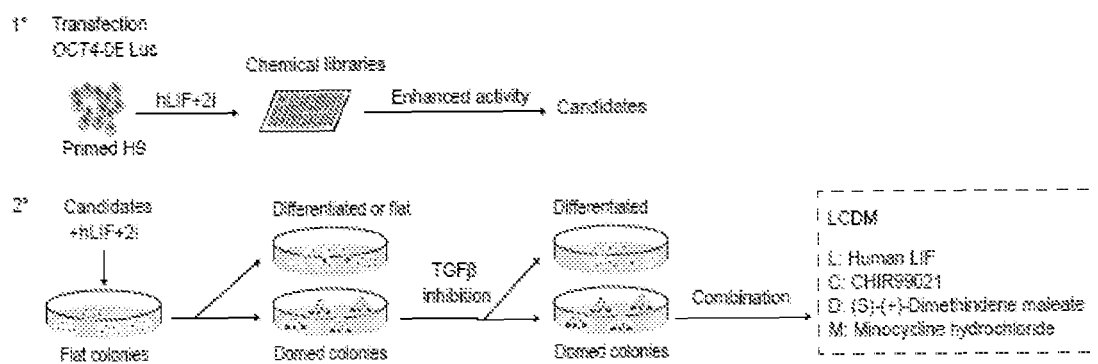
FIG. 1A is a schematic showing the strategies used for screening compounds.

Chemical cocktails that enable derivation of novel stem cells in human, termed extended pluripotent stem (EPS) cells, with improved/extended ability to generate both embryonic and extraembryonic lineages, has been identified. Importantly, a single human EPS (hEPS) cell has the ability to contribute to both embryonic and extraembryonic lineages (especially lineages in the placenta) in mouse chimeric embryos. As established by the studies described herein, hEPS cells showed upregulation of the basal mRNA activity of multiple extraembryonic genes when compared with primed human embryonic stem (primed hES) cells or naïve human ES cells supported by the NHSM (naïve human stem cell medium) condition (naïve NHSM-hES cells) (Gafni, et al., Nature, 504(7479):282-6 (2013)). Notably, hEPS cells could be generated by converting primed hES cells, somatic reprogramming, or directly from blastocysts. More importantly, pig EPS, rat EPS and mouse EPS (mEPS) cells were successfully established using the same culture conditions, and single mEPS cell can contribute to extraembryonic and embryonic tissues in chimeric conceptuses at embryonic day 10.5 (E10.5) and E12.5.

The studies described here demonstrate that the cell potency of in vitro cultured cells for example, pluripotent stem cells, can be extended in vivo beyond existing levels i.e., beyond the levels in a corresponding cell from the same organism which has not been contacted with the factors disclosed herein. Further, EPS cells can be rapidly expanded and stably maintained. Thus, EPS cells provide novel cell resources for disease modeling, for example, using humanized animal models studying early development, and generating patient-specific cells for regenerative medicine.

I. Definitions

The term "cell potency" as used herein a cell's ability to differentiate into other cell types. The more cell types a cell can differentiate into, the greater its potency.

The term "chemically induced pluripotent stem cells" (CiPSCs) as used herein refers to pluripotent cells derived from a cell that is not pluripotent, i.e., a multipotent or differentiated cell, by contacting the non-pluripotent cell with chemical compounds, not by expression of one or more transfected genes.

The term "chemically induced extended pluripotent stem cell ("ciEPSC")" as used herein refers to a pluripotent stem cell with an improved ability to generate extraembryonic lineages in vivo, when compared to the pluripotent stem cell type from which it is derived, by contacting a donor cell with chemical compounds. For example, a ciEPSC derived from primed human ESC shows an improved ability to generate extraembryonic tissue in vivo following contact with CEPS, when compared to non-CEPS-treated primed human embryonic stem cells.

The term "corresponding cell" is used to refer to a cell of the same type and from the same organism as the donor cell from which a ciEPSC is obtained. For example, the corresponding cell for a ciEPSC obtained from a mouse embryonic stem cell is a mouse embryonic stem cell which has not been contacted/reprogrammed with CEPS.

The term "donor cells" as used herein refers to cells that are to be contacted with the CEPS to induce/confer extended cell potency.

The term "extended cell potency" as used herein in connection with ciEPSC refers to the ability of a ciEPSC to differentiate into at least one cell type more that a corresponding cell.

The term "epigenetic" as used herein refers to covalent modifications of DNA that are not mutation based, but in some instances can still be passed from generation to generation. Genes that are activated or repressed without any change in DNA sequence are epigenetically controlled. Epigenetic modifications are stable, but potentially reversible alterations in gene expression that occur without permanent changes in DNA sequence. Many types of epigenetic processes have been identified—they include methylation, acetylation, phosphorylation, ubiquitylation, and sumolyation of histones as well as DNA methylation.

The term "Induced pluripotent stem cell" (iPSC), as used herein, is a type of pluripotent stem cell artificially derived from a non-pluripotent cell. CiPSCs are iPSCs; however, they differ from some iPSCs in that they are not genetically engineered to confer pluripotency.

The term "humanized animal model" is used herein to refer to a non-human mammal engrafted with functional human cells or tissues or expressing human transgenes.

"Improved ability to generate extraembryonic lineages in vivo" as used herein can be determined for example by measuring expression of a trophectoderm marker and/or contribution to both trophectoderm (TE) and ICM (inner cell mass) following microinjection in a chimeric assay as described herein under materials and methods.

The term "isolated" or "purified" when referring to ciEPSCs means chemically induced extended pluripotent stem cells at least 10%, 20% 30%, 35%, 40%, 45%, 50%, 55%, 60%, 65%, 70%, 75%, 80%, 85%, 90%, 95%, or 99% free of contaminating cell types which are not-extended pluripotent cells. The isolated EPSCs may also be substantially free of soluble, naturally occurring molecules.

"Media" and "culture medium" as used herein refers to the cell culture milieu. Media is typically an isotonic solution, and can be liquid, gelatinous, or semi-solid, for example, to provide a matrix for cell adhesion or support. Media, as used herein, can include the components for nutritional, chemical, and structural support necessary for culturing a cell.

The term "pluripotency" (or pluripotent), as used herein refers to a stem cell that has the potential to differentiate into any of the three germ layers: endoderm (for example, interior stomach lining, gastrointestinal tract, the lungs), mesoderm (for example, muscle, bone, blood, urogenital), or ectoderm (for example, epidermal tissues and nervous system). A multipotent stem cell is less plastic and more differentiated, and can become one of several types of cells within a given organ. For example, multipotent blood stem cells can develop into red blood cell progenitors, white blood cells or platelet producing cells. Adult stem cells are multipotent stem cells. Adipose-derived stem cells are multipotent.

"Pluripotent cell is used herein interchangeably with, "pluripotent stem cell".

"Reprogramming" as used herein refers to the conversion of a one specific cell type to another with additional/different functional and/or structural characteristics. For example, a cell that is not a ciEPSC as defined herein can be reprogrammed into a cell with extended ability of generate extraembryonic lineages in vivo, following in vitro culture.

The term "small molecule" refers to a molecule, such as an organic or organometallic compound, with a molecular weight of less than 2,000 Daltons, more preferably less than 1,500 Daltons, most preferably, less than 1,000 Daltons.

"Transforming growth factor beta (TGFβ) receptor inhibitor" as used herein refers to an agent that inhibits the TGFβ receptor. TGFβ receptors are single pass serine/threonine kinase receptors. Three TGF-β receptor types include receptor types I, II and III, i.e., TGF-β receptor 1, TGF-β receptor 2 and TGF-β receptor 3.

"2i" as use herein refers to ESC culture medium with dual inhibition of glycogen synthase kinase-3 and mitogen-activated protein kinase signaling, for example, ESC culture medium supplemented with 2i (CHIR99021 and PD0325901).

II. Compositions

Cocktails of factors have been identified which can be used to extend the cell potency of isolated pluripotent stem cells in vivo, following in vitro culture, herein, chemical extenders of pluripotency (CEP). CEP extend the cell potency of an isPSC for example, by conferring to the isPSC the ability to generate extraembryonic lineages in vivo when compared to an untreated corresponding cell. The CEP can be used to provide at an isolated population of ciEPSC containing least 10%, 20% 30%, 35%, 40%, 45%, 50%, 55%, 60%, 65%, 70%, 75%, 80%, 85%, 90%, 95%, or 99% free of contaminating cell types such as non-extended pluripotent cells.

Figure 4A:
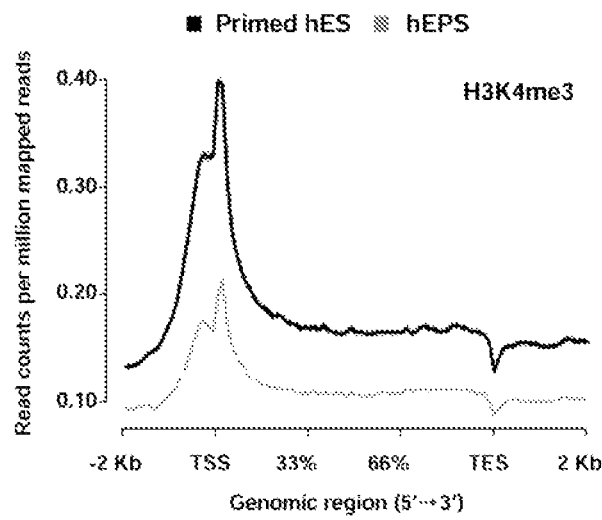
FIGS. 4A and 4B show the profiles of H3K4me3 and H3K27me3 chromatin marks over all genes in primed hES (n=2, technical replicates) and hEPS (n=2, technical replicates) cells. The standard error of mean (SEM) across the regions is calculated and shown as a semi-transparent shade around the mean curve.
Figure 4B:
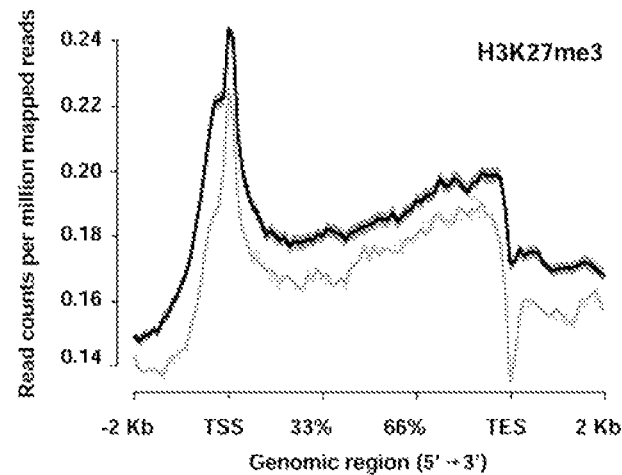
Figure 4C:
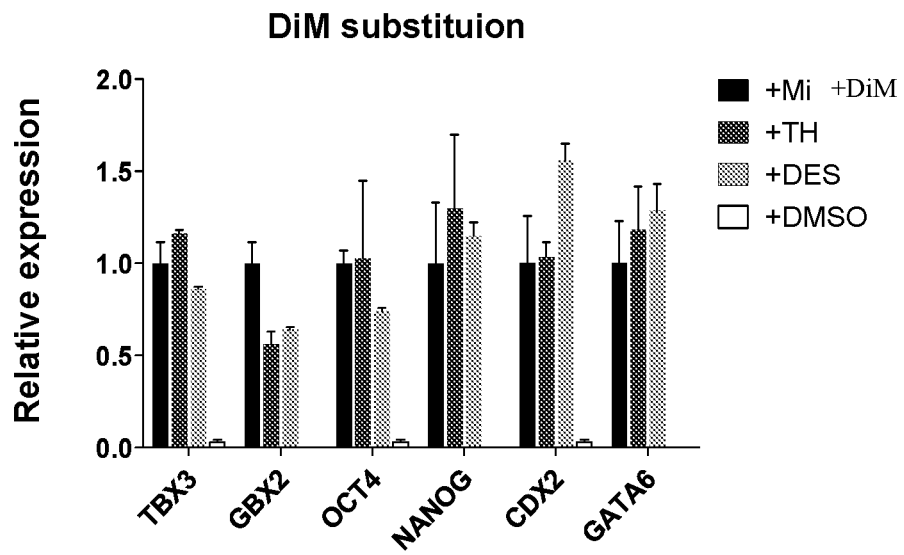
FIGS. 4C-D are bar graphs showing Q-PCR analysis of selected gene expression in hEPS cells under different conditions at passage 7. DiM (((S)-(+)-Dimethindene maleate) (FIG. 4C) and MiH (Minocycline hydrochloride) (FIG. 4D) were replaced with small molecules targeting to the same targets in the LCDM [hLIF (human leukemia inhibitory factor), CHIR99021, DiM, and MiH] condition. hEPS cells were cultured under LCM condition with an added small molecule selected from: DiM (2 μM), TH(5 μM), DES(5 μM), or cultured with DMSO (dimethyl sulfoxide) respectively (FIG. 4C) or under LCD condition with an added small molecule selected from MiH, BSI-201 (5 μM), NAM (100 μM), PJ34 (N-(6-Oxo-5,6-dihydro-phenanthridin-2-yl)-N,N-dimethylacetamide. HCl) (5 μM), or DMSO (FIG. 4D). Expression values are normalized to the mean value of the LCM+DiM (FIG. 4C) and LCD+MiH (FIG. 4D) sample. LCM: human LIF+ CHIR99021+MiH; LCD: human LIF+CHIR99021+DiM. Center values indicate mean. Error bars indicate s.d. (n=3, technical replicates). TH: Tripelennamine HCL; DES: Desloratadine; BSI: BSI-201; NAM: Nicotinamide.

CEPS include: (1) a cytokine; small molecules, including (1) a glycogen synthase kinase (GSK) inhibitor; (2) a G protein coupled receptor inhibitor an acetylcholine receptor antagonist; and (3) a Poly(ADP-ribose) polymerase-1 (PARP1) inhibitor. The compositions include CEPs in effective amounts to reprogram pluripotent cells preferably in vitro, into cell with an extended/enhanced ability to generate embryonic and extraembryonic lineages, when compared to pluripotent cells from the donor pluripotent cell. It is within the abilities of one of ordinary skill in the art to determine an equivalent effective concentration for other members within the group of cytokines, GSK inhibitor, GPCR antagonist, or PARP1 inhibitor based on the effective concentrations disclosed for specific species within the genus, using an in vitro assay, for example, as exemplified herein in experiments substituting MiH or DIM with small molecules of similar activity (FIGS. 4C and D).

An optional compound useful in the methods disclosed herein is a selective inhibitor of Rho-associated, coiled-coil containing protein kinase (ROCK), for example, Y27632 [(+)-(R)-trans-4-(1-aminoethyl)-N-(4-pyridyl)cyclohexanecarboxamide+++dihydrochloride)], in a concentration ranging from 0.5 to 20 preferably from 5-15 most preferably, 10 µM or fasudil in an equivalent concentration.

An even more preferred embodiment includes at least one small molecule that can stabilize Axin-beta catenin complex. Preferred molecules include endo-IWR1 (4-[(3aR,4S,7R,7aS)-1,3,3a,4,7,7a-hexahydro-1,3-dioxo-4,7-methano-2H-isoindol-2-yl]-N-8-quinolinyl-benzamide; CAS No. 1127442-82-3) and XAV939 (3,5,7,8-Tetrahydro-2-[4-(trifluoromethyl)phenyl]-4H-thiopyrano[4,3-d]pyrimidin-4-one; CAS No. 284028-89-3).

A. Chemical Extenders of Pluripotency

1. Cytokines

A preferred cytokine is human Leukemia inhibitory factor (LIF) ("L"), an interleukin 6 class cytokine, used in a concentration range from 1-100 ng/ml, preferably from 1-50 and even more preferably, from 1 to 30 ng/ml. IL-6 is a prototypical four-helix bundle cytokine that is the founder member of the neuropoietins, a group of cytokines structurally related, that include IL-6, IL-11, IL-27, IL-31, leukemia inhibitory factor, oncostatin M, cardiotrophin-1, neuropoietin and cardiotrophin-like cytokine factor 1 (also known as new neurotrophin 1 and B cell stimulatory factor-3), and two viral analogs of IL-6. These members of the interleukin 6 family of cytokines can be used in the compositions disclosed herein, at equivalent concentrations disclosed for LIF.

2. Small Molecules

Chemical compounds that extend pluripotency i.e., chemical extenders of pluripotency (CEP) include small molecules having a molecular weight of less than 2,000 Daltons, more preferably less than 1,500 Daltons, most preferably less than 1,000 Dalton, alone or in combination with proteins. The small molecules may have a molecular weight less than or equal to 900 Daltons or, less than or equal to 500 Daltons. Larger molecules can be used in chemically-induced reprogramming, preferably targeting the same pathway as the small molecules identified here.

(i) PARP1 Inhibitors

The PARP1 inhibitor is preferably MiH (Minocycline hydrochloride) ("M"), a potent PARP1 selective inhibitor, used in a concentration ranging from 0.5-5 µM, more preferably from. For example, the concentration of MiH in the composition can be 0.5, 1, 1.5, 2, 2.5, 3, 3.5, 4, 4.5, 5 or 5 µM. Additional PARP1 inhibitors include, but are not limited to BSI-201 (4-iodo-3-nitrobenzamide), NAM (Nicotinamide), and PJ34 (N-(6-Oxo-5,6-dihydro-phenanthridin-2-yl)-N,N-dimethylacetamide (a pPARP1 and PARP2 inhibitor); PARP Inhibitor XIV; 4-[(1-Methyl-1H-pyrrol-2-yl)methylene]-1,3(2H,4H)-isoquinolinedione (a potent PARP1 inhibitor); Veliparib; 2-[(2R)-2-Methylpyrrolidin-2-yl]-1H-benzimidazole-4-carboxamide dihydrochloride (a potent PARP-1 and PARP-2 inhibitor); Olaparidb (1-(Cyclopropylcarbonyl)-4-[5-[(3,4-dihydro-4-oxo-1-phthalazinyl)methyl]-2-fluorobenzoyl]piperazine); 6-amino-1H-benz[de]isoquinoline-1; and INH2BP (5-Iodo-6-amino-1,2-benzopyrone; PARP Inhibitor II). Other known PARP inhibitors including PARP1 and/or PARP2 inhibitors are commercially available and can be included in the CEP compositions disclosed herein in an effective amount to reprogram cells into ciEPSC. It is within the abilities of one of ordinary skill in the art to determine an equivalent concentration for other PARP1 Inhibitors using an in vitro assay, for example, as exemplified herein in experiments substituting MiH with TH and DES or DIM with NAM, etc.

(ii) GSK Inhibitor

The GSK inhibitor preferably inhibits GSK3 and preferably, is selective for GSK3. A suitable GSK inhibitor is the aminopyrimidine, CHIR99021 ("C"), which is the glycogen synthase kinase 3 inhibitor. The CEP compositions include CHIR99021 in a concentration range from 0.1 to 5 µM, preferably between 1 and 3, and even more preferably, between 1.5 and 3 µM. For example, the CEP can include CHIR99021 in concentrations of 1, 1.5, 2, 2.5, 3, 3.5, 4, 4.5, or 5 µM. Concentrations that fall between these numbers are contemplated, as one of ordinary skill in the art can readily fine tune the effective amounts needed.

However, other GSK inhibitors are commercially available and are can be used in the compositions disclosed herein. Examples include, but are not limited to BIO-acetoxime; GSK 3I inhibitor XV; SB-216763; CHIR 99021 trihydrochloride, which is the hydrochloride salt of CHIR99021; GSK-3 Inhibitor IX [((2Z, 3E)-6'-bromo-3-(hydroxyimino)-[2,3'-biindolinylidene]-2'-one]; GSK 3 IX [6-Bromoindirubin-3'-oxime]; GSK-3β Inhibitor XII [3-[[6-(3-Aminophenyl)-7H-pyrrolo[2,3-d]pyrimidin-4-yl]oxy]phenol]; GSK-3 Inhibitor XVI [6-(2-(4-(2,4-dichlorophenyl)-5-(4-methyl-1H-imidazol-2-yl)-pyrimidin-2-ylamino)ethyl-amino)-nicotinonitrile]; SB-415286 [3-[(3-chloro-4-hydroxyphenyl)amino]-4-(2-nitrophenyl)-1H-pyrrole-2,5-dione]; and Bio [(2'Z,3'E)-6-bromoindirubin-3'-oxime].

(iii) G Protein Coupled Receptor (GPCR) Inhibitors

The most preferred GPCR inhibitor is (S)-(+)-Dimethindene maleate ("D") used in a concentration range from 1-5 Dimethindene maleate is an enantiomer that is a subtype-selective mAChR (muscarinic acetylcholine receptor) M2, mAChR M1, mAChR M3 and mAChR M44 antagonist as well as a histamine $H_1$ receptor antagonist. However, other GPCR inhibitors can be included in the CEP compositions disclosed herein, and they include, but are not limited to ethylenediamines, for example, Tripelennamine HCL, (a histamine H1 antagonist, which competitively blocks central and peripheral histamine H1 receptorss), mepyramine, and antazoline; tricyclics or tetracyclics such as loratidine, or its metabolite, Desloratadine (selective histamine H1 antagonist). Others are known in the art, and include, but are not limited to levocetirizine, fexofenadine, Astemizole, Ketotifen, Cetirizine, Loratadine, Rupatadine, Mizolastine, Acrivastine, Ebastine, Bilastine, Bepotastine, Terfenadine, Quifenadine, cyclizine, chlorcyclizine, hydroxine, peniramine, chlorphenamine, tripolidine, diphenhydramine, carbinoxamine, bromazine, etc.

A particularly preferred cocktail includes a combination of: (1) a cytokine; small molecules, including (1) a glycogen synthase kinase (GSK) inhibitor; (2) a G protein coupled receptor inhibitor an acetylcholine receptor antagonist; (3) a Poly(ADP-ribose) polymerase-1 (PARP1) inhibitor; ROCK inhibitor and small molecule that can stabilize Axin-beta catenin complex. In this embodiment, the cocktail preferably includes: LCDM plus endo-IWR1 (at a preferred concentration range of 0.5-10 µM) and Y27632 (at a preferred concentration range of 2-5 µM), or LCDM plus XAV939 (at a preferred concentration range of 0.5-10 µM) and Y27632 (2-5 µM).

B. Cells to be Induced (Donor Cells)

The extended pluripotent stem cells are obtained by inducing pluripotent cells, or partially or completely differentiated cells obtained from a mammal such as any mammal (e.g., bovine, ovine, porcine, canine, feline, equine, primate), preferably a human. Sources include bone marrow, fibroblasts, fetal tissue (e.g., fetal liver tissue), peripheral blood, umbilical cord blood, pancreas, skin or any organ or tissue.

In a preferred embodiment the ciEPSC are obtained from pluripotent cells, for example, embryonic stem cells or induced pluripotent stem cells (iPSCs). The iPSCs include cells obtained by genetic engineering and/or pure chemical reprogramming. In other embodiments, ciEPSC are obtained from blactocyts.

Preferably, the iPSCs are obtained from chemically induced fibroblasts, adipose-derived stem cells, neural stem cells or cells from the intestinal epithelium. In some embodiment, CiPSCs are obtained from chemically induced neonatal (for example foreskin) or adult fibroblasts. However, iPSCs can be obtained from other cell types including but not limited to: multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells.

Pluripotent cells that can be used in the methods disclosed herein are known in the art and have been described, including methods of maintaining the cells in culture. Mouse embryonic stem (ES) cells are isolated from the inner cell mass of blastocysts, and can be preserved in vitro in a naive inner-cell-mass-like configuration by providing exogenous stimulation with leukaemia inhibitory factor (LIF) and small molecule inhibition of ERK1/ERK2 and GSK3β signaling (termed 2i/LIF conditions). Hallmarks of naive pluripotency include driving Oct4 (also known as Pou5f1) transcription by its distal enhancer, retaining a pre-inactivation X chromosome state, and global reduction in DNA methylation and in H3K27me3 repressive chromatin mark deposition on developmental regulatory gene promoters. Upon withdrawal of 2i/LIF, naive mouse ES cells can drift towards a primed pluripotent state resembling that of the post-implantation epiblast. Although human ES cells share several molecular features with naive mouse ES cells, they also share a variety of epigenetic properties with primed murine epiblast stem cells (EpiSCs). These include predominant use of the proximal enhancer element to maintain OCT4 expression, pronounced tendency for X chromosome inactivation in most female human ES cells, increase in DNA methylation and prominent deposition of H3K27me3 and bivalent domain acquisition on lineage regulatory genes. Derivation of genetically unmodified human naive pluripotent stem cells from already established primed human ES cells, from somatic cells through induced pluripotent stem (iPS) cell reprogramming or directly from blastocysts is disclosed in Gafni, et al., *Nature*, 504(7479):282-286 (2013).

Donor cells may be isolated by disaggregating an appropriate organ or tissue which is to serve as the cell source using techniques known to those skilled in the art. For example, the tissue or organ can be disaggregated mechanically and/or treated with digestive enzymes and/or chelating agents that weaken the connections between neighboring cells, so that the tissue can be dispersed to form a suspension of individual cells without appreciable cell breakage. Enzymatic dissociation can be accomplished by mincing the tissue and treating the minced tissue with one or more enzymes such as trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators.

C. Chemically Induced Extended Pluripotent Stem Cells (ciEPSCs)

CiEPSC are identified as an extended pluripotent cell based on properties including: (i) morphologically-mouse ESC-like morphology, and (ii) functionally based on: (a) the ability of the cell to differentiate into tissues of the three embryonic germ layers; (b) upregulated expression of one or more extraembryonic markers, (c) Up and/or down regulation of one or markers for pluripotency; and (d) contributing in vivo to both TE and ICM. ciEPSCs show extended cell potency in vivo when compared to a corresponding cell. In a preferred embodiment, the ciEPSCs generate/contribute to one or more extraembryonic lineages in vivo. ciEPSC contribution to one or more lineages in vivo can be determined by determining the presence of one or more markers of extraembryonic markers (discussed below), following in vivo transplantation using methods known in the art, and as described in the examples.

1. Morphology ciEPSCs obtained from a human donor cell morphologically resemble mouse embryonic stem (ES) cells. Human EPS cells form dome-shaped colonies which resemble mouse embryonic stem cells. Mouse EPS cells are morphologically the same as mouse embryonic stem cells.

2. Ability to Differentiate into Tissues of the Three Germ Layers ciEPSCs have the ability to differentiate into one or more cells/tissues from each of the three germ layers, the ectoderm, mesoderm and endoderm, using methods known in the art.

The ectoderm generates the outer layer of the embryo, and it forms from the embryo's epiblast. The ectoderm develops into the surface ectoderm, neural crest, and the neural tube. The surface ectoderm develops the epidermis, hair, nails, lens of the eye, sebaceous glands, cornea, tooth enamel, the epithelium of the mouth and nose. The neural crest of the ectoderm develops into: peripheral nervous system, adrenal medulla, melanocytes, facial cartilage. The neural tube of the ectoderm develops into: brain, spinal cord, posterior pituitary, motor neurons, and retina.

The endoderm consists at first of flattened cells, which subsequently become columnar. It forms the epithelial lining of the whole of the digestive tube except part of the mouth and pharynx and the terminal part of the rectum (which are lined by involutions of the ectoderm). It also forms the lining cells of all the glands which open into the digestive tube, including those of the liver and pancreas; the epithelium of the auditory tube and tympanic cavity; the trachea, bronchi, and air cells of the lungs; the urinary bladder and part of the urethra; and the follicle lining of the thyroid gland and thymus. The endoderm forms: the stomach, the colon, the liver, the pancreas, the urinary bladder, the epithelial parts of trachea, the lungs, the pharynx, the thyroid, the parathyroid, and the intestines.

The mesoderm forms connective tissue, muscle (smooth and striated), the lymphatic system, bone, serous membranes, cartilage, adipose tissue, circulatory system, dermis, genitourinary system, and notochord.

3. Contributing In Vivo to Both TE and ICM/Upregulation of Extraembryonic Markers The ability to contribute in vivo to both TE and ICM where a corresponding cell cannot so contribute is an indicia of improved ability to generate/contribute to extraembryonic lineages in vivo. For example, the cell potency of a human embryonic stem (hES) cell which can differentiate into one or more cells/tissues from each of the three germ layers is improved/extended by conferring to the hES contacted with CEPS as disclosed herein, the ability to contribute to both TE and ICM, in vivo. The ability of cells to contribute to TE and ICM in vivo can be determined using methods known in the art. In some embodiments the ability to contribute to TE and ICM is determined by microinjecting ciEPSCs into mouse E2.5 or E3.5 embryos and allowed to develop into E10.5 embryos in vivo and determining the contribution of injected cells to TE and ICM as disclosed in the examples.

ciEPSCs show upregulated expression of one or more extraembryonic markers such as CDX2, GATA6, HAND1 and EOMES, when compared to untreated in vitro cultured corresponding cells isolated from the corresponding organism. For example, if generated from primed hESC, the ciEPSC shows upregulation of one or more extraembryonic markers when compared to primed hESC; if generated from naïve hESC, the ciEPSC shows upregulation of one or more extraembryonic markers when compared to naive hESC, etc. Upregulation of one or more extraembryonic markers is an indication of improved ability to generate extraembryonic lineages in vivo. In a preferred embodiment, the mRNA basal activity of extraembryonic genes is upregulated in CiEPSC.

4. Up and/or Down Regulation of Markers of Pluripotency ciEPSCs show upregulation of one or markers for pluripotency such as TBX3 and GBX2, when compared to untreated corresponding cells (i.e., corresponding cells that are not contacted with CEPS as disclosed herein) isolated from the corresponding organism. The mRNA expression of several pluripotency marker genes, including OCT4, REX1, DPPA3, TBX3, and GBX2, was more homogenous in hEPS cells than that in non-CEP-treated primed hES cells.

ciEPSCs show down regulation of one or markers for pluripotency such as OCT4, NANOG, KL2, SOX2, and UTF1 (undifferentiated embryonic cell transcription factor), when compared to untreated corresponding cells isolated from the same organism. This is in contrast to iPSCS, for example, the cells disclosed in Hou, et al., *Science*, 341 (6146):651-4 (2013), which show upregulation of markers such as NANOG, UTF1 and SOX2.

The ciEPSC is different from an untreated corresponding in vitro cultured cell in that it possesses at least one, preferably two, three, four or all of these properties, when compared to the non-CEPS treated corresponding cell. For example, a ciEPSC possesses the morphology disclosed herein, it has the ability to differentiate into one or more cells/tissues from all three germ layers, and it shows upregulation of one or more extraembryonic markers, or additionally, it can contribute in vivo to both TE and ICM, or additionally, it shows up and/or down regulation of one or more markers of pluripotency as disclosed herein. For example, compared with mouse embryonic stem cells culture in the 2i condition, mouse EPS cells show to contribute to both embryonic and extraembryonic (especially placenta) chimerism in vivo, down regulation of the protein expression of OCT4, downregulation of the repressive epigenetic marker H3K27me3 in the locus of extraembryonic genes such as Cdx2 and Eomes. Additional characteristic such as LIF signaling and/or GSK3β phosphorylation can be used to further identify and distinguish cells as ciEPSC. For example, when compared to primed hES cells, hEPS cells show activation of LIF signaling, which can be determined for example measuring the levels of GP130, STAT3 and -p-STAT3. In addition, GSK3β phosphorylation is decreased in hEPS cells when compared to hES. Activation of LIF signaling and the level of GSK3β signaling can be used to further identify ciEPSC obtained from any organism and distinguish the ciEPSC from other isolated pluripotent stem cells.

Additional genes upregulated in hEPS cells compared to primed hPSCs, include HOXA1 (Homeobox A1), MIXL1 (Mix1 homeobox-like 1), and DERA (deoxyribose-phosphate aldolase) genes. Genes exclusively upregulated in hEPS cells but not other hPSC types, include for example, CHD7(Chromodomain Helicase DNA Binding Protein 7)), CHD4(Chromodomain Helicase DNA Binding Protein 4), MIXL1 and LEF1 (Lymphoid enhancer-binding factor 1).

III. Methods of Making

A. Induction of Extended Pluripotency in Pluripotent Stem Cells ciEPSCs are produced by contacting cells to be induced/reprogrammed (herein donor cells) with culture media containing the CEPs for a sufficient period of time to result in reprogramming the cells into chemically induced extended pluripotent stem cell (ciEPSC).

A donor cell is contacted with the CEPs disclosed herein in an amount effective to induce and/or enhance reprogramming of the cell into an extended pluripotent stem cell. One of skill in the art can readily determine the concentrations of the CEP compounds disclosed herein required to provide complete reprogramming, by using methods outlined in the examples below, or other methods known in the art. In a preferred embodiment, the donor is a pluripotent stem cell, for example as embryonic stem cells or induced pluripotent stem cells (iPSCs). The iPSCs include cells obtained by genetic engineering and/or pure chemical reprogramming. In other embodiments, ciEPSC are obtained from blactocyts.

In an exemplary method where the donor cells are primed human embryonic stem cells (hESC), the cells can be seeded onto feeder cells as single cells or as small colonies. hESC are preferably cultured on conventional hES culture medium for 3 to 6 days, for example, for 3 days, 4 days, 5 days, or 6 days after the last passage, before contact with the CEPS. In embodiments where the cells are seeded as single cells, a selective inhibitor of Rho-associated, coiled-coil containing protein kinase (ROCK) inhibitor, for example, Y27632 is optionally added to the culture medium 12 to 48 hrs, preferably from 24 to 48 hrs, most preferably, for 24 hours, before conversion, in a concentration range from 5-20 μM, preferably, 5-15 μM and more preferably, 10 μM. In this embodiment, the ROCK kinase inhibitor can be added to the cell culture medium during the first 12 hrs before and 12 hours after passaging. In other embodiments still, the ROCK inhibitor can be present in the cell culture medium during the first few passages, for example, 2-6, preferably, the first 3-5 passages.

The cells are cultured in CEPS, preferably LCDM in the concentrations disclosed herein for 1-5 passages, preferably 3-5, a time frame which is effective to induce extended pluripotency determined morphologically and functionally as disclosed herein.

For cells that require 3-4 days in culture before passaging, this time frame translates into 3-20 days, most preferably, 9-20 days culture in LCDM. In some embodiments, the donor cell is a naïve ESC. In these embodiments, the cells can be contacted with LCDM 12 or 24 hours following seeding. In other embodiments, the donor cells are provided as blastocyst. In these embodiments, the blastocysts are seeded using conventional methods known in the art, following which the cells are cultured in cell culture medium containing LCDM (preferably, after the zona pellucid is removed) for a period ranging from 4-7 days, after which initial outgrowths are visible. For example, the blastocyst can be cultured in LCDM for 4 days, 5 day, 6 days or 7 days before initial outgrowth are visible.

Culture in LCDM is continued for a time effective to induce extended pluripotency as disclosed herein. In some preferred embodiments the cells are cultured in LCDM for at least 10 passages (about 40 days). Cultured blastocysts can be dissociation into small pieces or single cells, reseeding on feeder cells, and passaging using a using for example, trypsin-EDTA. The newly established cell line is maintained using the method disclosed herein for culturing EPSC.

Resultant cells are identified as ciEPSC morphologically and functionally, using characteristics such as the ability of the cell to differentiate into tissues of the three embryonic germ layers; (b) upregulated expression of one or more extraembryonic markers such as CDX2, GATA6, HAND1 and EOMES, (c) down regulation of one or markers for pluripotency such as OCT4, NANOG, KL2, SOX2, and UTF1(undifferentiated embryonic cell transcription factor); (d) upregulation of one or markers for pluripotency such as TBX3 and GBX2; and (e) the ability to form chimeric embryos.

In some embodiments for generating EPS cells from somatic cells such as fibroblasts, somatic cells can be directly induced into EPS cells by culturing the cells in LCDM for a period of time sufficient to obtain domed colonies, which are further expanded in LCDM condition as described herein.

B. Isolation of ciEPSCs

A substantially purified population of ciEPSCs can be obtained, for example, by extraction (e.g., via density gradient centrifugation and/or flow cytometry) from a culture source. Purity can be measured by any appropriate method. The pluripotent cells can be 99%-100% purified by, for example, flow cytometry (e.g., FACS analysis). Human induced extended pluripotent stem cells can be isolated by, for example, utilizing molecules (e.g., antibodies, antibody derivatives, ligands or Fc-peptide fusion molecules) that bind to a marker or a combination of markers on the induced pluripotent stem cells and thereby positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Antibodies may be conjugated with markers, such as magnetic beads, which allow for direct separation, biotin, which can be removed with avidin or streptavidin bound to a support, or fluorochromes, which can be used with fluorescence activated cell sorter, to allow for ease of separation of the particular cell type. Any technique may be employed which is not unduly detrimental to the viability of the induced pluripotent stem cells. In one embodiment, the cells are incubated with an antibody against a marker (e.g., a TRA-1-81 antibody) and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest, the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, and Texas red.

C. Culture and Preservation of ciEPSCs (and their Progeny)

The ciEPSCs can be expanded in culture and stored for later retrieval and use. Once a culture of cells or a mixed culture of stem cells is established, the population of cells is mitotically expanded in vitro by passage to fresh medium as cell density dictates under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor). Cultured cells can be transferred to fresh medium when sufficient cell density is reached.

In a preferred embodiment, cell culture medium for maintaining ciEPSC is for example, N2B27 medium, supplemented with CEPS disclosed herein, preferably, LCDM, at the same concentrations used to induce extended pluripotency i.e., the CEPs disclosed herein are used to extend pluripotency in a cell, and to maintain the extended pluripotency. For example, the cell culture medium for maintaining ciEPSC can b N2B27 medium (without BSA), N2B27 medium (without BSA) supplemented with 5% KSR (Knockout serum replacement). Other basal media can also be used, for example, DF12 medium supplemented with 20% KSR. These basal media are supplemented with CEPs as disclosed above. According to some embodiments of the invention, the LCDM can maintain ciEPSCs the undifferentiated and extended pluripotent state 2 to over 100 passages in culture. For example, the LCDM can maintain ciEPSCs in the undifferentiated and extended pluripotent for 2, passages. 3, 4, 5, 6, 7, 8, 9 or 10 passaged in culture, preferably, for more than 10 passages, for example for about 20 passages in culture, e.g., for at least about 25, about 30, about 35, about 40, about 45, about 50, about 55, about 60, about 65, about 70, about 75 and about 80 passages while in culture. In a preferred embodiment, the ciEPSCs maintain a normal karyotype during the 2, 3, 4, 5, 6, 7, 8, 9, 10, more than 10, for example, about 20 passages in culture, e.g., for at least about 25, about 30, about 35, about 40, about 45, about 50, about 55, about 60, about 65, about 70, about 75 and about 80 passages while in culture. In some embodiments, the cell culture medium for promoting CiEPSCs proliferation and single-colony formation include ROCK inhibitor at a low concentration for example, Y27632 at 2-5 µM.

Cells can be cryopreserved for storage according to known methods, such as those described in Doyle et al., (eds.), 1995, Cell & Tissue Culture: Laboratory Procedures, John Wiley & Sons, Chichester. For example, cells may be suspended in a "freeze medium" such as culture medium containing 15-20% fetal bovine serum (FBS) and 10% dimethylsulfoxide (DMSO), with or without 5-10% glycerol, at a density, for example, of about $4\text{-}10\times10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years.

IV. Methods of Use

Identification of a readily available source of stem cells that can give rise to a desired cell type or morphology is important for therapeutic treatments, tissue engineering and research. The availability of stem cells would be extremely useful in transplantation, tissue engineering, regulation of angiogenesis, vasculogenesis, organ regeneration, humanized animal models, cell replacement or cell therapies as well as the prevention of diseases, etc. Such stem cells can also be used to introduce a gene into a subject as part of a gene therapy regimen.

A. Providing Differentiated Somatic Cells (Re-Differentiated Cells)

Once established, a culture of stem cells may be used to produce progeny cells, for example, fibroblasts capable of producing new tissue. The ciEPSCs can be induced to differentiate into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells, blood cells, retinal cells (and other cells involved in sensory perception, such as those that form hair cells in the ear or taste buds on the tongue), and nervous tissue including nerves.

In one embodiment, the ciEPSCs are induced to differentiate into cells of ectodermal origin by exposing the cells to an "ectodermal differentiating" media. In another embodiment the ciEPSCs are induced to differentiate into cells of mesodermal origin by exposing the cells to "mesodermal differentiating media". In still another embodiment, the ciEPSCs are induced to differentiate into cells of endodermal origin by exposing the cells to "endodermal media". Components of "endodermal", "mesodermal" and "ectodermal" media are known to one of skill in the art. Known cell surface markers can be used to verify that the cells are indeed differentiating into cells of the lineage of the corresponding cell culture medium. The most commonly accepted markers to confirm differentiation of the three germ layers are the expression of alpha fetal protein for endodermal cells, alpha smooth muscle actin for mesoderm, and Beta-III tubulin for ectoderm, all of which are normally expressed very early in the development of these tissues.

Differentiation of stem cells to fibroblasts or other cell types, followed by the production of tissue therefrom, can be triggered by specific exogenous growth factors or by changing the culture conditions (e.g., the density) of a stem cell culture. Methods for inducing differentiation of cells into a cell of a desired cell type are known in the art. For example, ciEPSCs can be induced to differentiate by adding a substance (e.g., a growth factor, enzyme, hormone, or other signaling molecule) to the cell's environment. Examples of factors that can be used to induce differentiation include erythropoietin, colony stimulating factors, e.g., GM-CSF, G-CSF, or M-CSF, interleukins, e.g., IL-1, -2, -3, -4, -5, -6, -7, -8, Leukemia Inhibitory Factory (LIF), or Steel Factor (Stl), coculture with tissue committed cells, or other lineage committed cells types to induce the stem cells into becoming committed to a particular lineage.

The redifferentiated cells can be can be expanded in culture and stored for later retrieval and use.

B. Cell Therapy

Therapeutic uses of the induced pluripotent stem cells include transplanting the induced pluripotent stem cells, stem cell populations, or progeny thereof into individuals to treat a variety of pathological states including diseases and disorders resulting from cancers, wounds, neoplasms, injury, viral infections, diabetes and the like. Treatment may entail the use of the cells to produce new tissue, and the use of the tissue thus produced, according to any method presently known in the art. The cells may be implanted, injected or otherwise administered directly to the site of tissue damage so that they will produce new tissue in vivo. In one embodiment, administration includes the administration of genetically modified ciEPSCs or their progeny.

In a preferred embodiment, the ciEPSCs are obtained from autologous cells i.e., the donor cells are autologous. However, the cells can be obtained from heterologous cells. In one embodiment, the donor cells are obtained from a donor genetically related to the recipient. In another embodiment, donor cells are obtained from a donor genetically un-related to the recipient.

If the human ciEPSCs are derived from a heterologous (non-autologous/allogenic) source compared to the recipient subject, concomitant immunosuppression therapy is typically administered, e.g., administration of the immunosuppressive agent cyclosporine or FK506. However, due to the immature state of the human induced pluripotent stem cells such immunosuppressive therapy may not be required. Accordingly, in one embodiment, the human induced pluripotent stem cells can be administered to a recipient in the absence of immunomodulatory (e.g., immunsuppressive) therapy. Alternatively, the cells can be encapsulated in a membrane, which permits exchange of fluids but prevents cell/cell contact. Transplantation of microencapsulated cells is known in the art, e.g., Balladur et al., *Surgery*, 117:189-94, 1995; and Dixit et al., *Cell Transplantation* 1:275-79 (1992).

(i) Diabetes

Diabetes mellitus (DM) is a group of metabolic diseases where the subject has high blood sugar, either because the pancreas does not produce enough insulin, or, because cells do not respond to insulin that is produced. A promising replacement for insulin therapy is provision of islet cells to the patient in need of insulin. Shapiro et al., *N Engl J Med.*, 343(4):230-8 (2000) have demonstrated that transplantation of beta cells/islets provides therapy for patients with diabetes. Although numerous insulin types are commercially available, these formulations are provided as injectables. The human induced pluripotent stem cells provide an alternative source of islet cells to prevent or treat diabetes. For example, induced pluripotent stem cells can be isolated and differentiated to a pancreatic cell type and delivered to a subject. Alternatively, the induced pluripotent stem cells can be delivered to the pancreas of the subject and differentiated to islet cells in vivo. Accordingly, the cells are useful for transplantation in order to prevent or treat the occurrence of diabetes. Methods for reducing inflammation after cytokine exposure without affecting the viability and potency of pancreatic islet cells are disclosed for example in U.S. Pat. No. 8,637,494 to Naziruddin, et al.

(ii) Neurodegenerative Disorders

Neurodegenerative disorders are characterized by conditions involving the deterioration of neurons as a result of disease, hereditary conditions or injury, such as traumatic or ischemic spinal cord or brain injury. Neurodegenerative conditions include any disease or disorder or symptoms or causes or effects thereof involving the damage or deterioration of neurons. Neurodegenerative conditions can include, but are not limited to, Alexander Disease, Alper's Disease, Alzheimer Disease, Amyotrophic Lateral Sclerosis, Ataxia Telangiectasia, Canavan Disease, Cockayne Syndrome, Corticobasal Degeneration, Creutzfeldt-Jakob Disease, Huntington Disease, Kennedy's Disease, Krabbe Disease, Lewy Body Dementia, Machado-Joseph Disease, Multiple Sclerosis, Parkinson Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes *Dorsalis* or any other condition associated with damaged neurons. Other neurodegenerative conditions can include or be caused by traumatic spinal cord injury, ischemic spinal cord injury, stroke, traumatic brain injury, and hereditary conditions.

In particular, the disclosed methods include transplanting into a subject in need thereof NSCs, neural progenitors, or neural precursors that have been expanded in vitro such that the cells can ameliorate the neurodegenerative condition. Transplantation of the expanded neural stem cells can be used to improve ambulatory function in a subject suffering from various forms of myelopathy with symptoms of spasticity, rigidity, seizures, paralysis or any other hyperactivity of muscles. Methods for expanding and transplanting neural cells and neural progenitor cells for the treatment of different neurodegenerative conditions is disclosed for example, in U.S. Pat. No. 8,236,299 to Johe, et. al.

(iii) Cancer Therapy

Therapeutic uses of the ciEPSCs and their progeny include transplanting the induced pluripotent stem cells, stem cell populations, or progeny thereof into individuals to treat and/or ameliorate the symptoms associated with cancer. For example, in one embodiment, the ciEPSCs can be administered to cancer patients who have undergone chemotherapy that has killed, reduced, or damaged cells of a subject. In a typical stem cell transplant for cancer, very high doses of chemotherapy are used, often along with radiation therapy, to try to destroy all the cancer cells. This treatment also kills the stem cells in the bone marrow. Soon after treatment, stem cells are given to replace those that were destroyed.

In another embodiment, the ciEPSCs can be transfected or transformed (in addition to the de-differentiation factors) with at least one additional therapeutic factor. For example, once ciEPSCs are isolated, the cells may be transformed with a polynucleotide encoding a therapeutic polypeptide and then implanted or administered to a subject, or may be differentiated to a desired cell type and implanted and delivered to the subject. Under such conditions the polynucleotide is expressed within the subject for delivery of the polypeptide product.

(iii) Tissue Engineering ciEPSCs and their progeny can be used to make tissue engineered constructions, using methods known in the art. Tissue engineered constructs may be used for a variety of purposes including as prosthetic devices for the repair or replacement of damaged organs or tissues They may also serve as in vivo delivery systems for proteins or other molecules secreted by the cells of the construct or as drug delivery systems in general. Tissue engineered constructs also find use as in vitro models of tissue function or as models for testing the effects of various treatments or pharmaceuticals. The most commonly used biomaterial scaffolds for transplantation of stem cells are reviewed in the most commonly used biomaterial scaffolds for transplantation of stem cells is reviewed in Willerth, S. M. and Sakiyama-Elbert, S. E., *Combining stem cells and biomaterial scaffolds for constructing tissues and cell delivery* (Jul. 9, 2008), StemBook, ed. The Stem Cell Research Community, StemBook. Tissue engineering technology frequently involves selection of an appropriate culture substrate to sustain and promote tissue growth. In general, these substrates should be three-dimensional and should be processable to form scaffolds of a desired shape for the tissue of interest.

U.S. Pat. No. 6,962,814 generally discloses method for producing tissue engineered constructs and engineered native tissue. With respect to specific examples, U.S. Pat. No. 7,914,579 to Vacanti, et al., discloses tissue engineered ligaments and tendons. U.S. Pat. No. 5,716,404 discloses methods and compositions for reconstruction or augmentation of breast tissue using dissociated muscle cells implanted in combination with a polymeric matrix. U.S. Pat. No. 8,728,495 discloses repair of cartilage using autologous dermal fibroblasts. U.S. Published application No. 20090029322 by Duailibi, et al., discloses the use of stem cells to form dental tissue for use in making tooth substitute. U.S. Published application No. 2006/0019326 discloses cell-seed tissue-engineered polymers for treatment of intracranial aneurysms. U.S. Published application No. 2007/0059293 by Atala discloses the tissue-engineered constructs (and method for making such constructs) that can be used to replace damaged organs for example kidney, heart, liver, spleen, pancreas, bladder, ureter and urethra.

(ii) Cells Produced from ciEPSCs (Progeny)

The ciEPSCs can be induced to differentiate into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells (e.g., alpha cells, delta cells, PP cells, and beta cells), blood cells (e.g., leukocytes, erythrocytes, macrophages, and lymphocytes), retinal cells (and other cells involved in sensory perception, such as those that form hair cells in the ear or taste buds on the tongue), and nervous tissue including nerves.

(iii) Therapeutic Compositions

The ciEPSCs can be formulated for administration, delivery or contacting with a subject, tissue or cell to promote de-differentiation in vivo or in vitro/ex vivo. Additional factors, such as growth factors, other factors that induce differentiation or dedifferentiation, secretion products, immunomodulators, anti-inflammatory agents, regression factors, biologically active compounds that promote innervation, vascularization or enhance the lymphatic network, and drugs, can be incorporated.

The induced pluripotent cells can be administered to a patient by way of a composition that includes a population of ciEPSCs or ciEPSC progeny alone or on or in a carrier or support structure. In many embodiments, no carrier will be required. The cells can be administered by injection onto or into the site where the cells are required. In these cases, the cells will typically have been washed to remove cell culture media and will be suspended in a physiological buffer.

In other embodiments, the cells are provided with or incorporated onto or into a support structure. Support structures may be meshes, solid supports, scaffolds, tubes, porous structures, and/or a hydrogel. The support structures may be biodegradable or non-biodegradable, in whole or in part. The support may be formed of a natural or synthetic polymer, metal such as titanium, bone or hydroxyapatite, or a ceramic. Natural polymers include collagen, hyaluronic acid, polysaccharides, and glycosaminoglycans. Synthetic polymers include polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters. These may be in for the form of implants, tubes, meshes, or hydrogels.

Solid Supports

The support structure may be a loose woven or non-woven mesh, where the cells are seeded in and onto the mesh. The structure may include solid structural supports. The support may be a tube, for example, a neural tube for regrowth of neural axons. The support may be a stent or valve. The support may be a joint prosthetic such as a knee or hip, or part thereof, that has a porous interface allowing ingrowth of cells and/or seeding of cells into the porous structure. Many other types of support structures are also possible. For example, the support structure can be formed from sponges, foams, corals, or biocompatible inorganic structures having internal pores, or mesh sheets of interwoven polymer fibers. These support structures can be prepared using known methods.

The support structure may be a permeable structure having pore-like cavities or interstices that shape and support the hydrogel-cell mixture. For example, the support structure can be a porous polymer mesh, a natural or synthetic sponge, or a support structure formed of metal or a material such as bone or hydroxyapatite. The porosity of the support structure should be such that nutrients can diffuse into the structure, thereby effectively reaching the cells inside, and waste products produced by the cells can diffuse out of the structure The support structure can be shaped to conform to the space in which new tissue is desired. For example, the support structure can be shaped to conform to the shape of an area of the skin that has been burned or the portion of cartilage or bone that has been lost. Depending on the material from which it is made, the support structure can be shaped by cutting, molding, casting, or any other method that produces a desired shape. The support can be shaped either before or after the support structure is seeded with cells or is filled with a hydrogel-cell mixture, as described below.

An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape. Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Hydrogels

In another embodiment, the cells are mixed with a hydrogel to form a cell-hydrogel mixture. Hydrogels may be administered by injection or catheter, or at the time of implantation of other support structures. Crosslinking may occur prior to, during, or after administration.

D. Animal Models and Organ Regeneration

Isolated ciEPSC can be used to generate animal models incorporating ciEPSC from a desired species (donor) into a second animal (recipient) of the same or different species. The donor animal can be a mammal such as a human, mouse, rat, pig, cattle, sheep, goat, horse, dog, chimpanzee, gorilla, orangutan, monkey, marmoset, etc. In some preferred embodiments, the donor mammal is a human and the recipient mammal is non human, used to provide a humanized animal model. In other embodiments, the donor and recipient animals are size matched. The recipient may be any animal other than human, such as pig, rat, mouse, cattle, sheep, goat, horse, dog, chimpanzee, gorilla, orangutan, monkey, marmoset, and bonobo. The ciEPSC can be used for organ regeneration in a mammal, which is not a human; ciEPSC can be used to produce a desired organ in the mammal where the mammal has an abnormality associated with a lack of development of that organ in a development stage.

The method includes transplanting ciEPSC into a blastocyst stage fertilized egg of the recipient non-human mammal; developing the fertilized egg in a womb of a non-human surrogate parent mammal to obtain a litter, and obtaining the organ from the litter, using methods known in the art. Examples of organs that can be produced include, but are not limited to, solid organ with a fixed shape, such as kidney, heart, pancreas, cerebellum, lung, thyroid gland, hair, and thymus. The recipient embryo may be from any animal other than human, such as pig, rat, mouse, cattle, sheep, goat, horse, dog, chimpanzee, gorilla, orangutan, monkey, marmoset, etc.

Methods for generating humanized mouse models are known in the art (U.S. Publication No. 20110258715) and reviewed for example in Ito, et al., *Cellular & Molecular Immunology*, 9:208-214 (2012). Examples of recipient embryos having an abnormality associated with the development of an organ of interest, and which can be used to regenerated that organ include, Sall1 knockout animal having an abnormality associated with a lack of development of a kidney in the development stage (Nishinakamura, et al., *Development*, 128: 3105-3115 (2001); a Pdx1 knockout animal having an abnormality associated with a lack of development of a pancreas in the development stage (Offield, et al., *Development*, 122: 983-995 (1996); a Wnt-1 (int-1) knockout animal having an abnormality associated with a lack of development of a cerebellum in the development stage (McMahon, et al., *Cell*, 62:1073-1085, (1990); a T/ebp knockout animal having an abnormality associated with a lack of development of a lung and a thyroid gland in the development stage (Kimura, et al., *Genes and Development*, 10:60-69, 1996); or a dominant negative-type transgenic mutant animal model which overexpresses the deficiency of an intracellular domain of fibroblast growth factor (FGF) receptor (FGFR), and which causes deficiencies of multiple organs such as kidney and lung (Celli, et al., *EMBO J.*, 17:1642-655, (1998)), can be used. Alternatively, nude mice can be used to produce of hair or thymus. A "founder" animal described U.S. Publication No. 20110258715 may also be used.

V. Kits

Kits are provided which include the chemical inducers of extended pluripotency (CEP) disclosed herein. The CEPs are as described above. These may be in a form having defined concentrations to facilitate addition to cell culture media to produce a desired concentration. The kit may include directions providing desired concentration ranges and times of administration based on the donor cell types. The kit may also include cell culture media which is pre-mixed with the CEPs for culture of donor cells to induce extended pluripotency.

The present invention will be further understood by reference to the following non-limiting examples.

EXAMPLES

Methods

Small-Molecule Libraries

The small molecule libraries used for the screen were purchased or generated in-house as described in Table 1.

TABLE 1

Small molecule compound libraries used in screen

| Library | Source | No. of compounds |
|---|---|---|
| Tocriscreen ™ Total | Tocris | 1,120 |
| protein Kinase Inhibitor Library I, II, III | Millipore | 324 |
| StemSelect Small Molecule Regulators | Calbiochem | 303 |
| Nuclear Receptor Ligand library | Enzo | 76 |
| Selected Small Molecules* | Our lab | 108 |

*this library was generated in-house, including 108 selected small molecules related to pluripotency or epigenetic modification Chemical Screening Basing on the Luciferase Reporter Assay Initial efforts were focused on identifying novel small molecules that support naïve pluripotency in human. Based on the 2i plus LIF condition that supports naïve pluripotency in mouse (ERK inhibitor PD0325901, GSK3I3 inhibitor CHIR99021, and human LIF (hLIF)), an initial screening was performed, to identify chemical compounds that could activate the naïve pluripotency marker OCT4 distal enhancer (DE) using primed hES cells (Yeom, et al., *Development*, 122:881-894 (1996); Tesar, et al., *Nature*, 448:196-199 (2007) (FIG. 1A and Table 1).

Oct4 is at the top of the pluripotency regulatory hierarchy in pluripotent cells. The upstream region of the transcriptional initiation site of the Oct4 gene contains three regulatory elements for gene transcription: the distal enhancer (DE), proximal enhancer (PE), and TATA-less proximal promoter (PP). Each enhancer contains multiple potential binding sites for transcription factors that can either activate or repress Oct4 expression.

A first screen was performed using established primed hES H9 cells (human embryonic stem cell line H9), to identify small molecules that activate OCT4 DE. Primed hES/hPS (human pluripotent stem) H9 cells were dissociated in ACCUTASE® (cell detachment solution) (Millipore). Then OCT4-DE luciferase plasmid (Addgene) was transfected into H9 cells by nucleofection (4D-Nucleofector™ System, Lonza). A control vector pGL4.74 [hRluc/TK] (Promega, E6921) was co-transfected for normalization.

After transfection, the primed hES/hPS H9 cells were seeded into matrigel-coated 24 well plates at a density of $2 \times 10^4$ cells per well, and cultured in conventional human embryonic stem cell (ES) medium (DF12 plus 20% KSR, detailed formulation is provided below) plus Y27632[(+)-(R)-trans-4-(1-aminoethyl)-N-(4-pyridyl)cyclohexanecarboxamide+++dihydrochloride)], a selective inhibitor of Rho-associated, coiled-coil containing protein kinase (ROCK) (10 μm).

12 hours later, the medium was replaced with N2B27 medium supplemented with hLIF (human Leukemia Inhibitory Factor)+2i (10 ng/mL hLIF (Peprotech), 1 μm ERK (extracellular signal-regulated kinase) inhibitor PD0325901 (Tocris), and 3 μm GSKβ inhibitor CHIR99021 (Tocris) (detailed formulation of N2B27 medium is provided below). One single compound from the libraries was added into each well respectively. All compounds in Table 1 were tested. After being treated for 6 days, H9 cells were lysed for detecting luciferase activity using the Dual-Luciferase Reporter Assay System (Promega, E1960).

Chemicals were identified as positive candidates based on a two-fold upregulation of DE luciferase activity, compared with the primed hES cell control. After the screening, more than 100 candidates were obtained, which could enhance the OCT4 DE activity by more than 2-fold compared with cells that were cultured in traditional primed hPSC medium.

Identification of Small Molecules that Support Dome-Shaped hES Cell Colony Formation.

Primed hES are flat colonies. By contrast, naïve human pluripotent cells are dome-shaped colonies. Therefore, any resultant human EPS cells can be morphologically distinguished from primed human pluripotent stem cells.

Positive candidates from the first screen above were further screened in order to identify small molecules that support TGFβ signaling-independent self-renewal of hES cells (Tesar, et al., *Dev.*, 448:196-199 (2007); James, et al.,*Dev.*, 132:1273-1282 (2005); Vallier, et al., *J. Cell. Sci.*, 118:4495-4509 (2005)). A TGFβ inhibitor SB431542 was added to the chemical cocktail (2i+LIF+candidate) at the later stage of treatment (FIG. 1A).

Specifically, primed hES/hPS H9 cells were digested into single cells using ACCUTASE® (cell detachment solution), and seeded into a matrigel-coated 24-well plate ($1\times10^4$ cells per well) on day 0 in conventional hES medium plus Y27632. On day 1, the conventional hES medium was replaced by the N2B27 medium supplemented with the hLIF+2i base, and candidates from the first round screen were added individually into each well. The medium was changed every two days and replaced with fresh N2B27 medium supplemented with hLIF+2i. 6 days later (i.e., on day 7), a TGF (transforming growth factor) β inhibitor, SB431542 (10 μm, Tocris), was added into wells with un-differentiated cells for another 6 days. After this screening, more than 30 candidates were obtained that supported TGF-beta-signaling-independent self-renewal in the short term.

Culture of Primed hES/hPS and Naïve NHSM-hES Cells

The following already established primed hES/hPS cell lines were used (the passage number of the cell line taken for EPS conversion is indicated in parentheses): H1 (passage 30), 0227E (around passage 20), HSF1 (around passage 50) and HSF6 (around passage 60) and H9 (passage 40). hES/hPS cell lines H1 (WA01) and H9 (WA09) were obtained from WiCell, and authenticated by karyotype analysis. Primed hES cells were maintained in 20% $O_2$, 5% $CO_2$ conditions on mitomycin C-inactivated MEF feeder cells ($2\times10^4/cm^2$) or matrigel-coated dishes in conventional hES/hPS cell medium: DMEM-F12 (Invitrogen) supplemented with 20% knockout serum replacement (KSR) (Invitrogen), 1 mm glutamine (Invitrogen) or 1% GlutaMAX (Invitrogen, 35050), 1% nonessential amino acids (Invitrogen), 0.1 mm β-mercaptoethanol (Invitrogen), and 4-10 ng/ml bFGF (basis fibroblast growth factor) (Peprotech). Cell lines were passaged at a split ratio of 1:3 to 1:5 every 5-7 days using Dispase. Naïve NHSM-hES cells were cultured according to previous reports (Gafni, et al., *Nature*, 504(7479):282-6 (2013)).

Culture of Mouse Naïve ES Cells.

Mouse naïve ES cells were maintained in 20% $O_2$, 5% $CO_2$ conditions on mitomycin C-inactivated MEF feeder cells or gelatin-coated dishes, in 2i medium containing serum-free N2B27 medium supplemented with 10 ng/mL hLIF (Peprotech), 3 μm CHIR99021 (Tocris) and 1 μm PD0325901 (Tocris). Cells were passaged every 2-4 days by 0.05% trypsin-EDTA (Invitrogen).

Conversion of Non-hEPS Cells into hEPS Cells.

Preparation of N2B27-LCDM Medium 500 ml of N2B27 medium was generated by including: 240 ml DMEM/F12 (Dulbecco's Modified Eagle Medium/Nutrient Mixture F-12) (Invitrogen, 11320), 240 ml NEUROBASAL® medium (basal cell culture medium) (Invitrogen, 21103-049), 2.5 ml N-2 supplement (Invitrogen, 17502048), 5 ml B-27 supplement (Invitrogen; Ser. No. 17/504,010), 1 mm glutamine or GlutaMAX™ (Invitrogen), 1% nonessential amino acids (Invitrogen), 0.1 mm β-mercaptoethanol (Invitrogen), penicillin-streptomycin (Invitrogen), (optional) 5 mg/mL BSA (bovine serum albumin) (Sigma), and small-molecule inhibitors as below.

Small molecules and cytokines (purchased from Peprotech, Tocris or Santa Cruz) were supplemented as indicated at the following final concentrations: hLIF: 10 ng/mL; CHIR99021: 3 μm for mouse EPS cells and 1-1.5 μm for human EPS cells; (S)-(+)-Dimethindene maleate (DiM): 2 μm; Monocycline hydrochloride (MiH): 2 μm. The N2B27 medium, supplemented with small molecules and cytokines was termed N2B27-LCDM. Tests for *mycoplasma* contamination were performed for all the cell lines using PCR-based approach or MycoAlert *mycoplasma* detection kit (Lonza) following the manufacturer's recommendation.

(a) Conversion of Primed hES/hPS Cells into hEPS Cells.

Conversion was conducted usually on day 3 or day 4 after the last passage of primed hES/hPS cells (if they were passaged every 5-6 days. Colonies usually reached 60-70% confluence.

Before conversion, primed hES cells were kept in an undifferentiated state, which did not overgrow on the day of conversion.

Mitomycin C-inactivated mouse embryonic fibroblast (MEF) Feeder cells were seeded the day before the passage ($3\times10^4$ cells per $cm^2$) of the primed cells.

Primed hES/hPS cells were digested into single cells using 0.05% tyrpsin-EDTA (Invitrogen). After digestion, cells were seeded normally in human ES medium at the split ratio of 1:3 to 1:4. Subsequently, 12 hours after seeding in human ES medium, the human ES medium was replaced with the N2B27-LCDM medium. The N2B27-LCDM medium was changed daily. For primed hES cell lines that can hardly survive after single-cell passaging, Y27632 (1-10 μm) was added in the medium 24 hours before conversion, and kept in the LCDM medium in the first few passages (3-5 passages). Alternatively, primed hES cells were digested into small colonies using Dispase, and seeded using conventional hES medium. 12 or 24 hours later, hES medium was replaced with the LCDM-containing medium. Optionally, if the primed human PS cells are tolerant of single cell digestion after the Y27632 treatment, then the primed human PSCs can be digested into single cells using 0.05% Trypsin-EDTA. Y27632 should be added to the medium during the first 12 hours before and after passaging.

Dome-shaped colonies gradually emerged during this period. Then, 3-6 days later, 0.05% Trypsin-EDTA (Invitrogen, 25300) was used to trypsinize the cells for 3 minutes at 37° C. in the incubator. MEF medium was used to stop the trypsinization. The cells were washed off the surface of dish by pipetting the medium slowly up and down: they were collected in an appropriately sized tube and centrifuged at 1, 200-1, 600 rpm (250-450×g) at room temperature for 3 minutes. The cells were re-suspended in an appropriate volume of N2B27-LCDM medium (according to the cell lines and growth ratio) and seeded to the plate with MEF feeders. For one six-well plate, approximately 50,000-100, 000 cells per well were seeded. The split ratio was usually from 1:3 to 1:10. Then, the cells were incubated at 20% $O_2$, 5% $CO_2$, at 37° C. If it was still difficult for the cells to survive after the passaging, then Y27632 was added during the first few passages (3-5 passages) to ensure successful conversion: the addition was made during the first 12 hours before and after passaging. If the cells grew slowly after the single-cell passage, then it was recommended to decrease the split ratio (from 2:1 to 1:3) during the first few passages (3-5 passages). After a few passages, cells that were cultured in the LCDM medium could gradually proliferate well.

For the chimeric experiment, primed hPSCs-derived hEPS cells with higher passages (passage>10 after conversion) were recommended to be used to ensure that the human EPS cells were reprogrammed to the extended pluripotent state. In our experiments, converted domed colonies at passage 10 showed bi-potentiality in chimeric experiments, suggesting that the minimal culture period for conversion could be 10 passages (about 40 days). The conversion of human primed pluripotent stem cells into EPS cells was repeated by six different colleagues in our laboratory in at least 20 independent experiments.

(b) Human EPS Cells Derivation from Blastocysts.

Human embryos at the blastocyst stage produced by in vitro fertilization for clinical purposes were obtained with informed written consent and approval. Whole embryos were seeded onto mitomycin C-inactivated MEF feeder cells ($4 \times 10^4$/cm$^2$) and cultured in LCDM medium after the zona pellucid were removed by protease (Sigma, P8811). The MEF cell culture medium was changed into an FBS-LCDM medium at least half an hour before the embryos were seeded.

The FBS-LCDM medium was prepared by including: KnockOut DMEM (10829-018, Invitrogen) supplemented with 10% knockout serum replacement (KSR) (Invitrogen, 10828010), 10% FBS (Hyclone, SH30070.03E), 1% GlutaMAX (Invitrogen, 35050), 1% nonessential amino acids (Invitrogen, 21103) and 0.1 mm β-mercaptoethanol (Invitrogen, 21985) and LCDM (10 ng/mL; 1.5 µM, 204; and 2 µM, respectively). In order to enhance the survival of embryos in some experiments, Y27632 (10 µM, Tocris, 1254) was added into the FBS-LCDM medium.

For the unhatched blastocysts, the zona pellucid were removed by protease (Sigma, P8811). The time for the treatment of protease varied among different blastocysts, from half a minute to 5 minutes. When the zona pellucid gradually began to disappear, the blastocysts were transferred into the G2 PLUS medium that was prepared earlier. The embryos were washed 3 to 5 times to remove the residual protease as much as possible, and then, they were seeded onto the prepared MEF feeder. Two days later, the FBS-LCDM medium was changed into N2B27-LCDM medium if the embryo had attached onto the MEF feeder cells. Otherwise, half of the cultured FBS-LCDM medium was removed and changed into the N2B27-LCDM medium.

Initial outgrowths were visible 4 to 7 days later and were dissociated mechanically into small pieces and reseeded on MEF feeder cells with FBS-LCDM medium. The newly established cell lines were further passaged using 0.05% trypsin-EDTA (Invitrogen) and then either frozen or used for further analysis.

During the first few passages (3-5 passages), colonies should be dissociated mechanically and cultured in the FBS-LCDM medium supplemented with Y27632 (10 µM) for the first 2 days after seeding. The FBS-LCDM medium was changed into the N2B27-LCDM medium later. Colonies that morphologically resembled mouse ES colonies gradually emerged. If these colonies survived and proliferated well, 0.05% trypsin-EDTA could be used for digesting cells. The newly established cell lines were further passaged using 0.05% trypsin-EDTA (Invitrogen), and then, they were either frozen or used for further analysis.

(c) Reprogramming of Somatic Cells and Cell Infection.

Human embryonic fibroblasts were isolated from 2 to 3 month-old embryos that were obtained with informed written consent and approval by the Clinical Research Ethics Committee and used to generate induced pluripotent stem cells (iPSC).

For reprogramming with oriP/EBNA1-based episomal vectors, episomal plasmids including pCXLE-hOCT3/4 (insert: human OCT3/4), pCXLE-hSK (insert: human SOX2 and LKF4), pCXLE-hUL (insert: human L-MYC) and pCXLE-EGFP (insert: eGFP) (Addgene 27076, 27078, 27080, 27082) (Okita, et al., *Nat. Methods*, 8(5):409-12 (2011)) were co-transfected into fibroblasts via nucleofection (4D-Nucleofector™ System, Lonza).

Transfected fibroblasts (approximately $1.0 \times 10^6$ cells per nucleofection) were directly plated into three 10 cm feeder-seeded dishes in 1 Dulbecco's modified Eagle's medium (DMEM; Hyclone) containing 10% fetal bovine serum (Invitrogen). The fibroblasts were replated 7 days post-infection and cultured in Knockout DMEM (Gibco) with 10% fetal bovine serum and 10% KSR containing 50 ng/ml bFGF (Origene), 3 µm CHIR99021, 10 ng/ml human LIF (Peprotch), 10 µm Forskolin (Tocris). Culture medium was changed every other day. On day 12 post-transfection, the medium was replaced with LCDM medium. Colonies with morphology similar to EPS colonies were visible on day 15 after transfection. Colonies were picked and passaged by 0.05% trypsin-EDTA for further analysis.

Mice

All mouse work was approved by the Institutional Animal Care and Use Committee. The strains of mice used in this study included C57BL/6J-Tg(GOFGFP)11Imeg/Rbrc (OG), C57BL/6NCrlVr (C57), ICR, and F1 hybrids between STOCK Tg(Sox2-cre)1Amc/J and B6.Cg-Gt(ROSA)26Sortm14(CAG-tdTomato)Hze/J, which were purchased from Jackson Laboratory, and F1 hybrids between C57BL/6NCrlVr (C57) and 129 or F1 hybrids between C57BL/6NCrlVr (C57) and DBA. Immunodeficient mice used for teratoma formation assay were commercially purchased.

Establishment and Culture of Mouse EPS Cells.

For mEPS cells derived directly from blastocysts, blastocysts of OG, C57, ICR or F1 hybrids between STOCK Tg(Sox2-cre)1Amc/J and B6.Cg-Gt(ROSA)26Sortm14(CAG-tdTomato)Hze/J mice, or F1 hybrids between C57BL/6NCrlVr (C57) and 129 were seeded on MEF feeders with LCDM medium. 4 days later, outgrowths were observed and dissected into single cells. mEPS cells were passaged every 2-3 days and frozen or used for further analysis.

For mEPS cells converted directly from mouse naïve ES cells TT2-2i, mouse naïve ES cells the 2i medium was replaced with LCDM medium 12 h after seeding. 2-3 days later, colonies were passaged for further analysis.

Culture of Human and Mouse Extended Pluripotent Stem Cells.

Human and mouse extended pluripotent stem cells were cultured in serum-free N2B27-LCDM medium in 20% O$_2$, 5% CO$_2$ conditions. To maintain human EPS cells in an undifferentiated state, the following criteria were used: a) avoidance of plating human EPS cells too sparsely; b) use of the proper quantity of freshly prepared MEF feeder cells; and c) not allowing human EPS cells to overgrow (for example, attain more than 90% confluence; preferably, the cells should be at less than 90% confluent). Accordingly, human and mouse EPS cells were cultured on mitomycin C-inactivated mouse embryonic fibroblast (MEF) feeder cells ($3 \times 10^4$ cells per cm$^2$), and were passaged by single-cell trypsinization (0.05% trypsin-EDTA, Invitrogen) every 2-4 days (normally at a split ratio of 1:6 to 1:10). Passage numbers of EPS cells indicate number of passages counted after the acquisition of the extended pluripotent state. The N2B27-LCDM medium was changed every day with fresh LCDM medium.

Mouse Embryo Micromanipulation, Whole-Mount Staining and Imaging.

The cross-species chimeric assay was approved by the Ethics Committee.

For chimeric experiments, human and mouse EPS cells were used 1 day before they were due for passaging; these cells which showed an optimal undifferentiated morphology and proliferated exponentially. At this time point, the colonies should be at subconfluent density (approximately 70% density).

For hEPS cell injection, hEPS cells were trypsinized (by 0.05% trypsin-EDTA) and the digested cells were filtered through a cell strainer (40 μm). Afterward, the cells were centrifuged at 1, 200-1, 500 rpm (250-390×g) at room temperature for 3 minutes. Supernatant was removed, and the cells were re-suspended in the culture medium at a proper density ($2-6*10^5$ cells/mL). For human cells injection, 10 μM Y27632 was recommended to be added into the suspension. The suspension was placed on ice for 20-30 minutes before injection, and microinjected into E2.5 or E3.5 embryos of ICR diploid mouse embryo (10-15 cells per embryo). Approximately 15 injected embryos were transferred to each uterine horn of 0.5 or 2.5 days post coitum pseudo-pregnant females.

For injection of Tdtomato-labeled mEPS cells and conventional naïve mouse ES cells, mEPS and naïve mouse ES cells were trypsinized and microinjected in the same way as for hEPS cells except that Y27632 was not added into the suspension.

Conceptuses were dissected at E10.5 developmental stage for whole-mount staining with an anti-human nuclei antibody (clone 235-1, 1:300; Millipore), co-stained with anti-GATA4 (sc-1237, 1:200; Santa Cruz) or anti-SOX2 (1:200, sc-17320; Santa Cruz) antibodies according to the whole-mount staining protocol from Abcam.

For confocal analysis, mounted embryos were imaged by UltraVIEW VoX systems (PerkinElmer).

Conceptuses were dissected at E12.5 developmental stage and observed using an immunofluorescence stereomicroscope for detecting Tdtomato+ cell localization. Occasionally, several pregnant mice were excluded from further analysis if no mouse embryos were obtained from these mice.

For immunostaining of tissue sections, embryos and placentas were isolated from the E10.5 conceptuses, followed by embedding, freezing, slicing (5 μm thick) from the sagittal side. The embryos which were injected with Tdtomato reporter labeled human cells were stained with anti-NANOG (1:200, ab80892; Abcam) and anti-Tdtomato/RFP (1:400, ab62341; Abcam), and the placentas were stained with anti-Tdtomato/RFP (1:400, ab62341; Abcam), anti-CK8 (1:50, sc-52324; Santa Cruz) and anti-hCGβ (1:200, ab131170; Abcam). Some embryos were sliced (5 μm thick) from the sagittal side. The embryos were stained with anti-FOXA2 (ab108422, 1:50; Abcam) and anti-human nuclei antibody (clone 235-1, 1:300; Millipore). All these samples were imaged by the ImageXpress Micro High Content Screening System (MolDev).

Detection of hEPS-Derived Cells in Placenta and Yolk Sac from E10.5 Chimeric Mouse Conceptuses For detecting extraembryonic chimerism of hEPS cells, placenta and yolk sac were isolated from E10.5 conceptuses and digested using Collagenase IV. Isolated primary cells were seeded into 24-well plates and cultured in Knockout DMEM supplemented with 10% FBS and 10% KSR for 3-4 days before further analysis.

Chimeric Assay of Single-Cell Microinjection.

The cells used in this experiment were cultured and prepared in a way that was similar to that of the multiple-cell microinjections. The cell suspension was placed on ice for 20-30 minutes before injection. After being placed on ice, the digested single cells were used for injection within 1 hour: in other words, the whole injection process should not take more than 30 minutes. Afterward, the injected embryos are recovered for 1-2 hours in a humidified incubator with 5% $CO_2$ at 37° C. If the cells were placed on ice for more than 1 hour, then another batch of cells was digested for the remaining injections. Single cells (Tdtomato-labeled human cells, unlabeled human cells, Tdtomato-labelled mEPS and naïve mouse ES cells) were microinjected into 8-cell stage ICR diploid mouse embryos and allowed to develop ex vivo until E5.0 (60 hours in supplemented KSOM (K(potassium)-supplemented simplex optimised medium); Summers, et al., J. Assist Reprod. Denet., 30(8):995-999*(2013)). In other experiments, for the generation of chimeric blastocysts, the injected embryos were cultured in the N2B27-LCDM medium for the first 4 hours (10 μM Y27632 (Tocris, 1254) was recommended to be added for the culture of chimeric embryos injected with single hEPS cells), and then, they were changed into the G2 PLUS medium (Vitrolife, 10131). After 60 hours, the embryos were fixed and immunostained.

Embryos were then fixed and immunostained. For embryos injected with Tdtomato-labeled human cells, antibodies included OCT4 (sc-5279; Santa Cruz or ab181557; Abcam) and CDX2 (ab74339; Abcam or CDX2-88, AM392; Biogenex). For unlabeled human cells, antibodies included: anti-human nuclei antibody (MAB1281; Millipore), CDX2 (sc-19478; Santa Cruz) and OCT4 (Ab18976-100; Abcam or ab181557; Abcam). For injection of mEPS and naïve mouse ES cells, cells were constitutively labeled with Tdtomato reporter. Microinjection and immunostaining were conducted the same as above. Antibodies include: CDX2 (CDX2-88, AM392; Biogenex), OCT4 (Ab18976-100; Abcam).

To examine the in vivo chimeric ability of single mEPS cells, chimeric embryos injected with single mEPS cells were allowed to recover for 1-2 hours in a humidified incubator with 5% $CO_2$ at 37° C. and were transferred to uterine horns of 0.5 or 2.5 days post coitum pseudo-pregnant females. Conceptuses were dissected at either E10.5, E12.5 or E17.5 developmental stage and observed using an immunofluorescence stereomicroscope for detecting Tdtomato+ cell localization. The placenta was isolated from the E10.5 conceptuses, followed by embedding, freezing, slicing (5 μm thick) from the sagittal side and then, staining with CK8 (1:50, sc-52324; Santa Cruz), PROLIFERIN (1:50, sc-47345; Santa Cruz) and TPBPA (1:100, ab104401; Abcam). The samples were further analyzed by the ImageXpress Micro High Content Screening System (MolDev).

Derivation of Trophoblast Stem (TS)-Like and ES-Like Cells from Single-mEPS-Chimerized-Embryos.

A single Tdtomato-labeled mEPS cell was injected into an 8-cell mouse embryo and cultured in the N2B27-LCDM medium for 4 hours. The injected embryos were transferred to G2 PLUS medium and cultured for additional 56 hours. The same chimerc embryos were used to generate both ES and TS cell lines by seeding half of them into traditional mES derivation medium while the others were seeded into traditional TS derivation medium[13]. Both ES- and TS-like colonies were derived from the same chimeric embryo simultaneously. Tdtomato-labeled traditional mouse ES TT2 and mc2i-1 were used as controls in this assay separately and each 8-cell embryo was injected with 10-15 cells.

Chimeric Assay of the TS-Like and ES-Like Cells.

10-15 cells of the established TS-like or ES-like cell line were injected into an 8-cell mouse embryo. For the in vitro chimeric assay, the injected embryos were cultured in G2 PLUS medium for 60 hours. Then, they were fixed and immunostained. For the in vivo chimeric assay, the conceptuses were dissected at E13.5 developmental stage and observed using an immunofluorescence stereomicroscope for detecting the presence of fluorescent positive cells.

Immunofluorescence.

Cells were fixed in 4% paraformaldehyde at room temperature for 15 min, and blocked with PBS containing 0.2% Triton X-100 and 3% normal donkey serum (Jackson Immuno Research) at room temperature for 45 min. Cells were incubated with primary antibodies at 4° C. overnight. Secondary antibodies (Jackson Immuno Research) were incubated at room temperature for 1 hour. Nuclei were stained with DAPI (Roche). Antibody details were provided below.

For human cells the antibodies used were: anti-OCT4 antibody (Ab18976-100; Abcam; sc-5279; Santa Cruz), anti-human NANOG antibody (AF1997; R&D), anti-SOX2 antibody (sc-17320; Santa Cruz), Anti-trimethyl-Histone H3 (Lys27) Antibody (07-449; Millipore) and KLF4 (sc-20691; Santa Cruz). For mouse cells, the antibodies were: anti-NANOG (ab80892; Abcam), anti-KLF (kruppel-like factor) 4 (sc-20691; Santa Cruz), OCT4 (Ab18976-100; Abcam), SALL4 (ab29112; Abcam) and SOX2 (sc-17320; Santa Cruz).

For the immunofluorescent analysis of chimeric blastocysts, the used antibodies included: OCT4 (ab181557; Abcam), GATA3 (ab199428; Abcam), NANOG (ab80892; Abcam) and CDX2 (CDX2-88, AM392; Biogenex). For the immunofluorescent analysis of TS-like cells, ES-like cells or cells cultured in TS medium, the used antibodies included: OCT4 (sc-5279; Santa Cruz), NANOG (ab80892; Abcam), SOX2 (sc-17320; Santa Cruz), CDX2 (CDX2-88, AM392; Biogenex) and EOMES (ab23345; Abcam).

Flow Cytometry

Chimeric tissues of embryos, yolk sacs and placentas were isolated and digested into single cells using Collagenase IV. Suspensions were filtered through a cell strainer (40 μm). Then, the samples were analyzed on a BD LSRFortessa machine. Data analysis was performed using FlowJo software (Ashland).

Analysis of Trophoblast Marker Gene Expression in mEPS-Derived Placenta Cells

Chimeric placental tissues were isolated and digested using CollagenaseIV. Both primary Tdtomato$^+$ and Tdtomato$^-$ placental cells were purified using FACS. Total RNA of purified cells was extracted using Trizol (Invitrogen). cDNA was prepared as described before[31]. The amplified cDNA product was diluted ten-fold as required by the qPCR template. Quantitative PCR analysis was conducted using the KAPA SYBR® FAST qPCR Kit on a Bio RAD CFX Connect Real-Time System. The primers that were used for real-time PCR are listed in Table 2.

Transwell-Based Invasive Assay.

Chimeric placental tissues were isolated and digested using CollagenaseIV. Primary placental cells from one or half of the chimeric placenta were seeded onto Matrigel™-coated filters (8 μm pore size; BD Biosciences, Franklin Lakes, N.J., USA) in 24-well plates. Briefly, the cells were seeded onto the upper chamber of the Transwell in serum-free DMEM/F12 media. The lower chamber of the Transwell was filled with DMEM/F12 media that contained 10% FBS. The chambers were incubated at 37° C. with 5% $CO_2$ for 24 hrs. At the end of the incubation, the cells on the upper surface of the filter were removed using a cotton swab. The cells invading through the filter to the lower surface were fixed with 4% paraformaldehyde for 20 min, and further analyzed by immunofluorescence. The following antibodies were used for immunofluorescence: CK8 (1:200, sc-52324; Santa Cruz), CK7 (1:40, MA5-11986; Thermo Scientific), and Tdtomato/RFP (1:400, ab62341; Abcam).

Evaluation of Human OCT4 Transcriptional Regulation

To evaluate human OCT4 transcriptional regulation of the detected human cell lines, OCT4-DE luciferase plasmid (Addgene) was transfected into cells by nucleofection (4D-Nucleofector™ System, Lonza). A control vector pGL4.74 [hRluc/TK] (Promega, E6921) was co-transfected for normalization. Baseline activity was analyzed by transfection with an empty vector. After transfection, cell lines were seeded into matrigel-coated 96-well plates at a density of $5*10^3$ cells per well. Then, 48 hours later, the cells were lysed for detecting luciferase activity using the Dual-Luciferase Reporter Assay System (Promega, E1960).

EB Formation Assay

Mouse and human EPS cells were trypsinized to single cells, separated from the MEF feeder cells by pre-plating on gelatin-coated plates, and cultured for 6 days on ultra-low attachment plates (Corning) in IMDM (Iscove's Modified Bulbecco's Medium) (Gibco) supplemented with 15% fetal bovine serum (Gibco). Then, EBs were collected and plated on the matrigel-coated plates for 6 days in the same medium, fixed and detected. For human cells, antibodies include: anti-SOX17 antibody (AF1924; R&D), anti-FOXA2 antibody (ab108422; Abcam), anti-LHXS antibody (sc-130469; Santa Cruz), anti-α-SMA antibody (CBL171; Millipore), anti-CDX2 antibody (ab74339, Abcam), and anti-GATA6 antibody (sc-9055, Santa Cruz). For mouse cells, antibodies include: anti-FOXA2 antibody (ab60721; Abcam), anti-β-III TUBULIN antibody (sc-80016; Santa Cruz), anti-α-SMA antibody (CBL171; Millipore), and anti-CDX2 antibody (CDX2-88, AM392; Biogenex).

Teratoma Assay

Human and mouse EPS cells were collected by trypsinization before injection. Approximately $10^6$ cells were injected sub-cutaneously into immunodeficient mice. Teratomas generally developed within 2-6 weeks, and animals were killed before the tumor size exceeded 1.5 cm in diameter. The teratomas were then embedded in paraffin and processed for hematoxylin and eosin staining.

To analyze the extraembryonic differentiation potential of hEPS cells in teratoma assay, immunochemistry assay was applied. After the hEPS- or primed hPSCs-derived teratomas were being fixed and embedded, 5-μm-thick sections were used for immunohistochemistry staining. After dewaxation and hydration, 3% $H_2O_2$ was used to block endogenous peroxidase. Subsequently, the tissues were blocked by 10% normal serum of the secondary antibody animal origin. Samples were incubated with the primary antibody hCGβ (ab131170; Abcam) at 4° C. and further incubated with the second antibody conjugated with horseradish peroxidase (HRP) for 30 min at room temperature. After visualization by diaminobenzidine (DAB), the tissues were stained with Harris hematoxylin.

Comparative Genomic Hybridization (CGH) Analysis.

For CGH experiments, genomic DNA was extracted and hybridized to Custom SurePrint G3 8×60K human whole-genome AGI-CGH arrays by Imagenes using cell lines at early passage as a reference.

Karyotype Analysis

G-band chromosomal analysis was performed as reported (Longo, et al., *Transgenic Res.*, 6:321-328 (1997).

Doubling Time Calculation

The cells were removed from the plates using 0.05% trypsin-EDTA (Invitrogen): they were counted and plated onto 24-well plates that were pre-seeded with feeder cells at a density of 10,000 cells per well in the appropriate medium without Y27632. The growth rate was determined by counting the number of cells using a hemacytometer as a function of time. Data from the exponential phase of growth (time points at 48 and 72 h) were used to obtain an exponential growth curve. The doubling time was calculated following the formula: $DT=48*[\lg 2/(\lg Nt(\text{number of cells at day4})-\lg No(\text{number of cells at day2}))]$.

RNA Seq and Data Analysis

Total RNA was isolated from primed hES cells, hEPS cells and naïve NSHM-hES cells, mES cells and mEPS cells using the RNeasy Mini Kit (Qiagen). RNA sequencing libraries were constructed using the NEBNext®Ultra™ RNA Library Prep Kit for Illumina® (NEB, USA). The fragmented and randomly primed 200-bp paired-end libraries were sequenced using Illumina HiSeq 2000. The gene expression levels were calculated as the FPKM (Fragments per Kilobase of transcript per Million mapped reads). In other experiments, generated sequencing reads were mapped against human genome build hg19 for human and GRCm38/mm10 for mouse using TopHat alignment software tools. The read counts for each gene were calculated, and the expression values of each gene were normalized using RPKM (Reads per Kilobases per Million reads).

The transcriptome reads were mapped using the TopHat2 program. Normalized differentially expressed (DE) genes were detected. The provided P value (Poisson distribution) corresponds to the differential gene expression test. Correction for false positive (type I) and false negative (type II) errors was performed using the FDR (False Discovery Rate) method. An FDR<0.01 and an absolute value of the log 2 ratio>1 were used as the threshold to declare gene expression differences as significant.

Gene ontology analysis of the DE genes was performed using the DAVID program (described in Huang, et al., *Nature Protocols*, 4:44-57 (2009)). Terms that had a P-Value of less than 0.01 were defined as being significantly enriched.

For clustering of the global expression profiles of transcripts in different samples, all of the transcripts expressed in at least one of the samples with FPKM≥0.1 were used. To minimize the potential influence of genetic backgrounds of different cell lines in clustering, the expression values from different cell lines were transformed into relative abundance values, which were generated by normalizing the expression values of each transcript to the mean of expression values within the same transcript across samples. The resulting expression matrix was subjected to hierarchical clustering (Spearman correlation, average linkage).

To compare EPS cells with other pluripotent cells, the published data of human reset PSCs, human 3iL hESCs, human naïve PSCs, human primed ESCs, mouse EpiSCs, mouse 2C-like cells and mouse ESCs were included. Bioinformatic analysis was restricted to the genes interrogated by each sample. For the expression profile of human reset PSCs, 3iL hESCs, and conventional PSCs published in Takashima et al. (2014) and Chan et al. (2013), raw sequencing reads (E-MTAB-2857) and (E-MTAB-2031) from ArrayExpress database were remapped and processed as described above. For the expression profile of human naïve PSCs and human primed ESCs published in Gafni et al. (2013) and Theunissen et al. (2014), normalized microarray data under GSE46872 and GSE59430 in the NCBI GEO database were downloaded and merged, respectively. For the expression profile of mouse ESC (GSM659549, GSM659550) and EpiSC (GSM659551, GSM659552, GSM659553, GSM659554) published in Najm et al. (2011), the normalized expression tables were downloaded and merged. For the expression profile of 2C-like cells published in Macfarlan et al. (2012), and the normalized expression data of 2C::tomato+ cells and 2C::tomato− cells (GSM8351954, GSM8351998) were downloaded and processed in the same manner as described above.

To compare EPS cells with embryonic preimplantation cells, the published data of human and mouse embryonic preimplantation cells were used (Tang, et al., *PLoS One*, 6:e21208 (2011); Yan, et al., *Nat. Struct. Mol. Biol.*, 20:1131-1139 (2013). The probesets of the same gene were collapsed into a single value to represent the gene by taking the mean value. Accounting for the platform and batch effect among the different datasets, the expression values from the published data and our data were recalculated by normalizing the original data to the mean values of its ES cell samples (primed hPSCs for human and mouse ESCs for mouse).

For subsequent analysis of gene expression, genes were retained in both datasets if they were expressed in at least one sample, using an RPKM>5 threshold (Blakeley, et al., *Dev.*, 142:3151-3156 (2015). Differentially expressed (DE) genes were detected by the package DESeq2 in the R software. An adjusted p-value <0.05 and an absolute value of the log 2 ratio>1 were used as the threshold for declaring gene expression differences as being significant.

Principal components analysis was performed using princomp function in the R stats package based on the covariance matrix. Expression levels normalized to embryo-derived PSC in each study were used to reduce the technical differences caused by different experiments and platforms as described above. Heatmaps were generated using pheatmap package in the R software.

RNA-seq and ChIP-seq data have been deposited in the Gene Expression Omnibus under the series accession number GSE68782.

Chromatin Immunoprecipitation (ChIP), Sequencing Library Preparation, Sequencing and Data Analysis.

ChIP was performed using the EZ-Magna ChIP A/G Kit (Millipore) according to the manufacturer's protocol. Anti-H3K27me3 (anti-trimethyl-Histone H (Lys27) (07-449, Millipore) and anti-H3K4me3 (anti-Histone H3 (trimethyl K4) (ab8580, Abcam) antibodies were used. Purified ChIP DNA was used to prepare Illumina multiplexed sequencing libraries. Libraries for Illumina sequencing were prepared following the Illumina 1 TruSeq DNA Sample Preparation v2 kit protocol. Amplified libraries were then size-selected using a 2% gel cassette in the Pippin Prep system from Sage Science set to capture fragments between 100 and 500 bp. Libraries with distinct TruSeq indexes were multiplexed by mixing at equimolar ratios and running together in a lane on the Illumina HiSeq 2500 for 100 bases in paired read mode. Bowtie software version 2.0 was used to align human reads to human reference genome hg19 (UCSC, February 2009). Only those reads that were uniquely aligned to the genome with up to no more than two mismatches were considered, for further analysis. Chromatin profiles were calculated over all RefSeq genes, using ngsplot to analyze the read densities between 2 kb upstream to TSS and 2 kb downstream to TES. Profiles of human samples represent mean and error bars of primed and hEPS cells. MACS version 2.0 (Model based analysis of ChIP-Seq) peak finding algorithm was used to identify regions of ChIP-Seq enrichment over background, and BAMPE Sequence Model was used to find peak, and selected significant peak using FDR<0.05. Finally, Hommer and R was used to annotate peak, to analyze the distribution of peak in gene function elements and genes and gene ontology related to the peaks, and KEGG (Kyoto Encyclopedia of Genes and Genomics) pathways.

Western Blot.

Whole-cell protein extracts were isolated from primed hES cells and hEPS cells using RIPA (Radio-Immunoprecipitation Assay) lysis buffer (P0013B; Beyotime) supplemented with protease inhibitor cocktail (78443; Thermo Fisher Scientific) and phosphatase inhibitor cocktail (78428; Thermo Fisher Scientific). Blots were incubated in 2% BSA (A1470; Sigma-Aldrich)/TBST in room temperature for 1 h, then incubated with the following antibodies in 5% BSA or 5% skimmed milk powder (P1622; Applygen)/TBST (Tris Base Saline buffer with 0.1% Tween-20) in 4° C. overnight: anti-p-STAT3(phospho-STAT(Signal transducer and activator of transcription) 3 (Tyr705) (9145S; Cell Signaling Technology), anti-STAT3 (sc-482; Santa Cruz), anti-GP (glycoprotein)130 (3732S; Cell Signaling Technology), anti-GSK-3β (AG751-1; Beyotime), anti-p-GSK-3β (Ser9) (9322S; Cell Signaling Technology), anti-PARP1 (sc-7150; Santa Cruz), anti-TBX3 (ab89220, Abcam), anti-GBX2 (sc-22230; Santa Cruz) and anti-β-ACTIN (A1978; Sigma).

For detecting MAPK pathways, human and mouse cells were used the same antibodies: ERK1/2 (AM076-1; Beyotime), p-ERK1/2 (AM071-1; Beyotime), JNK (AM7518-1; Beyotime), (AM7516-1; Beyotime), p38 (9212S; Cell Signaling Technology) and p-p38 (9215S; Cell Signaling Technology).

Secondary antibodies were anti-rabbit IgG, HRP (horseradish peroxidase)-linked antibody (7074S; Cell Signaling Technology) and anti-mouse IgG, HRP-linked antibody (7076S; Cell Signaling Technology), which were incubated 1 hour at room temperature with shaking. Blots were developed using BeyoECL Plus (P0018; Beyotime).

Quantitative PCR Analysis.

Total RNA from an entire well of cultured cells was isolated using the RNeasy Plus Mini Kit (QIAGEN). RNA was converted to cDNA using TransScript First-Strand cDNA Synthesis SuperMix (TransGen Biotech). PCR was conducted using Power SYBR® Green PCR Master Mix (Applied Biosystems) on an ABI Prism 7300 Sequence Detection System. The data were analyzed using the delta-delta CT method. The primers used for real-time PCR are listed in Table 2.

TABLE 2

Summary of PCR primers and shRNA sequences used in this study

| GENES | Forward (5' to 3') | Reverse (5' to 3') |
|---|---|---|
| qRT-PCR primers of human | | |
| PARP1 | CGGAGTCTTCGGATAAGCTCT (SEQ ID NO: 1) | TTTCCATCAAACATGGGCGAC (SEQ ID NO: 2) |
| TBX3 | CCCGGTTCCACATTGTAAGAG (SEQ ID NO: 3) | GTATGCAGTCACAGCGATGAAT (SEQ ID NO: 4) |
| GBX2 | GACGAGTCAAAGGTGGAAGAC (SEQ ID NO: 5) | GATTGTCATCCGAGCTGTAGTC (SEQ ID NO: 6) |
| CDX2 | CAGTCGCTACATCACCATCC (SEQ ID NO: 7) | TTTCCTCTCCTTTGCTCTGC (SEQ ID NO: 8) |
| GATA6 | CTCAGTTCCTACGCTTCGCAT (SEQ ID NO: 9) | GTCGAGGTCAGTGAACAGCA (SEQ ID NO: 10) |
| EOMES | CGCCACCAAACTGAGATGAT (SEQ ID NO: 11) | CACATTGTAGTGGGCAGTGG (SEQ ID NO: 12) |
| HAND1 | AACTCAAGAAGGCGGATGG (SEQ ID NO: 13) | CGGTGCGTCCTTTAATCCT (SEQ ID NO: 14) |
| OCT4 | GCTCGAGAAGGATGTGGTCC (SEQ ID NO: 15) | CGTTGTGCATAGTCGCTGCT (SEQ ID NO: 16) |
| NANOG | GCAGAAGGCCTCAGCACCTA (SEQ ID NO: 17) | AGGTTCCCAGTCGGGTTCA (SEQ ID NO: 18) |
| SOX17 | GTGGACCGCACGGAATTTG (SEQ ID NO: 19) | GGAGATTCACACCGGAGTCA (SEQ ID NO: 20) |
| GAPDH | CGAGATCCCTCCAAAATCAA (SEQ ID NO: 21) | ATCCACAGTCTTCTGGGTGG (SEQ ID NO: 22) |
| Single-cell qRT-PCR primers of human | | |
| OCT4 | CTTCTGCTTCAGGAGCTTGG (SEQ ID NO: 23) | GAAGGAGAAGCTGGAGCAAA (SEQ ID NO: 24) |

TABLE 2-continued

| | | |
|---|---|---|
| TBX3 | GTGCACCGAGCTGGAGG (SEQ ID NO: 25) | GCACGTCCTGGCCTCTC (SEQ ID NO: 26) |
| GBX2 | GACGAGTCAAAGGTGGAAGAC (SEQ ID NO: 27) | GATTGTCATCCGAGCTGTAGTC (SEQ ID NO: 28) |
| CDX2 | GAAACTCCTTCTCCAGCTCC (SEQ ID NO: 29) | GAACCTGTGCGAGTGGATG (SEQ ID NO: 30) |
| GATA3 | CTGCTTCATGGATCCCTACC (SEQ ID NO: 31) | GATGGACGTCTTGGAGAAGG (SEQ ID NO: 32) |
| EOMES | CACATTGTAGTGGGCAGTGG (SEQ ID NO: 33) | CGCCACCAAACTGAGATGAT (SEQ ID NO: 34) |
| DPPA3 | TAGCGAATCTGTTTCCCCTCT (SEQ ID NO: 35) | CTGCTGTAAAGCCACTCATCTT (SEQ ID NO: 36) |
| REX1 | GCCTTATGTGATGGCTATGTGT (SEQ ID NO: 37) | ACCCCTTATGACGCATTCTATGT (SEQ ID NO: 38) |
| TEAD4 | GCTCCACTCGTTGGAGGTAA (SEQ ID NO: 39) | CTTAGCGCACCCATCCC (SEQ ID NO: 40) |
| β-ACTIN | GACAGCAGTCGGTTGGAGCG (SEQ ID NO: 41) | GGGACTTCCTGTAACAACGCATC (SEQ ID NO: 42) |

| shRNA sequences | |
|---|---|
| PARP1 shRNA #1 | CCGGCCGAGAAATCTCTTACCTCAACTCGAGTTGAGGTAAGAGATTTCTCGGTTTTT (SEQ ID NO: 43) |
| PARP1 shRNA #2 | CCGGGCTTCACATATCAGCAGGTTACTCGAGTAACCTGCTGATATGTGAAGCTTTTT (SEQ ID NO: 44) |
| Scramble | CCGGCAACAAGATGAAGAGCACCAACTCGAGTTGGTGCTCTTCATCTTGTTGTTTTT (SEQ ID NO: 45) |

| Genes | Forward (5' to 3') | Reverse (5' to 3') |
|---|---|---|
| Eomes | CGGCAAAGCGGACAATAACA (SEQ ID NO: 46) | GGAGCCAGTGTTAGGAGATTC (SEQ ID NO: 47) |
| Elf5 | CTACAGTCCGCTGGTGCTGG (SEQ ID NO: 48) | GGTCACAGAAGGATGCGTTGG (SEQ ID NO: 49) |
| Parp1 | GGCAGCCTGATGTTGAGGT (SEQ ID NO: 50) | GCGTACTCCGCTAAAAGTCAC (SEQ ID NO: 51) |
| Ascl2 | CCGTGAAGGTGCAAACGTC (SEQ ID NO: 52) | CCCTGCTACGAGTTCTGGTG (SEQ ID NO: 53) |
| Hand1 | CTACCAGTTACATCGCCTACTTG (SEQ ID NO: 54) | ACCACCATCCGTCTTTTTGAG (SEQ ID NO: 55) |
| Plf | TCCTGGATACTGCTCCTACTACT (SEQ ID NO: 56) | GACCATTCCTCATTGCACACA (SEQ ID NO: 57) |
| Tpbpa | CACAGTAGCGAAAATGACCAGG (SEQ ID NO: 58) | TCCTCCTCTTCAAACATTGGGT (SEQ ID NO: 59) |
| Ctsq | CATTGCCAGTTGACAACACAAG (SEQ ID NO: 60) | ATAGCCTTCATTTCGCCAATCA (SEQ ID NO: 61) |
| PL2 | CCAACGTGTGATTGTGGTGTC (SEQ ID NO: 62) | CAGGCCATAGGTCCAAGCTG (SEQ ID NO: 63) |
| β-Actin | GGCACCACACCTTCTACAATG (SEQ ID NO: 64) | GTGGTGGTGAAGCTGTAGCC (SEQ ID NO: 65) |

| Genomic primers | | |
|---|---|---|
| Mouse Parp1 exon2 | GTACCACTTCTCCTGCTTCTGGA (SEQ ID NO: 66) | GGCCGTCTTCTTGACCTTCTG (SEQ ID NO: 67) |
| Mouse Parp1 exon7 | AAGAGCGACGCTTATTACTGTACTG (SEQ ID NO: 68) | CTTTGGAGTTACCCATTCCTTTC (SEQ ID NO: 69) |

TABLE 2-continued

| | | |
|---|---|---|
| Mouse Parp1 | CGGGTTCTGCTCATTCTCT TGGA (SEQ ID NO: 70) | CGCTTTGCTCTCGTGTTTCT CTCA (SEQ ID NO: 71) |
| gRNA sequences | | |
| Mouse Parp1 gRNA1 | CACCGCGAGTGGAGTACG CGAAGAG (SEQ ID NO: 72) | AAACCTCTTCGCGTACTCC ACTCGC (SEQ ID NO: 73) |
| Mouse Parp1 gRNA2 | CACCGCACCATGATGGCCA TGCGG (SEQ ID NO: 74) | AAACCCGCATGGCCATCAT GGTGC (SEQ ID NO: 75) |
| Mouse Parp1 gRNA3 | CACCGGGACTTTCCCATCG AACAT (SEQ ID NO: 76) | AAACATGTTCGATGGGAA AGTCCC (SEQ ID NO: 77) |
| Mouse Parp1 gRNA4 | CACCGTCAAGAAGACGGC CGAGGC (SEQ ID NO: 78) | AAACGCCTCGGCCGTCTTC TTGAC (SEQ ID NO: 79) |
| Quantitative PCR analysis for human mitochondrial DNA | | |
| Human-specific mitochondrial element | CGGGAGCTCTCCATGCATT T (SEQ ID NO: 80) | GACAGATACTGCGACATA GGGT (SEQ ID NO: 81) |
| Human-mouse conserved mitochondrial element | GCTAAGACCCAAACTGGG ATT (SEQ ID NO: 82) | GGTTTGCTGAAGATGGCGG TA (SEQ ID NO: 83) |

Genomic PCR and Human Mitochondrial PCR Assay

Total DNA of cells, embryos and placentas was isolated using the DNeasy Blood & Tissue Kit (QIAGEN). Genomic PCR was performed using EasyTaq PCR SuperMix (TRANSGEN BIOTECH). For detecting human specific mitochondrial DNA element by Q-PCR, 70 ng of total DNA per sample was used. The data were analyzed using the delta-delta CT method, which were first normalized to the values of human-mouse conserved mitochondrial DNA element. Then the relative expression values were further normalized to the values generated from control samples isolated from non-injected wild-type mouse tissues. The primers used for genomic PCR are listed in Table 2.

Quantitative PCR Analysis of Single Cell.

First, cells were disaggregated into a 1 single-cell suspension (1% BSA-PBS) with 0.5% Trypsin-EDTA, and then each cell was manually picked and transferred into a 0.2 ml PCR tube containing hypotonic lysis buffer. Secondly, the single cell cDNA was prepared as described before (Picelli, et al., Nature Protocols, 9:(171-181 (2014). The amplified cDNA product was diluted ten-fold as required by the qPCR template. Quantitative PCR analysis was conducted using KAPA SYBR® FAST qPCR Kit on a Bio RAD CFX Connect Real-Time System. The primers used for real-time PCR are listed in Table 2.

RNAi.

PARP1 knockdown was achieved using shRNA lentiviral vectors (Sigma-Aldrich). shRNA sequences are listed in Table 2. hEPS cells were transfected with these vectors respectively and cultured for 3 passages before analysis.

Generation of Parp1 Knockout mEPS Cell Lines

Guide RNA sequences were cloned into the plasmid px330 (Addgene). Px330 containing gRNAs were co-transfected into digested single mEPS cells by nucleofection (4D-Nucleofector™ System, Lonza). Single colonies were picked and expanded individually. Genomic DNA of colonies were extracted using the DNeasy Blood & Tissue Kit (QIAGEN), which was further analyzed by genomic PCR. Colonies with the deletion of exon 1 and exon 2 of Parp1 locus were identified.

Results and Discussion

Two small molecules, (S)-(+)-Dimethindene maleate (DiM) and Minocycline hydrochloride (MiH), were found to support dome-shaped hES colony formation under this condition morphologically resembled mouse embryonic stem (ES) cells. After further combination and testing of these small molecules, a new treatment combination named LCDM was established, which contained hLIF, CHIR99021, DiM, and MiH (FIG. 1A). Under this treatment combination, cell lines morphologically resembling mouse ES cells can be generated by the conversion of primed hES cells (data not shown), cells derived directly from blastocysts (data now shown), or generated by somatic reprogramming with pluripotency factors (data not shown). LCDM-supported cells showed the ability to differentiate into three embryonic germ layers in both in-vitro differentiation and in-vivo teratoma formation (data not shown and Table 3).

TABLE 3

Summary of established human and mouse extended pluripotent stem cells

| Cell Line | Species | RT-PCR | RNA-SEQ | IF | EB | Teratoma | Karyotype | Long term culture |
|---|---|---|---|---|---|---|---|---|
| H1-EPS | *H | Y | Y | Y | Y | Y | Y | >60 passages |
| H9-EPS | #H | Y | — | Y | Y | Y | Y | >60 passages |
| ES1-EPS | **H | Y | Y | Y | Y | Y | Y | >60 passages |
| ES2-EPS | **H | Y | — | Y | Y | Y | Y | >30 passages |

TABLE 3-continued

Summary of established human and mouse extended pluripotent stem cells

| Cell Line | Species | RT-PCR | RNA-SEQ | IF | EB | Teratoma | Karyotype | Long term culture |
|---|---|---|---|---|---|---|---|---|
| IPS1-EPS | ##H | Y | — | Y | Y | Y | Y | >60 passages |
| HSF6-EPS | ##H | Y | — | Y | Y | Y | Y | >20 passages |
| 0227E-EPS | *H | Y | — | Y | Y | Y | Y | >40 passages |
| mc6-1 | **M | Y | Y | Y | — | Y | Y | >70 passages |
| OG6-3 | **M | Y | Y | — | — | — | — | >10 passages |
| OG6-4 | **M | Y | — | Y | — | Y | — | >20 passages |
| TT2-6 | ***M | Y | — | Y | Y | Y | — | >70 passages |
| mc6-4 | **M | Y | — | — | — | Y | — | >20 passages |
| C1-EPS 2# | **M | — | — | Y | Y | Y | — | >20 passages |
| C1-EPS 3# | **M | — | — | Y | Y | Y | — | >20 passages |
| C1-EPS 12# | **M | — | — | Y | Y | Y | — | >20 passages |
| C1-EPS 17# | **M | Y | — | Y | Y | Y | — | >20 passages |
| C1-EPS 18# | **M | — | — | Y | Y | Y | — | >20 passages |
| C1-EPS 19# | **M | — | — | Y | Y | Y | — | >20 passages |

H = Human;
M = mouse;
Y = Yes;
*source is primed hES;
**source = Blastocyst;
source = fibroblast;
***source = TT2 mES;
— = not analyzed.

These cells could be robustly expanded following trypsinization into single cells and showed a normal karyotype after more than 50 passages (Data not shown and Table 3). Therefore, the LCDM condition supported the generation of a stable population of human stem cells with pluripotent differentiation potentials, which morphologically resemble mouse ES cells.

Figure 2A:
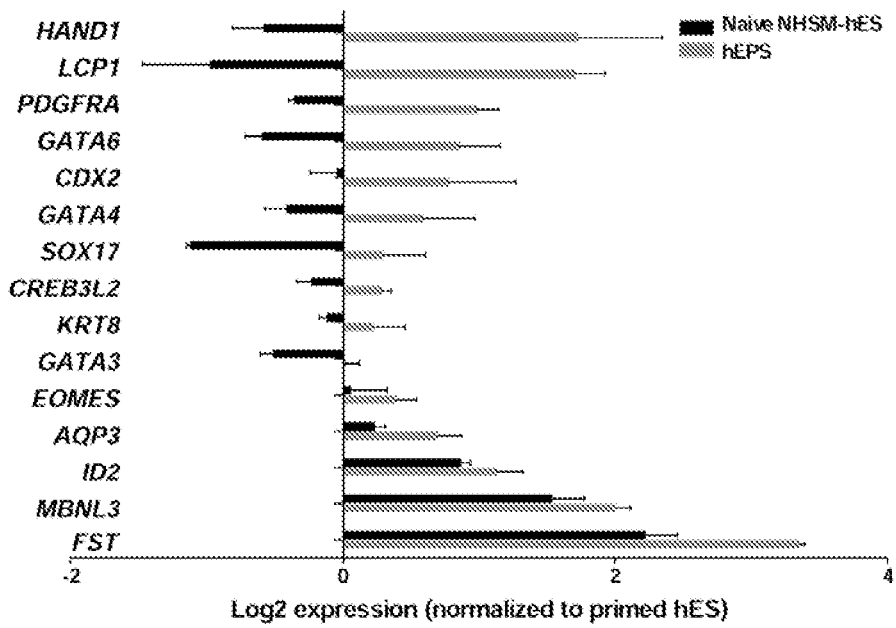
FIG. 2A shows representative relative transcription levels of extraembryonic genes in primed hES (n=4, biological replicates), naïve NHSM-hES (n=4, biological replicates) and hEPS (n=4, biological replicates) cells. For each sample, the gene expression values derived from RNA-seq are normalized to the average values of corresponding genes in primed hES cells. Center values indicate mean. Error bars indicate s.d.
Figure 2B:
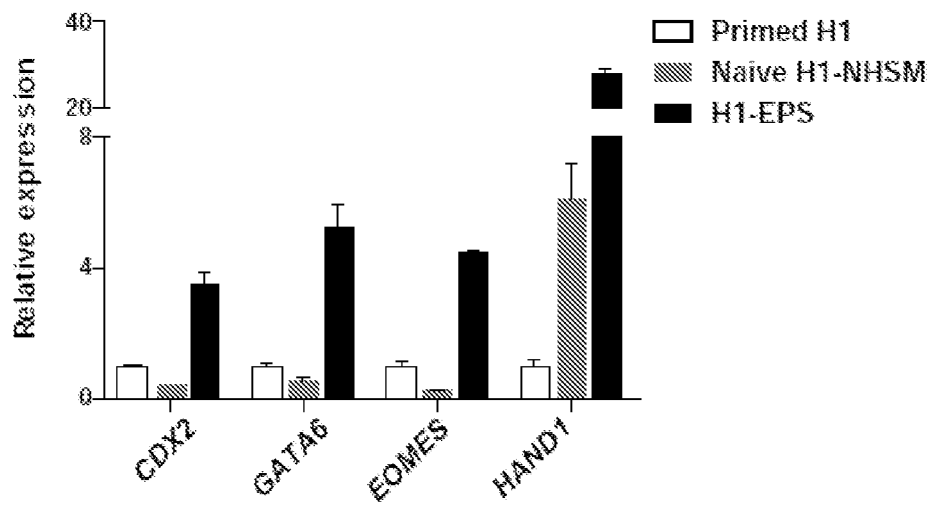
FIGS. 2B and 2C show Q-PCR analysis of selected extraembryonic gene expression in hEPS cells (H1-EPS, H9-EPS), primed hES cells (H1, H9), and naïve hES cells (H1-NHSM, H9-NHSM). For each sample, gene expression values are normalized to that in original primed H1 and H9 cells separately. Center values indicate mean. Error bars indicate s.d. (n=2, technical replicates).
Figure 2C:
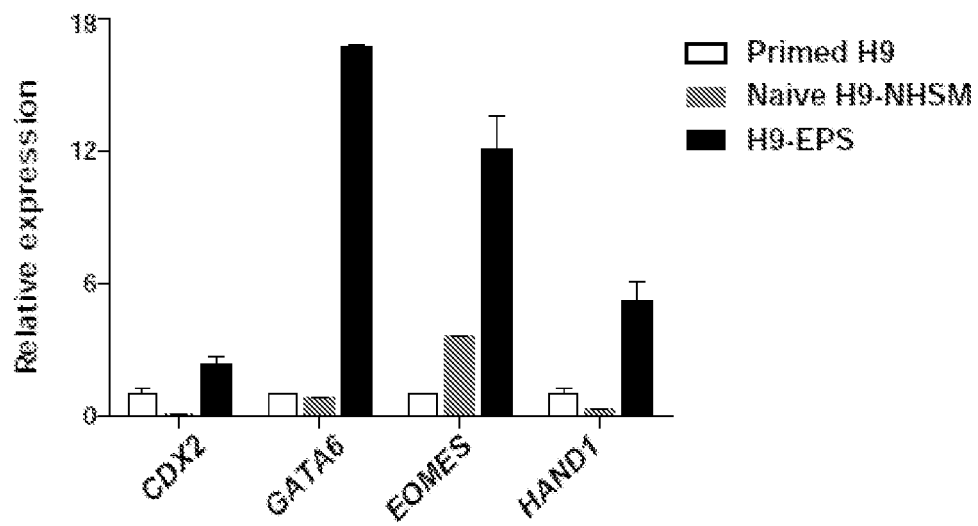
Figure 2D:
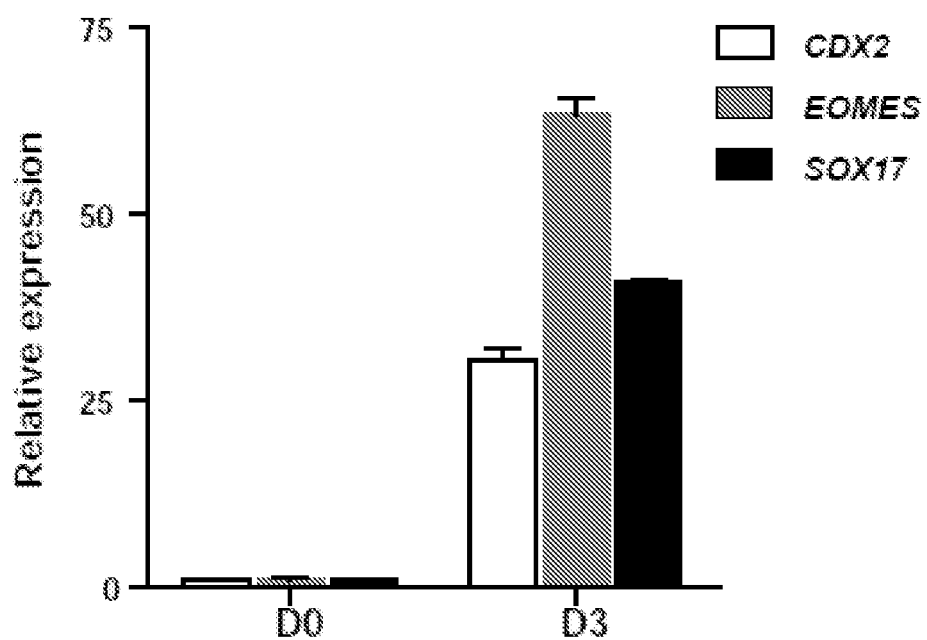
FIG. 2D represents Q-PCR (quantitative polymerase chain reaction) analysis showing the expression of extraembryonic genes in hEPS cells and in differentiated EB (embryoid body) cells derived from hEPS cells. D0: hEPS cells collected before EB formation assay; D3: hEPS derived cells collected on day 3 of EB formation. Gene expression values are normalized to D0 cells. Center values indicate mean. Error bars indicate s.d. (n=2, technical replicates).
Figure 3A:
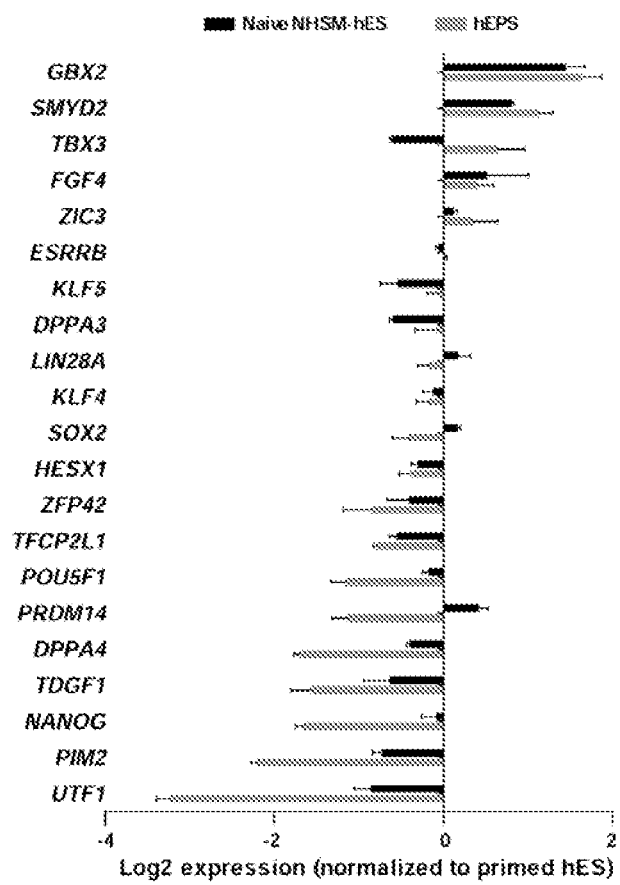
FIG. 3A shows relative transcript levels of representative pluripotency-related genes in primed hES (n=4, biological replicates), hEPS (n=4, biological replicates) and naïve NHSM-hES (n=4, biological replicates) cells. For each sample, the expression values derived from RNA-seq are normalized to the mean expression values in primed hES cells. Center values indicate mean. Error bars indicate s.d.
Figure 3B:
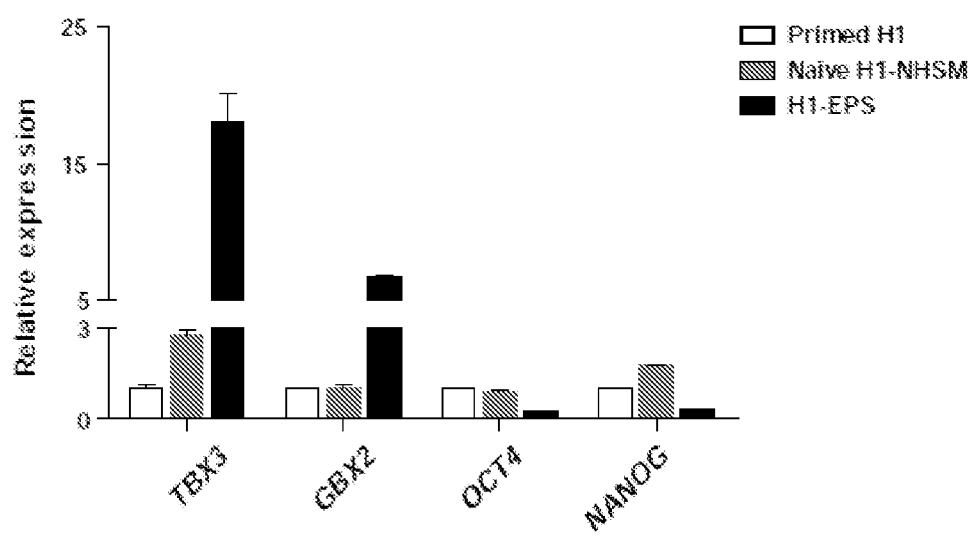
FIGS. 3B and 3C show Q-PCR analysis of selected pluripotency gene expression in hEPS cells (H1-EPS, H9-EPS), primed hES cells (H1, H9), and naïve NHSM-hES cells (H1-NHSM, H9-NHSM). For each sample, gene expression values are normalized to that in original primed H1 and H9 cells separately. Center values indicate mean. Error bars indicate s.d. (n=3, technical replicates).
Figure 3C:
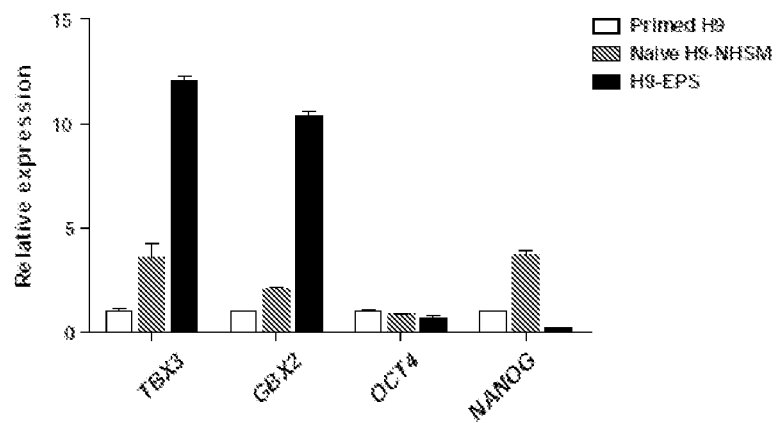
Figure 3D:
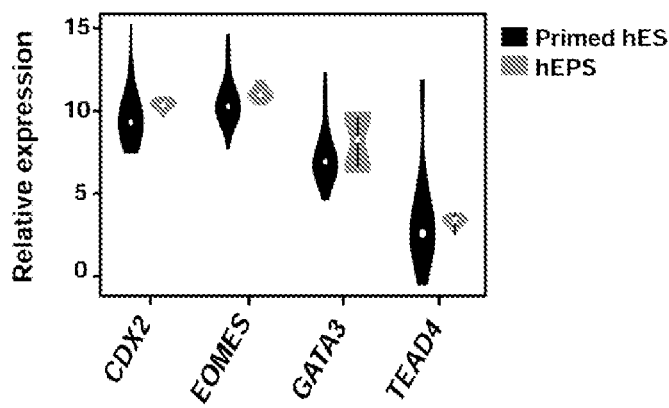
FIGS. 3D and 3E show the frequency distribution of expression values from single-cell qPCR analysis of the hEPS (n=16, biological replicates) and primed hES cells (n=25, biological replicates) shown as a violin plot for each indicated genes. For comparison, expression values are represented as the ΔCT values plus 20. White circles indicate median values of gene expression values for each sample.
Figure 3E:
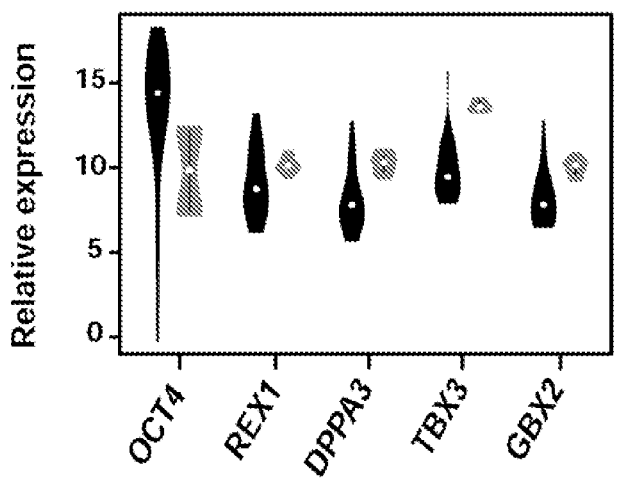

Because hEPS cells exhibit extraembryonic potential, the expression of extraembryonic markers in these cells was examined (FIG. 2A and FIG. 2B-C). Multiple extraembryonic genes, such as CDX2 (by 2 to 3 fold), GATA6 (by 2.5 fold), HAND1 (by 8 fold) and EOMES (by 1.5 fold), were upregulated in hEPS cells compared with either primed hES or naïve NHSM-hES cells (FIG. 2C and FIG. 2D-E). Single-cell analysis indicated that cell-to-cell variation in the expression of these genes was lower in hEPS cells than that in primed hES cells (data not shown), suggesting that the increase of extraembryonic gene expression in hEPS cells does not arise from a subset of cells indicating that the EPS cells are stably maintained. Furthermore, the expression of representative extraembryonic markers (COX2, EOMES, and SOX17) in hEPS cells was orders of magnitude lower (CDX2, 30 folds lower; EOMES, 60 folds lower; SOX17, 41 folds lower) than the expression of these markers in differentiated cells derived from hEPS cells on the mRNA level (FIG. 2D), which could not be detected using immunofluorescence on the protein level (data not shown). Therefore, these data show that the mRNA basal activity of extraembryonic genes is upregulated in hEPS cells. Pluripotency marker gene expression in hEPS cells was further analyzed. Immunofluorescence analysis showed that pluripotency marker genes, such as OCT4, NANOG, and SOX2, were expressed in hEPS cells (data not shown). However, compared with primed hES and naïve NHSM-hES cells, several pluripotency genes, such as NANOG, OCT4, and UTF1, were downregulated in hEPS cells (FIG. 3A-3C). Meanwhile, other pluripotency genes, such as TBX3 and GBX2, were upregulated (FIG. 3A-3C and data not shown). Notably, the mRNA expression of several pluripotency marker genes, including OCT4, REX1, DPPA3, TBX3, and GBX2, was more homogenous in hEPS cells than that in primed hES cells (FIG. 3D-3E). Taken together, these data suggest that hEPS cells possess several unique molecular features compared with primed hES or naïve NHSM-hES cells.

The epigenetic features of hEPS cells were next examined by analyzing the genome-wide distribution of H3K4me3 and H3K27me3 marks, which represents active and inhibitory epigenetic states of chromatin, respectively. Compared with primed hES cells, hEPS cells showed a global decrease in H3K27me3 and H3K4me3 levels (FIG. 4A-4B). Notably, the decrease in H3K27me3 was observed in the genomiclocus of extraembryonic markers such as CDX2, GATA4, GATA6, and EOMES (data not shown), which is consistent with the upregulation of the basal mRNA activity of extraembryonic genes. Meanwhile, several naïve pluripotency-related genes, including GBX2, TBX3, and LIFR, showed increased H3K4me3 and decreased H3K27me3 in hEPS cells (data not shown). Interestingly, previous study showed that naïve NHSM-hES cells also exhibited the global reduction of both H3K4me3 and H3K27me3 levels compared with primed hES cells (Gafni, et al., Nature, 504(7479): 282-6 (2013)). Therefore, similar to naïve NHSM-hES cells, hEPS cells showed a tendency to reduce both inhibitory and active epigenetic landmarks globally, which distinguishes the epigenetic state of hEPS cells from that of primed hES cells.

When compared to primed hES cells, hEPS cells showed activation of LIF signaling determined by measuring the levels of GP130, STAT3 and -p-STAT3, protein levels using Western Blot analysis. The data showed upregulation of these protein levels in hEPS cells, when compared to primed hEPS. In addition, GSK3β phosphorylation was decreased in hEPS cells as determine by Western blot analysis (data not shown).

To determine whether the derivation of LCDM-cells is specie-specific, experiments were conducted to examine whether LCDM-cells could also be established in mice (mEPS), rat and pig. Mouse LCDM-cells were successfully established from blastocysts using the LCDM condition (data not shown). LCDM-cells were also successfully established from rat and pig (data not shown). Analysis of pluripotency markers shows that the LCDM-cells from mice expressed pluripotency marker genes such as NANOG, KLF4, SALL4 and SOX2; the LCDM-cells from pig expressed SOX2, REX1 and OCT4 (data not shown). These cells showed the ability to generate all three embryonic germ layers (data not shown) and maintained a normal karyotype (data not shown). In addition, mouse LCDM-cells also generated chimeras with germline transmission and permitted mouse generation through tetraploid complementation (data not shown).

Figure 4D:
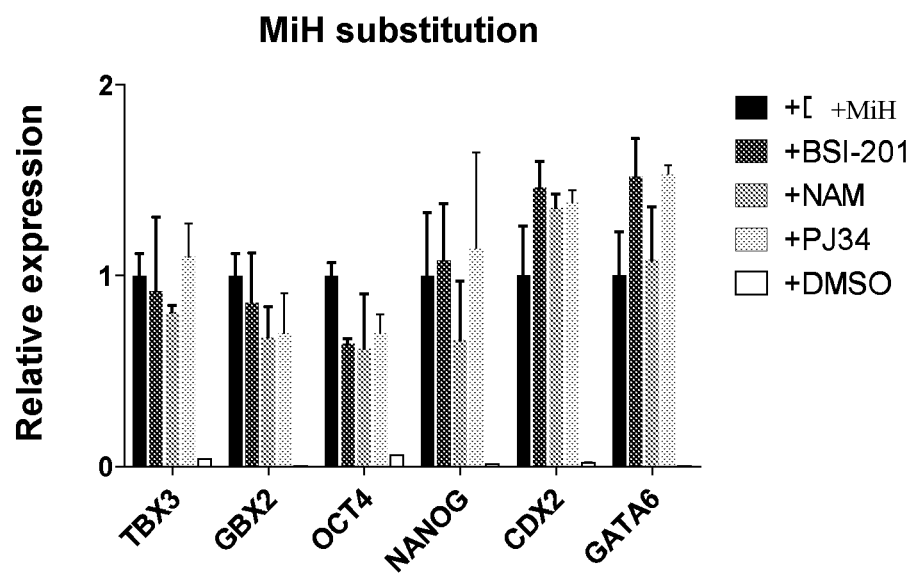

While examining the in vivo developmental potential of mouse LCDM-cells using the chimera assay, besides the embryonic (Em) tissues, the integration of LCDM-mES-derived cells into extraembryonic (ExEm) tissues was observed, such as the placenta and yolk sac (24/60 recovered E12.5 conceptuses) (data not shown). This is in contrast to mES cells that showed embryonic chimerism (31/78 recovered embryos) (data not shown and FIG. 4F) and the ability to integrate into the yolk sac but unable to contribute to the placenta (0/78 recovered conceptuses), results consistent with a previous report (Beddington, et al., *Dev.*, 105:733-737 (1989). These results suggest that LCDM-mES cells may have acquired an extended developmental potency toward ExEm lineages, and hereafter we designate them as extended pluripotent stem cells, or EPS cells.

To unequivocally demonstrate mEPS cells' developmental potency, a highly stringent assay was employed to examine the chimera forming ability of a single donor cell. To this end, a single fluorescent-labeled mEPS cell was injected into 8-cell stage mouse embryo, and its chimeric contribution was examined after 60 hours of in-vitro culture. Notably, 33.2% (86/259) of recovered blastocysts showed concomitant differentiation of a single mEPS cell to both the trophectoderm (TE) and inner cell mass (ICM) in chimeric blastocysts (FIG. 4G and Table 6), which was evidenced by the co-expression of tdTomato with TE markers CDX2 or GATA3 in the outer layer of blastocysts, and with pluripotency markers OCT4 or NANOG in the ICM (data not shown).

TABLE 6

| Cell lines | Cell type | | | |
|---|---|---|---|---|
| | EPS | | Naïve | |
| | TT2-6 | mc6-1 | TT2-2i | mc2i-1 |
| Injected embryos | 135 | 133 | 81 | 61 |
| Recovered blastocysts | 133 | 126 | 78 | 60 |
| Only contribute into ICM | 33 | 23 | 25 | 4 |
| Only contribute into TE | 7 | 8 | 0 | 0 |
| Contribute into both TE and ICM | 43 | 43 | 0 | 0 |

Consistently, single mES derivatives did not contribute to both TE and ICM (0/138 recovered blastocysts).

Single mEPS-derived chimeric conceptuses beyond the preimplantation stage were analyzed in separate experiments, including E10.5, E12.5 and E17.5, and the integration of single-donor mEPS cell derivatives in both Em and ExEm tissues in E10.5 (21/90 recovered conceptuses) and E12.5 (10/63 recovered conceptuses) conceptuses was observed (Table 8).

TABLE 8

Summary of Chimeric assays analyzed at either E10.5, E12.5 or E17.5 based on single mEPS cell injection

| | Cell type | | | | | | | |
|---|---|---|---|---|---|---|---|---|
| | EPS | | | | | | Naïve | |
| | Detected stage | | | | | | | |
| | E10.5 | | E12.5 | | E17.5 | | E10.5 | |
| | Cell lines | | | | | | | |
| | TT2-6 | mc6-1 | TT2-6 | mc6-1 | TT2-6 | mc6-1 | TT2-2i | mc2i-1 |
| Injected embryos | 127 | 58 | 133 | 70 | 134 | 98 | 35 | 46 |
| E10.5*/E12.5‡/E17.5§ | 66 | 24 | 35 | 28 | 55 | 39 | 10 | 34 |
| Only contribute into Em | 0 | 0 | 0 | 5 | 0 | 0 | 0 | 0 |
| Only contribute into ExEm | 0 | 0 | 0 | 1 | 0 | 0 | 0 | 0 |
| Contribute into both Em and ExEm | 11 | 10 | 5 | 5 | 8 | 5 | 0 | 0 |

Taken together, these results indicate that the LCDM condition also supports the establishment of EPS cells in mice.

To functionally evaluate the blastocyst derivatives of a single mEPS cell, ES and trophoblast stem (TS) cell derivation (Tanaka, et al., Science, 282:2072-2075 (1998) were tested next. To this end, chimeric embryos with the contribution of mEPS-derived cells into both TE and ICM were used for derivation of ES and TS cell lines simultaneously. Chimeric blastocysts with contribution of single mEPS-derived cells into both TE and ICM were seeded and further passaged into 2i and TS medium (as discussed in the methods above), which successfully supported the derivation of Tdtomato$^+$ mEPS-derived ES (EPS-ES) and TS (EPS-TS) colonies simultaneously. Both ES (EPS-ES) and TS (EPS-TS) cells could be derived from the same chimeric blastocysts. (data not shown and Table 9).

TABLE 9

TS and ES derivation from a same chimeric embryo

|  | EPS |
| --- | --- |
| Seeded embryos | 25 |
| Established cell lines (ES/TS) | 7/7 |

As a control, a mES cell line (2i-ES) was also established from a chimeric blastocyst developed from an 8-cell embryo injected with multiple Tdtomato+ mES cells (data not shown). 10-15 Tdtomato-labeled mES cells were microinjected into one mouse 8-cell embryo and cultured for an additional 60 hours. The chimeric embryos were seeded into ES or TS derivation medium respectively. In contrast to mEPS cells, no Tdtomato+ TS-like colonies could be established using blastocyst (0/48) derived from 8-cell embryos injected with mES cells. Only ES (2i-ES) cells could be derived (data not shown).

EPS-ES cells expressed pluripotency markers OCT4 and NANOG, but not the TS markers CDX2 and EOMES (data not shown); EPS-ES cells also expressed SOX2. EPS-ES cells only contributed to the ICM of the blastocyst (data not shown), and gave rise to embryonic tissues but not placenta in chimeric embryos (data not shown). On the other hand, EPS-TS cells expressed typical TS markers (EOMES and CDX2) but not the pluripotency markers OCT4 and NANOG (data not shown). EPS-TS also expressed SOX2. EPS-TS cells only integrated into the TE layer in blastocysts (data not shown) and exclusively contributed to placental tissue in chimeric embryos (data not shown).

Figure 5A:
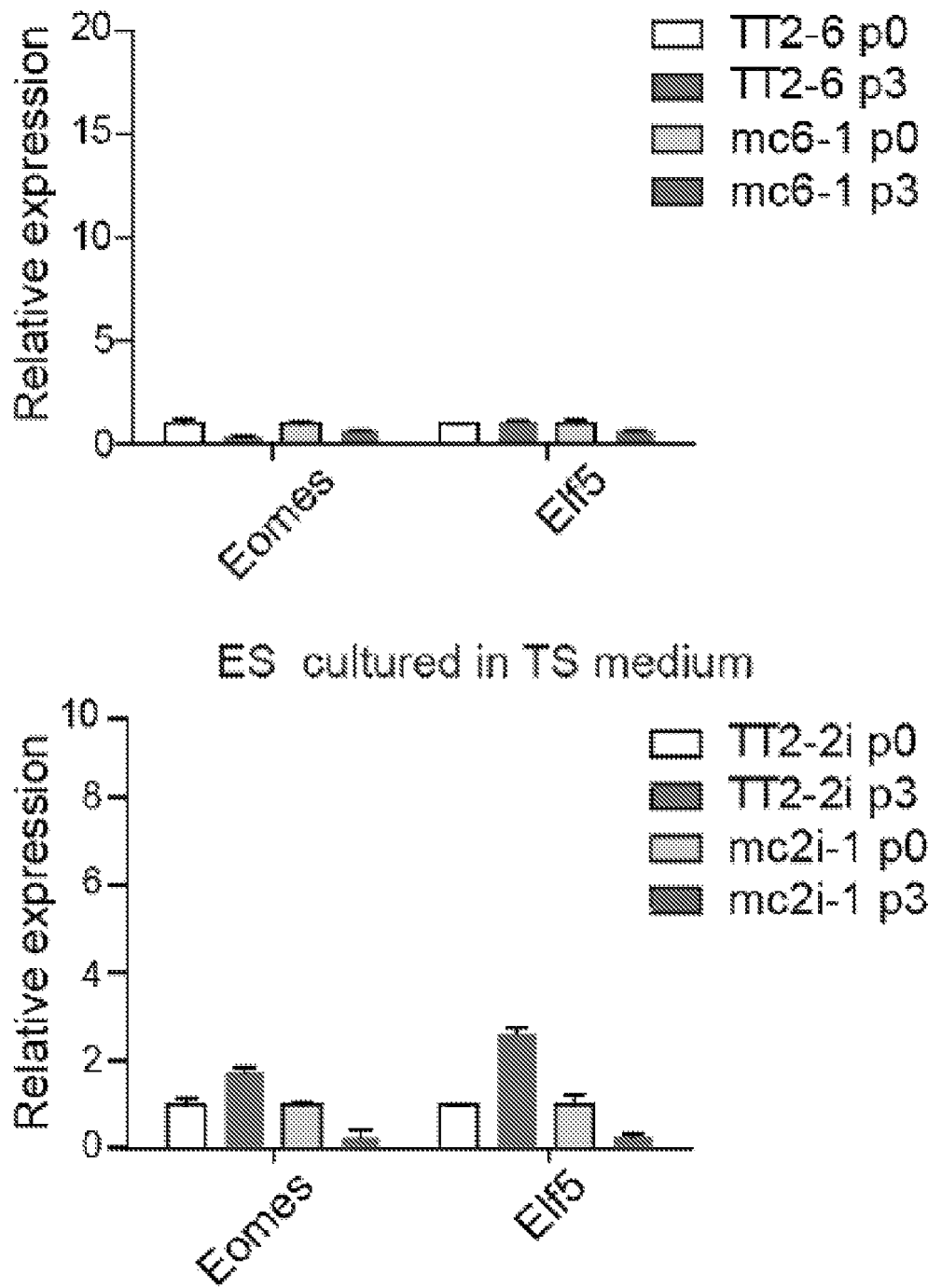
FIG. 5A shows relative expression of representative TS marker genes in cells cultured in traditional TS medium. mEPS cells cultured in LCDM condition (TT2-6 p0 and mc6-1 p0) or mES cells cultured in 2i condition (TT2-2i p0 and mc2i-1 p0) were used as controls separately. Similar results were obtained in at least three independent experiments. Error bars indicate s.d. (n=3).

To exclude the possibility that EPS cells could be directly converted into TS cells in TS medium, mEPS cells were cultured in TS medium for 3 passages and the levels of TS markers determined. mEPS cells cultured in LCDM condition (TT2-6 p0 and mc6-1 p0) or mES cells cultured in 2i condition (TT2-2i p0 and mc2i-1 p0) were used as controls separately. The data shows that TS-cultured mEPS cells did not upregulate TS markers (FIG. 5A and data not shown) and still maintained NANOG expression (data not shown). These results support the conclusion that EPS-TS is derived from EPS-differentiated TS cells rather than through direct conversion. Collectively, these data demonstrate the developmental potential of a single mEPS cell towards both ICM and TE lineages during preimplantation mouse development.

FACS analysis further confirmed the wide-spread integration of single mEPS-derived cells in E10.5 chimeric embryo, yolk sac and placenta (Table 10).

TABLE 10

Summary of FACS analysis of the percentages of single mEPS-derived chimeric cells in the E10.5 chimeric conceptuses

| | Single cell injection | | |
| --- | --- | --- | --- |
| | Embryo | Yolk sac | Placenta |
| 1# | 62.7% | 36.2% | 7.76% |
| 2# | 28.0% | 25.9% | 5.4% |
| 3# | 17.8% | 16.9% | 2.41% |
| 4# | 21.5% | 25.6% | 3.45% |
| 5# | 71.2% | 60.4% | 13.0% |

Figure 5B:
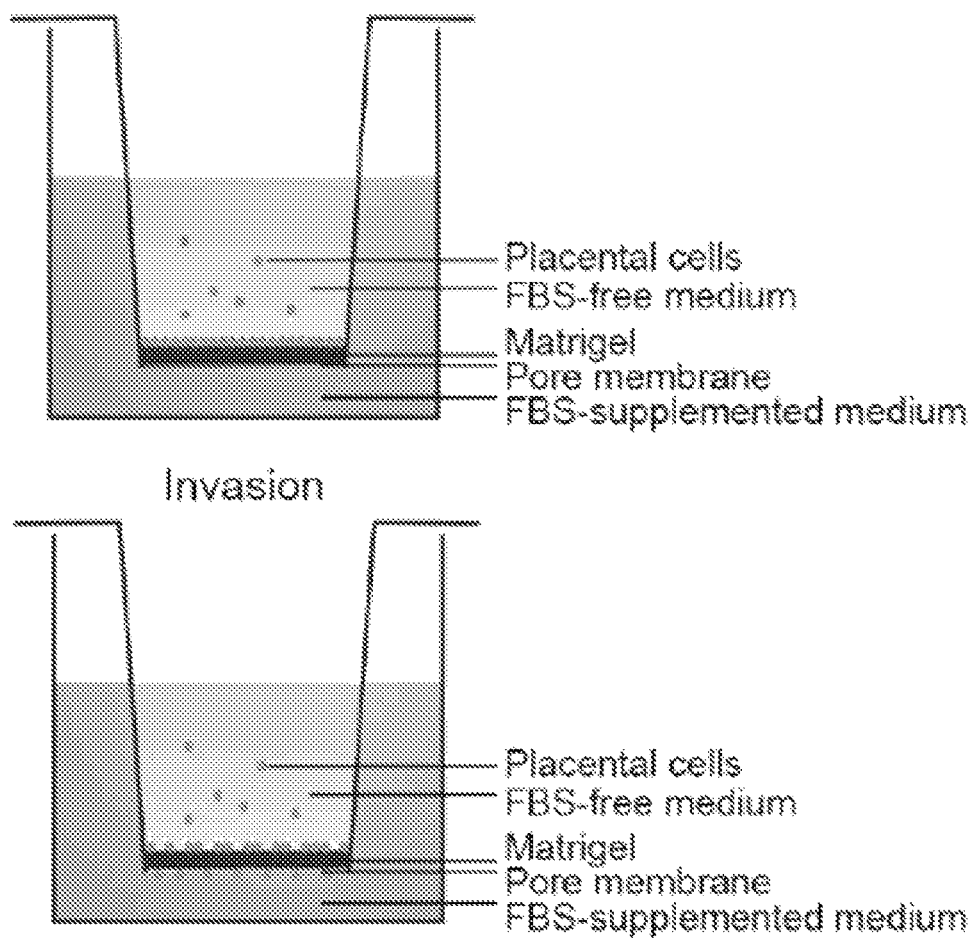
FIG. 5B is a schematic diagram of the Transwell-based invasive assay.
Figure 5C:
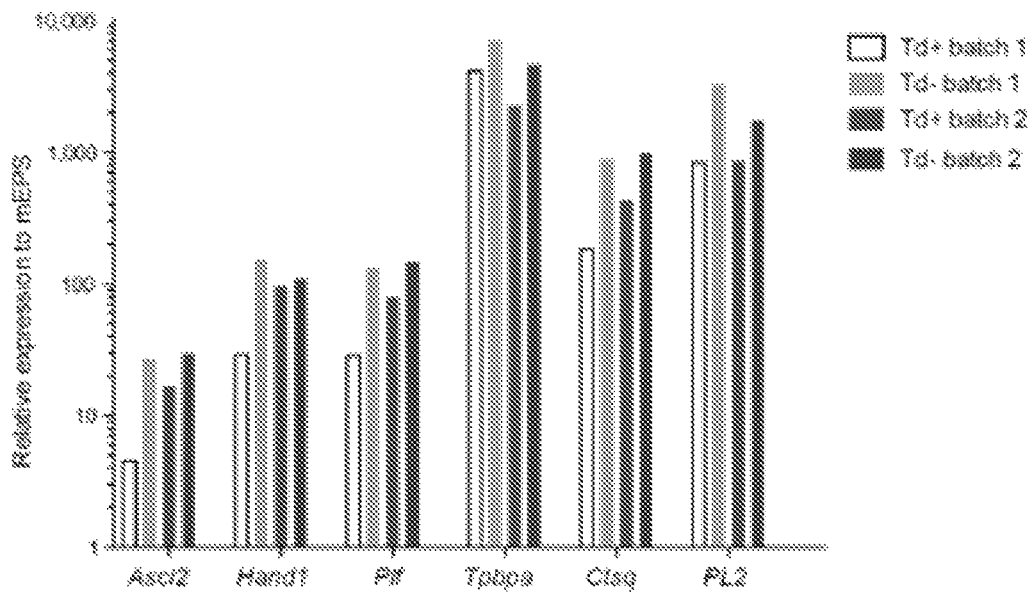
FIG. 5C shows expression of trophoblast marker genes in mEPS-derived cells in the E17.5 placental tissues. Two batches of samples were analyzed. Tdtomato (Td) positive cells were purified using FACS. The expression of trophoblast markers in these cells were analyzed and compared with the original EPS cells (TT2-6) and Td negative host placental cells.

By contrast, no E10.5 chimeras generated by injection of single mES cells (0/44 recovered embryos) were obtained (Table 8). Notably, single mEPS-derived cells integrated into the trophoblast layers of the chimeric placentas, and expressed the trophoblast marker CK8 (data not shown). These cells were also observed in the layers of trophoblast giant cells (TGCs) and spongiotrophoblasts, and expressed TGC marker PLF (PROLIFERIN) and spongiotrophoblast marker TPBPA respectively (data not shown). Single mEPS-derived cells also chimerized both the Em and ExEm tissues in late-gestation E17.5 conceptuses (13/94 recovered conceptuses) (data not shown and Table 8), and the percentage of a single mEPS cell derivatives contributed to the E17.5 chimeric placentas could be up to 19% (data not shown). To further evaluate the functionality of single EPS-derived trophoblasts, their invasive ability was tested using the transwell-based invasive assay (FIG. 5B), because one of the most prominent functional features of trophoblasts is their ability to invade the decidualized uterus. Tdtomato+ single mEPS-derived placental cells, which expressed the trophoblast markers CK8 or CK7, were able to migrate through the membrane pores and reached the bottom surface of the membrane (data not shown), highlighting their invasive nature. Furthermore, the mRNA expression of multiple trophoblast markers were significantly upregulated in mEPS-derived placental cells when compared to mEPS cells (FIG. 5C).

Further experiments tested whether it is possible to obtain single mEPS-derived postnatal chimeric mice, which is regarded as the golden standard for demonstrating genuine pluripotency (De Los Angeles, Nature, 525:569-478 (2015). Of 87 born pups, 43 single mEPS-derived chimeras (49.4%) were obtained among which 24 showed high degree of chimerism as judged by coat color (data not shown and Table 11).

TABLE 11

Chimeric level from different pups

| | | | Chimeric level | | |
| --- | --- | --- | --- | --- | --- |
| Cell lines | Pups | Chimera | A | B | C |
| C1-EPS 2# | 3 | 2 | 1 | 0 | 1 |
| C1-EPS 3# | 14 | 6 | 0 | 3 | 3 |
| C1-EPS 12# | 33 | 15 | 0 | 7 | 8 |
| C1-EPS 17# | 14 | 8 | 0 | 3 | 5 |
| C1-EPS 18# | 5 | 2 | 0 | 0 | 2 |
| C1-EPS 19# | 18 | 10 | 1 | 4 | 5 |

Taken together, these data demonstrate the bona fide pluripotency of EPS cells and their chimeric competency to both Em and ExEm lineages at the single cell level.

The chimera forming ability of mEPS cells led to further experiments to examine whether hEPS cells could also generate interspecies human-mouse conceptuses. A single fluorescent-labeled hEPS cell was injected into an 8-cell stage mouse embryo (data not shown), and its chimeric contribution examined after 60 hours of in-vitro culture by co-staining with TE (CDX2, GATA3) and ICM (OCT4, NANOG) markers. The results showed concomitant differentiation of a single hEPS cell into cells expressing TE or ICM markers respectively (51/345 recovered embryos, 14.7%) in chimeric blastocysts (data not shown, Tables 12-15). As the control, primed hPSCs could not form chimeric blastocysts after single cell injection (0/143 recovered embryos) (data not shown, Tables 12, 13a, 13b and 13c), which is consistent with previously reported poor chimerism of primate primed PSCs (Gafni, et al., Nature, 504:282-(2013); Tachibana, et al., Cell, 148:285-295 (2012); James, et al., Dev. Biol., 295:90-102 (2006)).

TABLE 12

| Cell lines | Injected embryos | Recovered embryos | Contribute into both TE and ICM |
|---|---|---|---|
| ES1-EPS | 140 | 129 | 22 |
| iPS-EPS | 172 | 155 | 22 |
| 0227E-EPS | 67 | 61 | 7 |
| ESI-Primed | 67 | 65 | 0 |
| iPS-Primed | 63 | 59 | 0 |
| 0227E-primed | 20 | 19 | 0 |

TABLE 13a

Summary of human-mouse chimeric assay by injection a single hEPS cell into 8-cell embryo

| | Classes | | | | | |
|---|---|---|---|---|---|---|
| | EPS | | | Primed | | |
| | Cell lines | | | | | |
| | ES1-EPS | iPS1-EPS | 0227E-EPS | ES1-Primed | iPS1-Primed | 0227E-Primed |
| Number of cells injected in each embryo | 1 | 1 | 1 | 1 | 1 | 1 |
| Injected embryos | 140 | 172 | 67 | 67 | 63 | 20 |
| Recovered blastocysts | 129 | 155 | 61 | 65 | 59 | 19 |
| Only contribute into ICM | 14 | 22 | 7 | 0 | 0 | 0 |
| Only contribute into TE | 9 | 14 | 1 | 0 | 0 | 0 |
| Contribute into both TE and ICM | 22 | 22 | 7 | 0 | 0 | 0 |
| Detection | GFP*, HN§ | Td‡, HN§ | HN§ | HN§ | HN§ | HN§ |

*GFP: injected cells were GFP-labeled, and detected using fluorescence microscope
‡Td: injected cells were Tdtomato-labeled, and detected using fluorescence microscope
§HN: immunostaining with an anti-human nuclei antibody
In this assay, the EPS cell lines used were at these passages as listed below:
ES1-EPS: from passage 12 to passage 62
iPS1-EPS: from passage 21 to passage 60
0227E-EPS: from passage 15 to passage 28

TABLE 13b

Summary of tested embryos and positive embryos based on a sensitive human mitochondrial PCR assay with a detection threshold of approximately 1 human cell for every 10,000 mouse cells (the middle and lower tables).

| | Embryos | Placentas |
|---|---|---|
| Recovered hEPS-derived E10.5 conceptuses | 118 | 136 |
| Positive conceptuses¶ | 42 | 24 |
| 1/10,000-1/1,000 | 37 | 23 |
| 1/1,000-1/100 | 4 | 1 |
| 1/100-1/10 | 1 | 0 |

¶Positive conceptuses: the chimeric level is higher than 1/10,000 (human cell/mouse cell).

TABLE 13C

| | EPS | Primed |
|---|---|---|
| Recovered E10.5 conceptuses | 54 | 54 |
| Contribute to embryo | 24 | 0 |
| Contribute to placenta | 11 | 0 |
| Contribute to both embryo and placenta | 9 | 0 |

Threshold for human cell contribution: 1/10,000 (human cell/mouse cell)

Figure 1B:
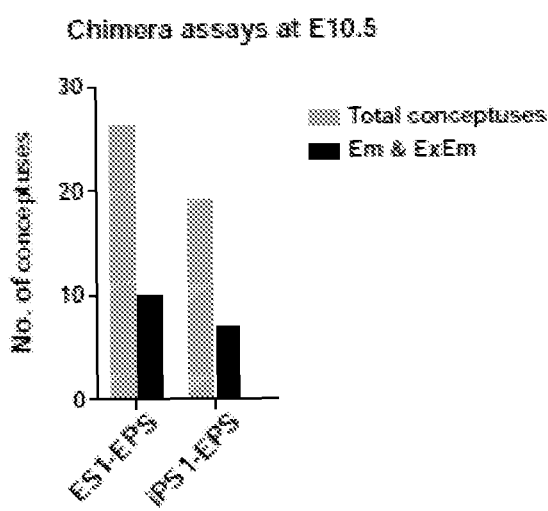
FIG. 1B is a bar graph showing the summary of chimera assays at E10.5. Total conceptuses: total number of recovered E10.5 conceptuses; Em (embryonic) & ExEm (extraembryonic): the number of conceptuses with the integration of human cells into both Em and ExEM tissues.

The chimeric competency of hEPS cells in post-implantation E10.5 mouse conceptuses was also examined. The presence of human cells in mouse conceptuses was identified by immunostaining with the anti-human nuclei (hN) antibody, or by detection of fluorescence signals from fluorescent-labeled hEPS cells. Interspecies chimerism was observed in E10.5 embryos with hEPS cells, but not with primed hPSCs (data not shown) or non-injected controls (Data not shown). Among 44 recovered chimeric E10.5 conceptuses, 17 conceptuses (38.6%) showed the integration of human cells into both embryonic and extraembryonic tissues (FIG. 1B).

hEPS derivatives in chimeric embryos lost expression of the pluripotency marker NANOG (data not shown), and expressed appropriate lineage-specific markers including SOX2, GATA4, and FOXA2 (data not shown). Intriguingly, the integration of hEPS-derived cells into ExEm tissues such as the placenta and yolk sac was also observed (data not shown). This, was unexpected since human and mouse placentas are structurally different, likely as a result of heterochronic and/or divergent placental developmental programs (Rossant, et al., Nat. Rev. Gen., 2:538-548 (2001). These cells were found integrated into the trophoblast layers and expressed the trophoblast marker CK8 (data not shown). Furthermore, the expression of another human trophoblast-specific marker hCGβ was also observed in these cells (data not shown), as is also detected in the teratomas derived from hEPS cells (data not shown). In contrast, the presence of human cells in the mouse placenta injected with primed hPSCs was not observed (data not shown).

Figure 5D:
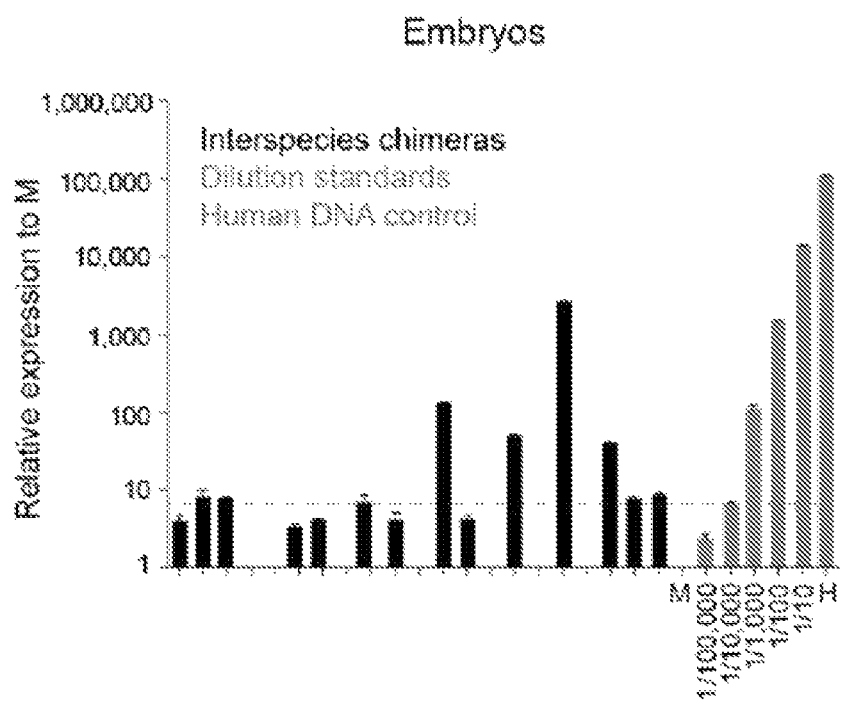
FIG. 5D shows quantitative PCR analysis for human mitochondrial DNA indicated the presence of hEPS-derived cells in E10.5 mouse embryos. A human DNA control (H, red bar) and human-mouse cell dilutions (blue bars) were used to estimate the degree of human cell contribution. The dashed line indicates the detection level of human mitochondrial DNA equivalent to a dilution of 1 human cell in 10,000 mouse cells. M, non-injected mouse embryo.
Figure 5E:
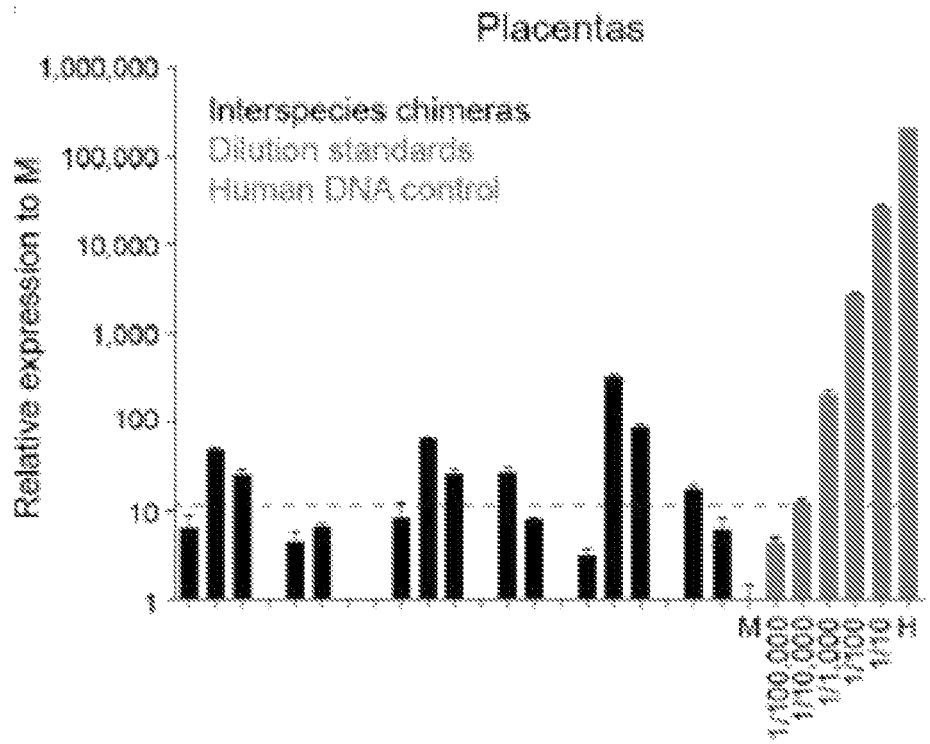
FIG. 5E shows quantitative PCR analysis for human mitochondrial DNA indicated the presence of human cells in mouse placentas at E10.5 following injection of hEPS cells at the 8-cell or blastocyst stages. A human DNA control (H, red bar) and a series of human-mouse cell dilutions (blue bars) were run in parallel to estimate the degree of human cell contribution. The dashed line indicates the detection level of human mitochondrial DNA equivalent to a dilution of 1 human cell in 10,000 mouse cells. M, non-injected mouse placenta.

To further confirm the interspecies chimerism, a highly sensitive mitochondrial PCR assay was employed to quantitatively analyze the degree of contribution of human EPS cells in human-mouse chimeric conceptuses (Theusen, et al., Cell Stem Cell, doi:10.1016/j.stem.2016.06.11). Notably, 35.5% of recovered hEPS-derived mouse embryos (42/118 recovered embryos) contained human cells (1 human cell in 10,000 mouse cells was used as the threshold). The percentage of human cells varied and in some cases reached more than 1% (FIG. 5D and Tables 12a-12c). In addition, 17.6% of recovered hEPS-derived mouse placentas (24/136 recovered placentas) showed human cell contribution (FIG. 5E and Tables 12a-12c), the percentage of which could reach more than 0.1%. Among 54 analyzed mouse conceptuses, 9 (16.6%) showed dual contribution of hEPS derivatives to both mouse embryos and placentas (Tables 12a-12c). As control, primed hPSCs showed no contribution to mouse embryo or placenta (0/54 analyzed mouse conceptuses) (Tables 12a-12c Compared to mEPS cells, the chimeric efficiency of hEPS cells in mouse conceptuses is still limited, which in part can be attributed to species specific differences in development (Malassie, et al., Human Reprod. Update, 9:531-539 (2003). These data show that hEPS cells do exhibit interspecies chimeric competency, and can adopt trophoblast fate in vivo.

Figure 6A:
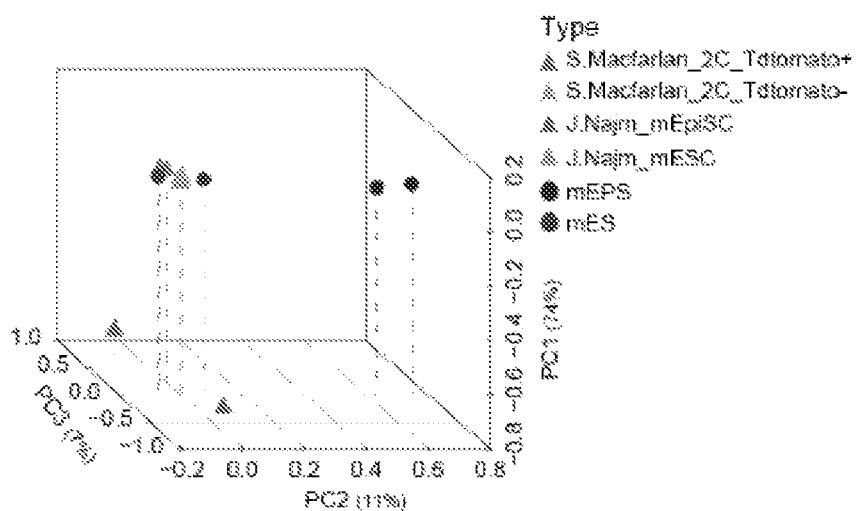
FIGS. 6A and 6B show PCA of RNA-seq and microarray data from EPS cells and known pluripotent cell types. For (6A), data from mEPS cells (this study), mES cells, 2C-like cells (Macfarlan et al. (2012)), and epiblast stem cells (Najm et al. (2011)) were analyzed. Data were normalized to mES cells in each study. A total of 17,243 genes were selected in (a). For (6B), data from hEPS cells (this study), naïve hPSCs (Takashima et al. (2014), Chan et al. (2013), Gafni et al. (2013), and Theunissen et al. (2014)), and primed hPSCs were analyzed. Data were normalized to primed hPSCs in each study. A total of 15,958 genes were selected in (6B). Circles: RNA-seq data; triangles: microarray data.
Figure 6B:
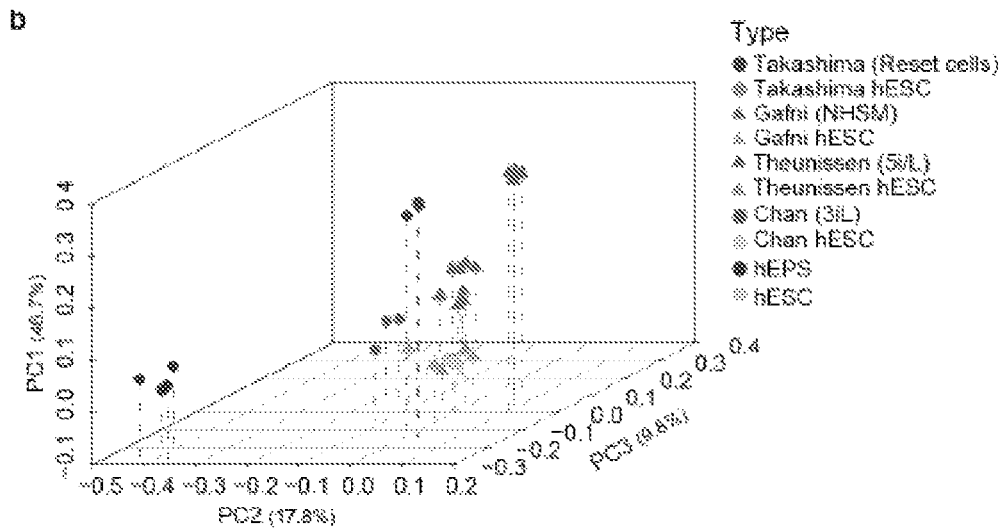

To characterize the molecular features of EPS cells, the transcriptomes of mEPS cells, mES cells, 2C-like mES subpopulations were assessed (Macfarlan, et al., *Nature*, 487:57-63 (2011), and epiblast stem cells (Najm, et al., *Cell Stem Cell*, 8:318-325 (2011). Principal component analysis revealed a global gene expression pattern of mEPS cells that was distinct from other cell types (FIG. 6a). Likewise, hEPS cells also showed distinct transcriptomic features to naïve hPSCs (Takashima, et al., *Cell*, 158:1254-1269 (2014); Chan, et al., *Cell Stem Cell*, 13:663-675 (2013); Theunissen, et al., *Cell Stem Cell*, 15:471-487 (2014); and Gafni, et al., *Nature*, 504:282 (2013)) and primed hPSCs (FIG. 6b). Further experiments examined whether differently expressed genes between mEPS and mES cells, two distinct gene modules (Module A and B) stand out among genes upregulated in mEPS cells (data shown). Compared to mouse embryonic cells from early preimplantation development (Tang, et al., *PLoS One*, 6:e21208 (2011), Module A was uniquely presented in mEPS cells, the function of which was involved in chromatin organization and transcriptional regulation. Notably, genes from Module B were also expressed in embryonic cells at 2-cell stage (data not shown). Interestingly, the expression levels of genes from Module B were gradually downregulated from 2-cell stage to blastocyst stage.

By performing similar analysis, two gene modules (termed Module C and D) were identified among genes upregulated in hEPS cells compared to primed hPSCs (data not shown). Similar to Module A, genes from Module C were involved in chromatin organization and transcriptional regulation, a significant number of which were shared among the naïve hPSCs examined. Notably, a significant number of genes from Module D was also found in human embryonic cells from oocyte to morula stage (Yan, et al., *Nat. Struct. Mol. Biol.*, 20:1131-1139 2013), such as GBX2 (Gastrulation Brain Homeobox 2), HOXA1 (Homeobox A1), MIXL1 (Mix1 homeobox-like 1), and DERA (deoxyribose-phosphate aldolase) (data not shown) genes. Further analysis led to the identification of Module E that was exclusively upregulated in hEPS cells but not other hPSC types, such as CHD7(Chromodomain Helicase DNA Binding Protein 7)), CHD4(Chromodomain Helicase DNA Binding Protein 4), MIXL1 and LEF1 (Lymphoid enhancer-binding factor 1) (data not shown). Interestingly, GO analysis revealed that genes from Module E are involved in biological processes such as transcriptional regulation and cell cycle, which also mark human embryonic cells from oocyte to 4-cell (4C)-stage (*Nat. Struct. Mol. Biol.*, 20:1131-1139 2013)). Collectively, these data suggest that EPS cells possess unique molecular features distinct from known PSC types.

Figure 4E:
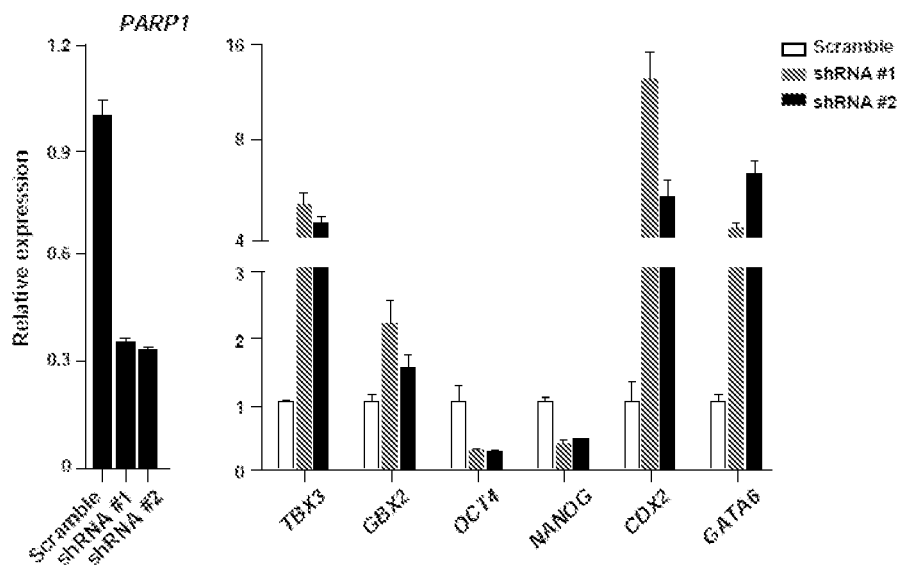
FIG. 4E shows the effect of PARP1 knockdown on the expression of selected genes in hEPS cells on passage 3 after knockdown. hEPS cells were cultured under LCD condition. Expression values are normalized to the mean value of the scramble control. Center values indicate mean. Error bars indicate s.d. (n=3, technical replicates).
Figure 4F:
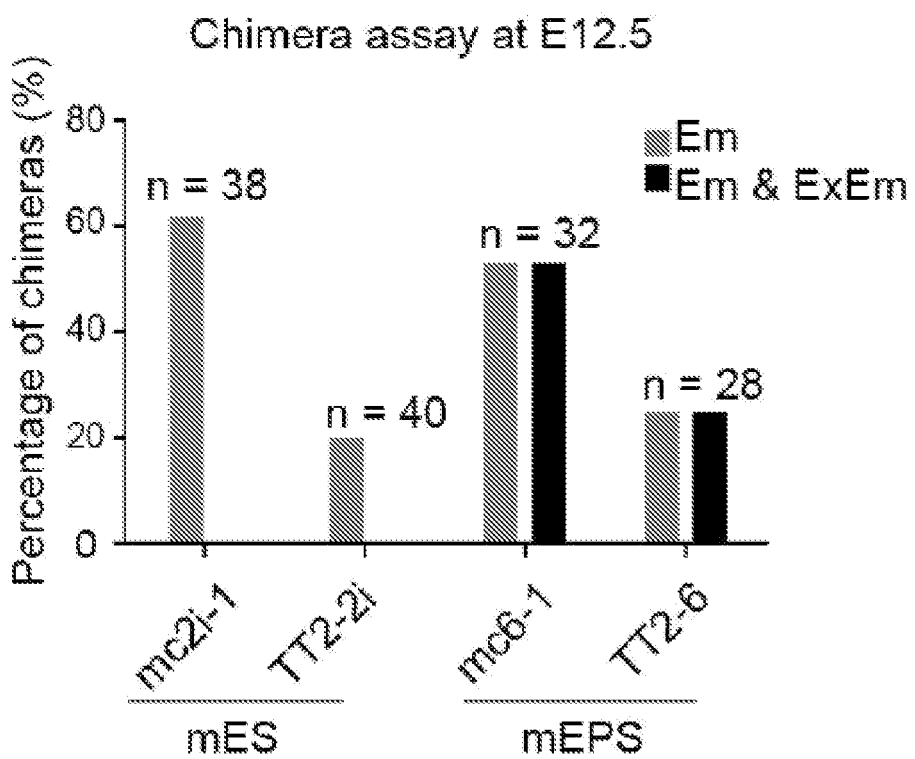
FIG. 4F is a bar graph showing a summary of chimera assays at E12.5. The bar chart shows the percentages of chimeras (gray, integration into embryonic tissues (Em); black, integration into both embryonic and extraembryonic placental tissues (Em&ExEm)) among the recovered E12.5 conceptuses.
Figure 4G:
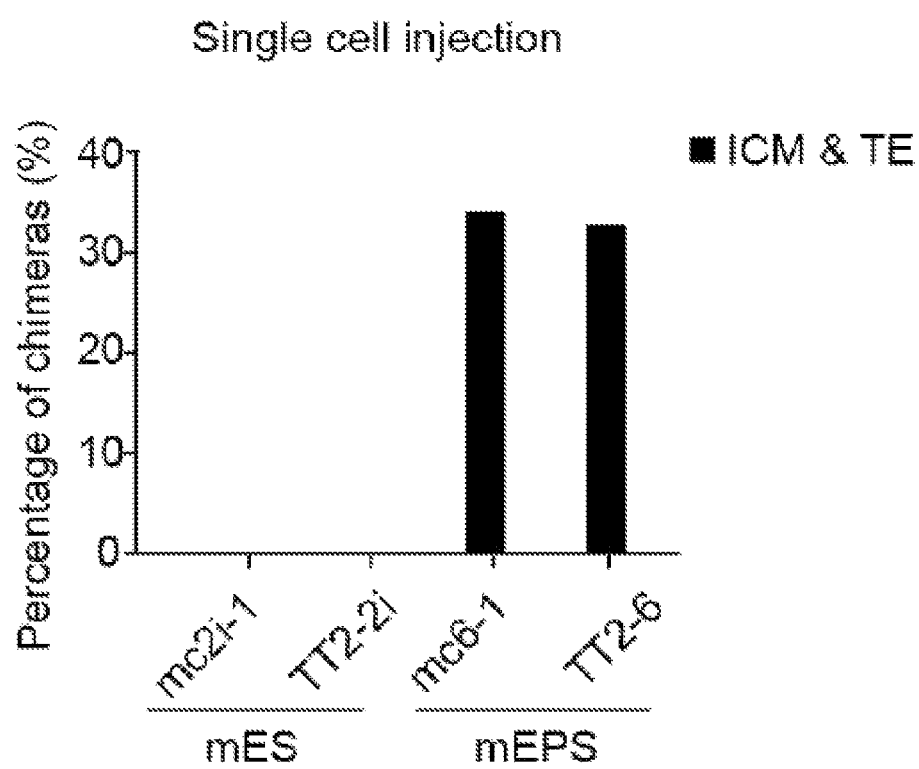
FIG. 4G is a bar graph showing a summary of chimeric assays of single-cell injection at the 8-cell embryo stage. The bar chart shows the percentage of chimeras among the recovered blastocysts. ICM & TE, embryos with the integration of mouse cells into both ICM and TE.
Figure 6C:
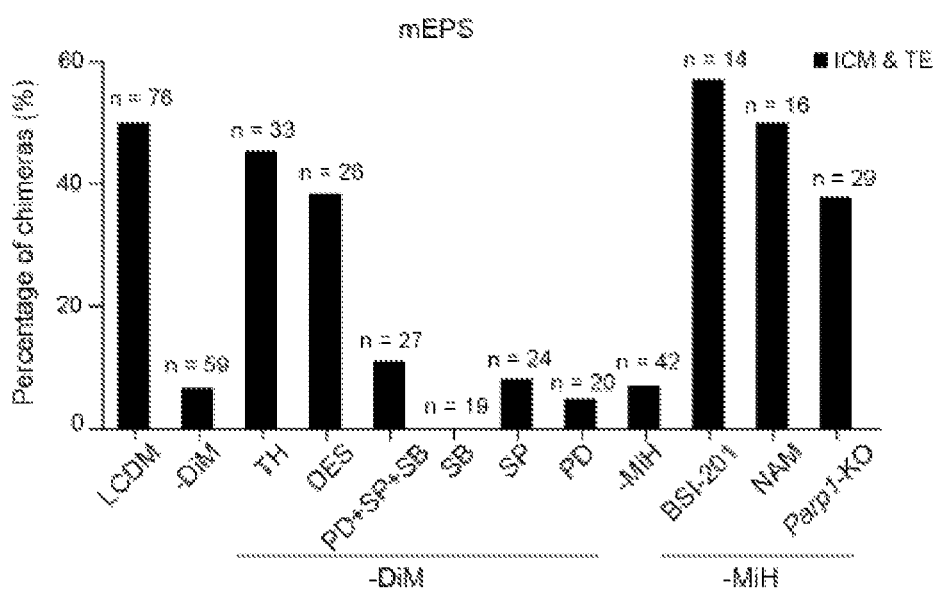
FIG. 6C shows an analysis of the influence of DiM or MiH substitution on the chimeric ability of mEPS cells. Parp1 knockout mEPS cells (Parp1-KO) were cultured in LCDM condition without MiH (-MiH). mEPS cells were cultured under different conditions for at least 5 passages before injection. Multiple cells were injected into 8-cell embryos, which were cultured for additional 60 hours before further analysis. The bar chart shows the percentage of chimeras among the recovered blastocysts. ICM & TE, embryos with the integration of mouse cells into both ICM and TE.
Figure 6D:
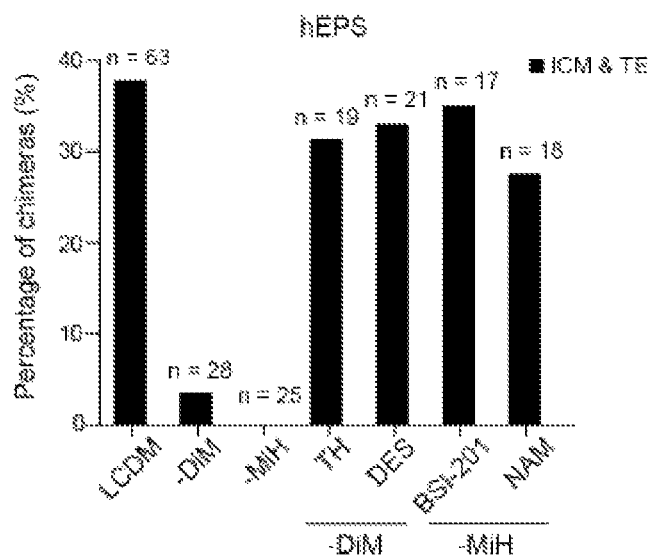
FIG. 6D shows an analysis of the influence of DiM or MiH substitution on the chimeric ability of hEPS. hEPS cells were cultured under different conditions for at least 5 passages, and then multiple cells were injected into 8-cell embryos, which were cultured for additional 60 hours before further analysis. The bar chart shows the percentage of chimeras among the recovered blastocysts. ICM & TE, embryos with the integration of mouse cells into both ICM and TE. TH: TripelennamineHCL; DES: Desloratadine; NAM: Nicotinamide. PD: PD0325901; SB: SB203580; SP: SP600125.

Finally, the roles of DiM and MiH in maintaining EPS cells were investigated. The withdrawal of either DiM or MiH led to rapid differentiation of hEPS cells within days after plating (data not shown), suggesting that both small molecules are required for the maintenance of hEPS cells. The withdrawal of either DiM or MiH also significantly impaired the developmental potency of mEPS cells in chimeric blastocysts (FIG. 6C, data not shown) DiM has been reported to inhibit G protein coupled receptors including the histamine and the muscarinic receptors (Pfaff, et al., *Eur. J., Phamacol.*, 286-229-240 (1995)), while MiH is known to inhibit PARP1 (Alano, et al., *Proc. Natl., Acad. Sci. USA*, 103:9685-9690 (2006)). Notably, DiM or MiH could be replaced with other inhibitors targeting the same targets for the maintenance of hEPS cells (TripelennamineHCL; Desloratadine; or Nicotinamide; BSI-201 (4-iodo-3-nitrobenzamide)) (data not shown). Indeed, replacement of DiM with inhibitors targeting to both histamine receptor and muscarinic receptor not only supported the morphology and expansion of hEPS cells (data not shown), but also maintained the expression of genes that were upregulated in hEPS cells, such as GBX2, TBX3, CDX2, and GATA6 (FIG. 4C). Replacement of MiH with other PARP1 inhibitors also maintained hEPS expansion and marker genes upregulated in hEPS cells (data not shown, and FIG. 4D). Furthermore, similar results were obtained when MiH was replaced by the knockdown of PARP1 in hEPS cells (FIG. 4E). Importantly, both mEPS and hEPS cells still retained their ability of contributing to both TE and ICM in blastocysts under such conditions (FIG. 6C, 6D, and data not shown).

Figure 7A:
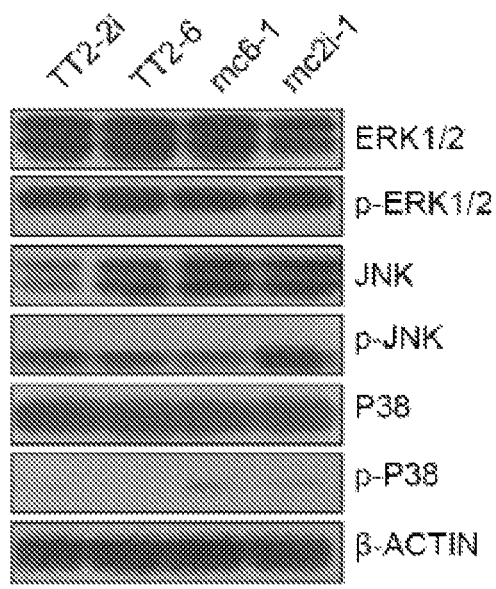
FIGS. 7A and 7B show western blot analysis for the total and phosphorylated levels of the proteins involved in MAPK signaling in the mES (TT2-2i, mc2i-1) and mEPS cells (TT2-6, mc6-1) (FIG. 7A), and hEPS cells and primed hPSCs (FIG. 7B). Similar results were obtained in three independent experiments.
Figure 7B:
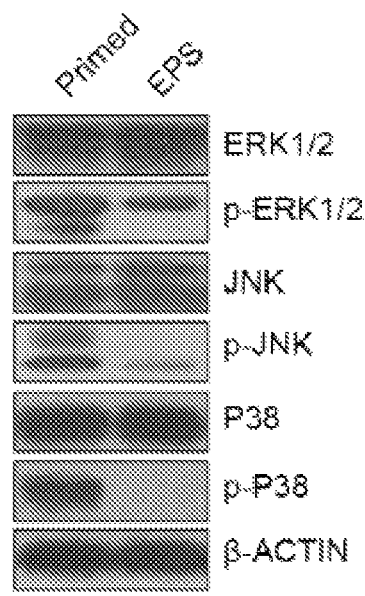
Figure 7C:
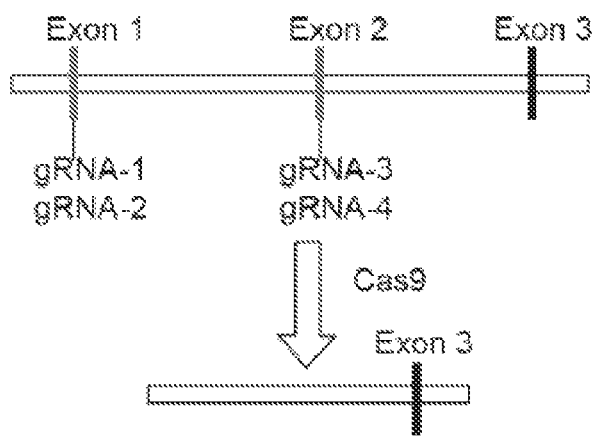
FIG. 7C is a schematic showing the generation of Parp1 knockout mEPS cell lines. gRNAs are targeted to the sequences within exon 1 and 2 in Parp1 locus respectively, which were co-transfected into mEPS cells. After the expression of Cas9 protein, genomic fragments from exon 1 to exon 2 were deleted from the Parp1 locus.
Figure 7D:
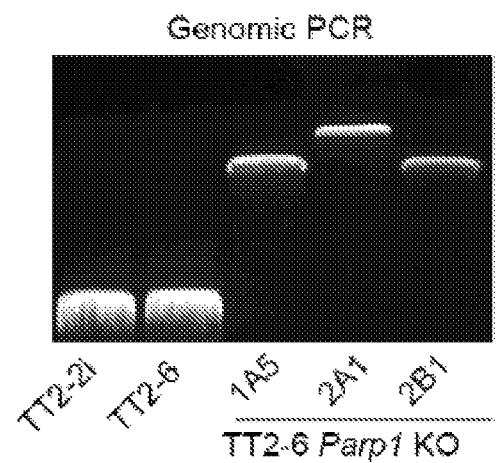
FIG. 7D shows genomic PCR analysis confirmed that the Parp1 locus in three sub clones (2B1, 2A1 and 1A5) of mEPS cell line TT2-6 was successfully targeted. Wild-type mES TT2-2i and mEPS TT2-6 were used as controls.
Figure 7E:
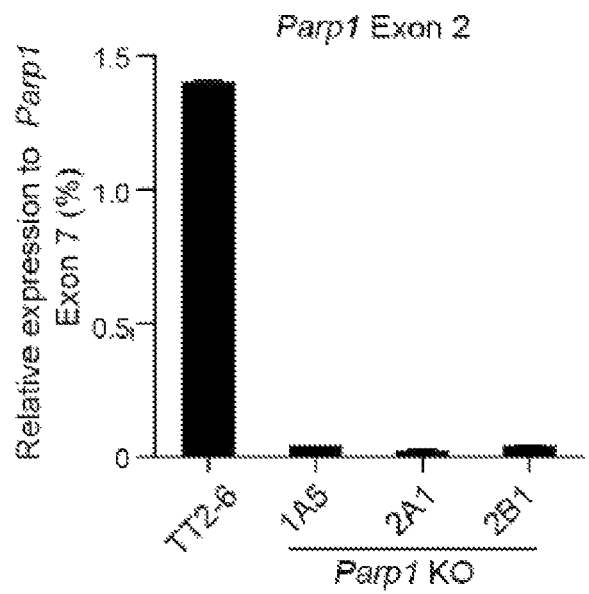
FIGS. 7E and 7F show genomic Q-PCR and QRT-PCR analysis confirmed the absence of Parp1 exon (7E) and mRNA expression (7F) in Parp1 knockout mEPS sub clones (Parp1 KO). Wild-type mEPS cell line TT2-6 was used as the control.
Figure 7F:
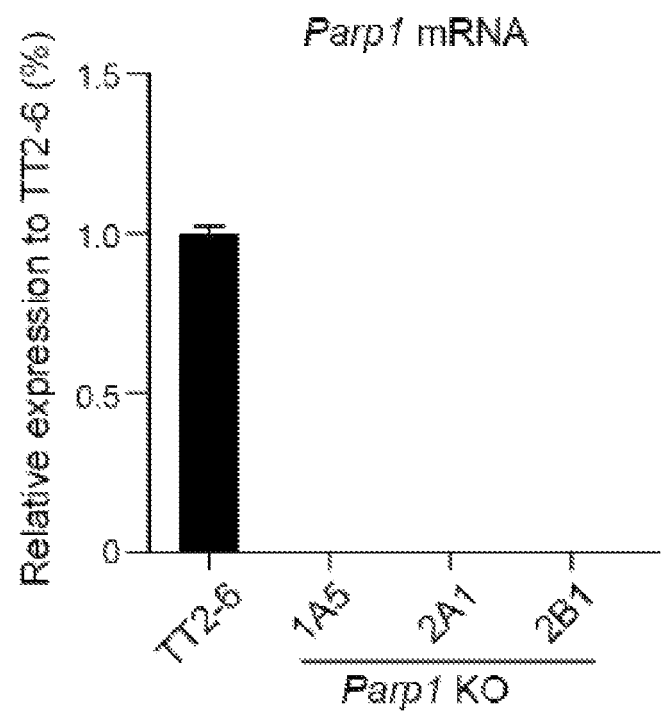
Figure 7G:
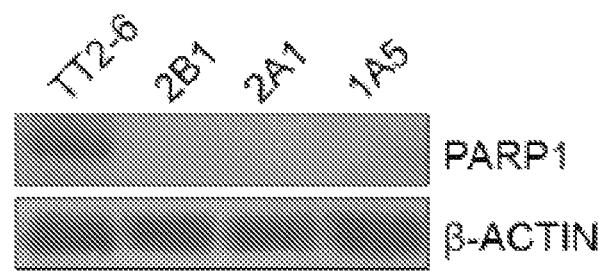
FIG. 7G show a western blot analysis confirming the absence of PARP1 protein expression in Parp1 knockout mEPS clones (2B1, 2A1 and 1A5). Wild-type mEPS cell line TT2-6 was used as the control.

The molecular targets regulated by DiM and MiH in EPS cells were investigated next. MAPK signaling has been reported to be the major downstream of histamine and muscarinic receptor signaling (Morse, et al., *J. Pharmacol. Exp. Ther.* 296:1058-1066 (2001) and Ockenga, et al., *Genes (basel)*, 4:171-79 (2013)), and the downregulation of MAPK signaling activities was observed in both mEPS and hEPS cells (FIG. 7A-B). However, replacement of DiM with inhibitors targeting MAPK signaling (PD0325901; SB203580; SP600125) could not maintain hEPS cells (data not shown), and could not preserve the developmental potency of mEPS cells (FIG. 6C, and data not shown). To further examine the role of MiH, Parp1, a proposed molecular target of MiH was knocked out in mEPS cell lines (FIG. 7C-G). Importantly, Parp1 deficient mEPS cells could still differentiate into both TE and ICM even in the absence of MiH (FIG. 6C). A summary of the chimeric analysis of cells cultured under different conditions in shown in Table 14.

TABLE 14

Summary of chimeric analysis of EPS cells cultured under different conditions

| Conditions | Cell lines | Injected embryos | Recovered embryos | Contribute into both |
|---|---|---|---|---|
| LCDM | TT2- | 22 | 22 | 10 |
|  | TT2- | 15 | 15 | 7 |
|  | TT2- | 10 | 10 | 4 |
|  | mc6- | 2 | 2 | 2 |
|  | mc6- | 20 | 18 | 12 |
|  | mc6- | 10 | 9 | 3 |
|  | Sum | 79 | 76 | 38 |
| LCM* | TT2- | 20 | 18 | 0 |
|  | TT2- | 10 | 7 | 1 |
|  | mc6- | 20 | 5 | 1 |
|  | mc6- | 16 | 16 | 2 |
|  | mc6- | 5 | 5 | 0 |
|  | mc6- | 10 | 8 | 0 |
|  | Sum | 81 | 59 | 4 |
| LCM + DE‡ | TT2- | 14 | 13 | 2 |
|  | TT2- | 10 | 10 | 7 |
|  | mc6- | 10 | 10 | 6 |
|  | Sum | 34 | 33 | 15 |
| LCM + TH§ | TT2- | 15 | 8 | 1 |
|  | TT2- | 10 | 8 | 4 |
|  | mc6- | 10 | 10 | 5 |
|  | Sum | 35 | 26 | 10 |
| LCM + PD‖ + SB¶ + SP** | TT2- | 10 | 9 | 1 |
|  | mc6- | 18 | 18 | 2 |
|  | Sum | 28 | 27 | 3 |
| LCM + SB | TT2- | 10 | 9 | 0 |
|  | mc6- | 10 | 10 | 0 |
|  | Sum | 20 | 19 | 0 |
| LCM + SP | TT2- | 12 | 12 | 2 |
|  | mc6- | 12 | 12 | 0 |
|  | Sum | 24 | 24 | 2 |
| LCM + PD | TT2- | 10 | 10 | 0 |
|  | mc6- | 10 | 10 | 1 |
|  | Sum | 20 | 20 | 1 |
| LCD‡‡ | TT2- | 20 | 20 | 1 |
|  | mc6- | 20 | 17 | 2 |
|  | mc6- | 5 | 5 | 0 |
|  | Sum | 45 | 42 | 3 |
| LCD + BSI-201 | TT2- | 10 | 4 | 3 |
|  | mc6- | 10 | 10 | 5 |
|  | Sum | 20 | 14 | 8 |
| LCD + NAM§§ | TT2- | 10 | 6 | 4 |
|  | mc6- | 10 | 10 | 4 |
|  | Sum | 20 | 16 | 8 |
| LCD Parp1 Knockout | TT2- | 10 | 9 | 6 |
|  | TT2- | 10 | 10 | 2 |
|  | TT2- | 10 | 10 | 3 |
|  | Sum | 30 | 29 | 11 |

These results suggest that Parp1 is an important regulator in the maintenance of EPS developmental potency.

These studies provide proof-of-principle evidence that the developmental potency of pluripotent stem cells can be extended to both embryonic and extraembryonic lineages. Unlike reported unstable pluripotent populations with extra-embryonic potentials in mouse (Macfarlan, et al., *Nature*, 487:57-63 (2012); Morgani, et al., *Cell Rep.*, 3:1945-4957 (2012); and Abad, et al., *Nature*, 502:340-345 (2013), EPS cells can be maintained in the long term in vitro while maintaining their embryonic and extraembryonic developmental potency. EPS cells also represent a novel stem cell resource which has several potential advantages over traditional pluripotent stem cells. Although the first mouse ES cell lines were established 34 years ago (Evans, et al., *Nature*, 292:154-156 (1981); and Martin, et al., *Proc Natl Acad Sci USA*, 78:7634-7638 (1981)), the derivation of pluripotent stem cells with chimeric abilities from other mammals is still a major challenge. There still lacks a robust method for establishing pluripotent stem cells in different mammalian species. EPS cells can be generated in different mammalian species using the same culture conditions, suggesting the conservation of this novel cell state among mammals. Therefore, the discovery of EPS cell provides an opportunity of developing one universal method to robustly establish stem cells with extended developmental potency in mammals. Furthermore, the interspecies chimera competency of EPS cells makes them particularly valuable for studying xenogeneic chimerism and mammalian early development. Finally, EPS cells also provide novel cell resources for disease modelling, drug discovery, and generating functional cells for regenerative medicine.

We claim:

1. A cell culture medium for extending cell potency of an isolated pluripotent stem cells, the cell culture medium comprising
   (i) 1-100 ng/ml of human leukemia inhibitory factor (LIF),
   (ii) 0.5-5.0 µM of 6-[[2-[[4-(2,4-Dichlorophenyl)-5-(5-methyl-1H-imidazol-2-yl)-2-pyrimidin-yl]amino]ethyl]amino]-3-pyridinecarbonitrile,
   (iii) 1.0-5.0 µM of (S)-(+)-Dimethindene maleate (DiM), and
   (iv) 0.5-5.0 µM of Minocycline hydrochloride (MiH), wherein said culture medium maintains the normal karyotype and extend the pluripotent state of the pluripotent stem cells for at least 5 passages.

2. The cell culture medium of claim 1, further comprising 0.2 to 20 µM of a Rho-associated, coiled-coil containing protein kinase (ROCK) inhibitor selected from the group consisting of [(+)-(R)-trans-4-(1-aminoethyl)-N-(4-pyridyl)cyclohexanecarboxamide+++dihydrochloride)] (Y27632) and fusadil.

3. The cell culture medium of claim 1, further comprising 4-[(3aR,4S,7R,7aS)-1,3,3a,4,7,7a-hexahydro-1,3-dioxo-4,7-methano-2H-isoindol-2-yl]-N-8-quinolinyl-benzamide) (endo-IWR1) or 3,5,7,8-Tetrahydro-2-[4-(trifluoromethyl)phenyl]-4H-thiopyrano [4,3-d]pyrimidin-4-one (XAV939).

4. A method for culturing pluripotent stem cells, the method comprising:

(a) seeding pluripotent stem cells as single cell in an ES cell culture medium containing 1.0 to 10 µM of [(+)-(R)-trans-4-(1-aminoethyl)-N-(4-pyridyl)cyclohexanecarboxamide+++dihydrochloride)] for 12 to 24 hours; and (b) culturing the pluripotent stem cells from step (a) in a cell culture medium comprising (i) 1-100 ng/ml of human leukemia inhibitory factor (LIF), (ii) 0.5-5.0 µM of 6-[[2-[[4-(2,4-Dichlorophenyl)-5-(5-methyl-1H-imidazol-2-yl)-2-pyrimidin-yl]amino]ethyl]amino]-3-pyridinecarbonitrile, (iii) 1.0-5.0 µM of (S)-(+)-Dimethindene maleate (DiM), and (iv) 0.5-5.0 µM of Minocycline hydrochloride (MiH) to maintain pluripotency in said pluripotent stem cells, wherein said pluripotent stem cells maintain normal karyotype in the culture for at least 5 passages.

5. A method for culturing pluripotent stem cells, the method comprising:

culturing pluripotent stem cells in a cell culture medium comprising (i) 1-100 ng/ml of human leukemia inhibitory factor (LIF), (ii) 0.5-5.0 µM of 6-[[2-[[4-(2,4-Dichlorophenyl)-5-(5-methyl-1H-imidazol-2-yl)-2-pyrimidin-yl]amino]ethyl]amino]-3-pyridinecarbonitrile, (iii) 1.0-5.0 µM of (S)-(+)-Dimethindene maleate (DiM), and (iv) 0.5-5.0 µM of Minocycline hydrochloride (MiH) to maintain pluripotency in said pluripotent stem cells, wherein said pluripotent stem cells maintain normal karyotype in the culture for at least 5 passages.

* * * * *

SEQUENCE LISTING

<160> NUMBER OF SEQ ID NOS: 83

<210> SEQ ID NO 1
<211> LENGTH: 21
<212> TYPE: DNA
<213> ORGANISM: artificial sequence
<220> FEATURE:
<223> OTHER INFORMATION: qRT-PCR primers of human

<400> SEQUENCE: 1
cggagtcttc ggataagctc t          21

<210> SEQ ID NO 2
<211> LENGTH: 21
<212> TYPE: DNA

```
<213> ORGANISM: artificial sequence
<220> FEATURE:
<223> OTHER INFORMATION: qRT-PCR primers of human

<400> SEQUENCE: 2
tttccatcaa acatgggcga c                                            21

<210> SEQ ID NO 3
<211> LENGTH: 21
<212> TYPE: DNA
<213> ORGANISM: artificial sequence
<220> FEATURE:
<223> OTHER INFORMATION: qRT-PCR primers of human

<400> SEQUENCE: 3
cccggttcca cattgtaaga g                                            21

<210> SEQ ID NO 4
<211> LENGTH: 22
<212> TYPE: DNA
<213> ORGANISM: artificial sequence
<220> FEATURE:
<223> OTHER INFORMATION: qRT-PCR primers of human

<400> SEQUENCE: 4
gtatgcagtc acagcgatga at                                           22

<210> SEQ ID NO 5
<211> LENGTH: 21
<212> TYPE: DNA
<213> ORGANISM: artificial sequence
<220> FEATURE:
<223> OTHER INFORMATION: qRT-PCR primers of human

<400> SEQUENCE: 5
gacgagtcaa aggtggaaga c                                            21

<210> SEQ ID NO 6
<211> LENGTH: 22
<212> TYPE: DNA
<213> ORGANISM: artificial sequence
<220> FEATURE:
<223> OTHER INFORMATION: qRT-PCR primers of human

<400> SEQUENCE: 6
gattgtcatc cgagctgtag tc                                           22

<210> SEQ ID NO 7
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 7
cagtcgctac atcaccatcc                                              20

<210> SEQ ID NO 8
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 8
tttcctctcc tttgctctgc                                              20
```

<210> SEQ ID NO 9
<211> LENGTH: 21
<212> TYPE: DNA
<213> ORGANISM: artificial sequence
<220> FEATURE:
<223> OTHER INFORMATION: qRT-PCR primers of human

<400> SEQUENCE: 9
ctcagttcct acgcttcgca t                                           21

<210> SEQ ID NO 10
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 10
gtcgaggtca gtgaacagca                                             20

<210> SEQ ID NO 11
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 11
cgccaccaaa ctgagatgat                                             20

<210> SEQ ID NO 12
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 12
cacattgtag tgggcagtgg                                             20

<210> SEQ ID NO 13
<211> LENGTH: 19
<212> TYPE: DNA
<213> ORGANISM: artificial sequence
<220> FEATURE:
<223> OTHER INFORMATION: qRT-PCR primers of human

<400> SEQUENCE: 13
aactcaagaa ggcggatgg                                              19

<210> SEQ ID NO 14
<211> LENGTH: 19
<212> TYPE: DNA
<213> ORGANISM: artificial sequence
<220> FEATURE:
<223> OTHER INFORMATION: qRT-PCR primers of human

<400> SEQUENCE: 14
cggtgcgtcc tttaatcct                                              19

<210> SEQ ID NO 15
<211> LENGTH: 20
<212> TYPE: DNA
<213> ORGANISM: artificial sequence
<220> FEATURE:

<223> OTHER INFORMATION: qRT-PCR primers of human

<400> SEQUENCE: 15
gctcgagaag gatgtggtcc                                                    20

<210> SEQ ID NO 16
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 16
cgttgtgcat agtcgctgct                                                    20

<210> SEQ ID NO 17
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 17
gcagaaggcc tcagcaccta                                                    20

<210> SEQ ID NO 18
<211> LENGTH: 19
<212> TYPE: DNA
<213> ORGANISM: artificial sequence
<220> FEATURE:
<223> OTHER INFORMATION: qRT-PCR primers of human

<400> SEQUENCE: 18
aggttcccag tcgggttca                                                     19

<210> SEQ ID NO 19
<211> LENGTH: 19
<212> TYPE: DNA
<213> ORGANISM: artificial sequence
<220> FEATURE:
<223> OTHER INFORMATION: qRT-PCR primers of human

<400> SEQUENCE: 19
gtggaccgca cggaatttg                                                     19

<210> SEQ ID NO 20
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 20
ggagattcac accggagtca                                                    20

<210> SEQ ID NO 21
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 21
cgagatccct ccaaaatcaa                                                    20

```
<210> SEQ ID NO 22
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 22
atccacagtc ttctgggtgg                                              20

<210> SEQ ID NO 23
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 23
cttctgcttc aggagcttgg                                              20

<210> SEQ ID NO 24
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 24
gaaggagaag ctggagcaaa                                              20

<210> SEQ ID NO 25
<211> LENGTH: 17
<212> TYPE: DNA
<213> ORGANISM: artificial sequence
<220> FEATURE:
<223> OTHER INFORMATION: qRT-PCR primers of human

<400> SEQUENCE: 25
gtgcaccgag ctggagg                                                 17

<210> SEQ ID NO 26
<211> LENGTH: 17
<212> TYPE: DNA
<213> ORGANISM: artificial sequence
<220> FEATURE:
<223> OTHER INFORMATION: qRT-PCR primers of human

<400> SEQUENCE: 26
gcacgtcctg gcctctc                                                 17

<210> SEQ ID NO 27
<211> LENGTH: 21
<212> TYPE: DNA
<213> ORGANISM: artificial sequence
<220> FEATURE:
<223> OTHER INFORMATION: qRT-PCR primers of human

<400> SEQUENCE: 27
gacgagtcaa aggtggaaga c                                            21

<210> SEQ ID NO 28
<211> LENGTH: 22
<212> TYPE: DNA
<213> ORGANISM: artificial sequence
<220> FEATURE:
<223> OTHER INFORMATION: qRT-PCR primers of human
```

<400> SEQUENCE: 28
gattgtcatc cgagctgtag tc                                          22

<210> SEQ ID NO 29
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 29
gaaactcctt ctccagctcc                                             20

<210> SEQ ID NO 30
<211> LENGTH: 19
<212> TYPE: DNA
<213> ORGANISM: artificial sequence
<220> FEATURE:
<223> OTHER INFORMATION: qRT-PCR primers of human

<400> SEQUENCE: 30
gaacctgtgc gagtggatg                                              19

<210> SEQ ID NO 31
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 31
ctgcttcatg gatccctacc                                             20

<210> SEQ ID NO 32
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 32
gatggacgtc ttggagaagg                                             20

<210> SEQ ID NO 33
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 33
cacattgtag tgggcagtgg                                             20

<210> SEQ ID NO 34
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 34
cgccaccaaa ctgagatgat                                             20

<210> SEQ ID NO 35
<211> LENGTH: 21

```
<212> TYPE: DNA
<213> ORGANISM: artificial sequence
<220> FEATURE:
<223> OTHER INFORMATION: qRT-PCR primers of human

<400> SEQUENCE: 35
tagcgaatct gtttcccctc t                                              21

<210> SEQ ID NO 36
<211> LENGTH: 22
<212> TYPE: DNA
<213> ORGANISM: artificial sequence
<220> FEATURE:
<223> OTHER INFORMATION: qRT-PCR primers of human

<400> SEQUENCE: 36
ctgctgtaaa gccactcatc tt                                             22

<210> SEQ ID NO 37
<211> LENGTH: 22
<212> TYPE: DNA
<213> ORGANISM: artificial sequence
<220> FEATURE:
<223> OTHER INFORMATION: qRT-PCR primers of human

<400> SEQUENCE: 37
gccttatgtg atggctatgt gt                                             22

<210> SEQ ID NO 38
<211> LENGTH: 23
<212> TYPE: DNA
<213> ORGANISM: artificial sequence
<220> FEATURE:
<223> OTHER INFORMATION: qRT-PCR primers of human

<400> SEQUENCE: 38 acccctttatg acgcattcta tgt                                           23

<210> SEQ ID NO 39
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 39
gctccactcg ttggaggtaa                                                20

<210> SEQ ID NO 40
<211> LENGTH: 17
<212> TYPE: DNA
<213> ORGANISM: artificial sequence
<220> FEATURE:
<223> OTHER INFORMATION: qRT-PCR primers of human

<400> SEQUENCE: 40
cttagcgcac ccatccc                                                   17

<210> SEQ ID NO 41
<211> LENGTH: 20
<212> TYPE: DNA
<213> ORGANISM: artificial sequence
<220> FEATURE:
<223> OTHER INFORMATION: qRT-PCR primers of human

<400> SEQUENCE: 41
```
gacagcagtc ggttggagcg                                                    20

<210> SEQ ID NO 42
<211> LENGTH: 23
<212> TYPE: DNA
<213> ORGANISM: artificial sequence
<220> FEATURE:
<223> OTHER INFORMATION: qRT-PCR primers of human

<400> SEQUENCE: 42
gggacttcct gtaacaacgc atc                                                23

<210> SEQ ID NO 43
<211> LENGTH: 57
<212> TYPE: DNA
<213> ORGANISM: artificial sequence
<220> FEATURE:
<223> OTHER INFORMATION: PARP1 shRNA #1

<400> SEQUENCE: 43
ccggccgaga atctcttac ctcaactcga gttgaggtaa gagatttctc ggttttt           57

<210> SEQ ID NO 44
<211> LENGTH: 57
<212> TYPE: DNA
<213> ORGANISM: artificial sequence
<220> FEATURE:
<223> OTHER INFORMATION: PARP1 shRNA #2

<400> SEQUENCE: 44
ccgggcttca catatcagca ggttactcga gtaacctgct gatatgtgaa gctttt           57

<210> SEQ ID NO 45
<211> LENGTH: 57
<212> TYPE: DNA
<213> ORGANISM: artificial sequence
<220> FEATURE:
<223> OTHER INFORMATION: Scramble

<400> SEQUENCE: 45
ccggcaacaa gatgaagagc accaactcga gttggtgctc ttcatcttgt tgttttt          57

<210> SEQ ID NO 46
<211> LENGTH: 20
<212> TYPE: DNA
<213> ORGANISM: artificial sequence
<220> FEATURE:
<223> OTHER INFORMATION: primers

<400> SEQUENCE: 46
cggcaaagcg gacaataaca                                                    20

<210> SEQ ID NO 47
<211> LENGTH: 21
<212> TYPE: DNA
<213> ORGANISM: artificial sequence
<220> FEATURE:
<223> OTHER INFORMATION: primers

<400> SEQUENCE: 47
ggagccagtg ttaggagatt c                                                  21

<210> SEQ ID NO 48
<211> LENGTH: 20
<212> TYPE: DNA
<213> ORGANISM: artificial sequence

```
<220> FEATURE:
<223> OTHER INFORMATION: primers

<400> SEQUENCE: 48
ctacagtccg ctggtgctgg                                                    20

<210> SEQ ID NO 49
<211> LENGTH: 21
<212> TYPE: DNA
<213> ORGANISM: artificial sequence
<220> FEATURE:
<223> OTHER INFORMATION: primers

<400> SEQUENCE: 49
ggtcacagaa ggatgcgttg g                                                  21

<210> SEQ ID NO 50
<211> LENGTH: 19
<212> TYPE: DNA
<213> ORGANISM: artificial sequence
<220> FEATURE:
<223> OTHER INFORMATION: primers

<400> SEQUENCE: 50
ggcagcctga tgttgaggt                                                     19

<210> SEQ ID NO 51
<211> LENGTH: 22
<212> TYPE: DNA
<213> ORGANISM: artificial sequence
<220> FEATURE:
<223> OTHER INFORMATION: primers

<400> SEQUENCE: 51
gcgtactccg ctaaaaagtc ac                                                 22

<210> SEQ ID NO 52
<211> LENGTH: 19
<212> TYPE: DNA
<213> ORGANISM: artificial sequence
<220> FEATURE:
<223> OTHER INFORMATION: primers

<400> SEQUENCE: 52
ccgtgaaggt gcaaacgtc                                                     19

<210> SEQ ID NO 53
<211> LENGTH: 20
<212> TYPE: DNA
<213> ORGANISM: artificial sequence
<220> FEATURE:
<223> OTHER INFORMATION: primers

<400> SEQUENCE: 53
ccctgctacg agttctggtg                                                    20

<210> SEQ ID NO 54
<211> LENGTH: 23
<212> TYPE: DNA
<213> ORGANISM: artificial sequence
<220> FEATURE:
<223> OTHER INFORMATION: primers

<400> SEQUENCE: 54
ctaccagtta catcgcctac ttg                                                23
```

```
<210> SEQ ID NO 55
<211> LENGTH: 21
<212> TYPE: DNA
<213> ORGANISM: artificial sequence
<220> FEATURE:
<223> OTHER INFORMATION: primers

<400> SEQUENCE: 55
accaccatcc gtcttttga g                                            21

<210> SEQ ID NO 56
<211> LENGTH: 23
<212> TYPE: DNA
<213> ORGANISM: artificial sequence
<220> FEATURE:
<223> OTHER INFORMATION: primers

<400> SEQUENCE: 56
tcctggatac tgctcctact act                                          23

<210> SEQ ID NO 57
<211> LENGTH: 21
<212> TYPE: DNA
<213> ORGANISM: artificial sequence
<220> FEATURE:
<223> OTHER INFORMATION: primers

<400> SEQUENCE: 57
gaccattcct cattgcacac a                                            21

<210> SEQ ID NO 58
<211> LENGTH: 22
<212> TYPE: DNA
<213> ORGANISM: artificial sequence
<220> FEATURE:
<223> OTHER INFORMATION: primers

<400> SEQUENCE: 58
cacagtagcg aaaatgacca gg                                           22

<210> SEQ ID NO 59
<211> LENGTH: 22
<212> TYPE: DNA
<213> ORGANISM: artificial sequence
<220> FEATURE:
<223> OTHER INFORMATION: primers

<400> SEQUENCE: 59
tcctcctctt caaacattgg gt                                           22

<210> SEQ ID NO 60
<211> LENGTH: 22
<212> TYPE: DNA
<213> ORGANISM: artificial sequence
<220> FEATURE:
<223> OTHER INFORMATION: primers

<400> SEQUENCE: 60
cattgccagt tgacaacaca ag                                           22

<210> SEQ ID NO 61
<211> LENGTH: 22
<212> TYPE: DNA
<213> ORGANISM: artificial sequence
<220> FEATURE:
<223> OTHER INFORMATION: primers
```

```
<400> SEQUENCE: 61
atagccttca tttcgccaat ca                                        22

<210> SEQ ID NO 62
<211> LENGTH: 21
<212> TYPE: DNA
<213> ORGANISM: artificial sequence
<220> FEATURE:
<223> OTHER INFORMATION: primers

<400> SEQUENCE: 62
ccaacgtgtg attgtggtgt c                                         21

<210> SEQ ID NO 63
<211> LENGTH: 20
<212> TYPE: DNA
<213> ORGANISM: artificial sequence
<220> FEATURE:
<223> OTHER INFORMATION: primers

<400> SEQUENCE: 63
caggccatag gtccaagctg                                           20

<210> SEQ ID NO 64
<211> LENGTH: 21
<212> TYPE: DNA
<213> ORGANISM: artificial sequence
<220> FEATURE:
<223> OTHER INFORMATION: primers

<400> SEQUENCE: 64
ggcaccacac cttctacaat g                                         21

<210> SEQ ID NO 65
<211> LENGTH: 20
<212> TYPE: DNA
<213> ORGANISM: artificial sequence
<220> FEATURE:
<223> OTHER INFORMATION: primers

<400> SEQUENCE: 65
gtggtggtga agctgtagcc                                           20

<210> SEQ ID NO 66
<211> LENGTH: 23
<212> TYPE: DNA
<213> ORGANISM: artificial sequence
<220> FEATURE:
<223> OTHER INFORMATION: primers

<400> SEQUENCE: 66
gtaccacttc tcctgcttct gga                                       23

<210> SEQ ID NO 67
<211> LENGTH: 21
<212> TYPE: DNA
<213> ORGANISM: artificial sequence
<220> FEATURE:
<223> OTHER INFORMATION: primers

<400> SEQUENCE: 67
ggccgtcttc ttgaccttct g                                         21

<210> SEQ ID NO 68
```

<211> LENGTH: 25
<212> TYPE: DNA
<213> ORGANISM: artificial sequence
<220> FEATURE:
<223> OTHER INFORMATION: primers

<400> SEQUENCE: 68
aagagcgacg cttattactg tactg                                  25

<210> SEQ ID NO 69
<211> LENGTH: 23
<212> TYPE: DNA
<213> ORGANISM: artificial sequence
<220> FEATURE:
<223> OTHER INFORMATION: primers

<400> SEQUENCE: 69
ctttggagtt acccattcct ttc                                    23

<210> SEQ ID NO 70
<211> LENGTH: 23
<212> TYPE: DNA
<213> ORGANISM: artificial sequence
<220> FEATURE:
<223> OTHER INFORMATION: primers

<400> SEQUENCE: 70
cgggttctgc tcattctctt gga                                    23

<210> SEQ ID NO 71
<211> LENGTH: 24
<212> TYPE: DNA
<213> ORGANISM: artificial sequence
<220> FEATURE:
<223> OTHER INFORMATION: primers

<400> SEQUENCE: 71
cgctttgctc tcgtgtttct ctca                                   24

<210> SEQ ID NO 72
<211> LENGTH: 25
<212> TYPE: DNA
<213> ORGANISM: artificial sequence
<220> FEATURE:
<223> OTHER INFORMATION: primers

<400> SEQUENCE: 72
caccgcgagt ggagtacgcg aagag                                  25

<210> SEQ ID NO 73
<211> LENGTH: 25
<212> TYPE: DNA
<213> ORGANISM: artificial sequence
<220> FEATURE:
<223> OTHER INFORMATION: primers

<400> SEQUENCE: 73
aaacctcttc gcgtactcca ctcgc                                  25

<210> SEQ ID NO 74
<211> LENGTH: 24
<212> TYPE: DNA
<213> ORGANISM: artificial sequence
<220> FEATURE:
<223> OTHER INFORMATION: primers

<400> SEQUENCE: 74

```
caccgcacca tgatggccat gcgg                                              24

<210> SEQ ID NO 75
<211> LENGTH: 24
<212> TYPE: DNA
<213> ORGANISM: artificial sequence
<220> FEATURE:
<223> OTHER INFORMATION: primers

<400> SEQUENCE: 75
aaacccgcat ggccatcatg gtgc                                              24

<210> SEQ ID NO 76
<211> LENGTH: 24
<212> TYPE: DNA
<213> ORGANISM: artificial sequence
<220> FEATURE:
<223> OTHER INFORMATION: primers

<400> SEQUENCE: 76
caccgggact ttcccatcga acat                                              24

<210> SEQ ID NO 77
<211> LENGTH: 24
<212> TYPE: DNA
<213> ORGANISM: artificial sequence
<220> FEATURE:
<223> OTHER INFORMATION: primers

<400> SEQUENCE: 77
aaacatgttc gatgggaaag tccc                                              24

<210> SEQ ID NO 78
<211> LENGTH: 24
<212> TYPE: DNA
<213> ORGANISM: artificial sequence
<220> FEATURE:
<223> OTHER INFORMATION: primers

<400> SEQUENCE: 78
caccgtcaag aagacggccg aggc                                              24

<210> SEQ ID NO 79
<211> LENGTH: 24
<212> TYPE: DNA
<213> ORGANISM: artificial sequence
<220> FEATURE:
<223> OTHER INFORMATION: primers

<400> SEQUENCE: 79
aaacgcctcg gccgtcttct tgac                                              24

<210> SEQ ID NO 80
<211> LENGTH: 20
<212> TYPE: DNA
<213> ORGANISM: artificial sequence
<220> FEATURE:
<223> OTHER INFORMATION: primers

<400> SEQUENCE: 80
cgggagctct ccatgcattt                                                   20

<210> SEQ ID NO 81
<211> LENGTH: 22
<212> TYPE: DNA
```

```
                           -continued

<213> ORGANISM: artificial sequence
<220> FEATURE:
<223> OTHER INFORMATION: primers

<400> SEQUENCE: 81
gacagatact gcgacatagg gt                                          22

<210> SEQ ID NO 82
<211> LENGTH: 21
<212> TYPE: DNA
<213> ORGANISM: artificial sequence
<220> FEATURE:
<223> OTHER INFORMATION: primers

<400> SEQUENCE: 82
gctaagaccc aaactgggat t                                           21

<210> SEQ ID NO 83
<211> LENGTH: 21
<212> TYPE: DNA
<213> ORGANISM: artificial sequence
<220> FEATURE:
<223> OTHER INFORMATION: primers

<400> SEQUENCE: 83
ggtttgctga agatggcggt a                                           21
```